United States Patent
Roth et al.

(10) Patent No.: US 8,877,754 B2
(45) Date of Patent: Nov. 4, 2014

(54) COMPOUNDS, PHARMACEUTICAL COMPOSITIONS AND USES THEREOF

(75) Inventors: Gerald Juergen Roth, Biberach an der Riss (DE); Martin Fleck, Warthausen (DE); Heike Neubauer, Eberhardzell (DE); Bernd Nosse, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 159 days.

(21) Appl. No.: 13/211,475

(22) Filed: Aug. 17, 2011

(65) Prior Publication Data
US 2012/0214782 A1  Aug. 23, 2012

(30) Foreign Application Priority Data
Sep. 6, 2010  (EP) .................................... 10175456

(51) Int. Cl.
| | | |
|---|---|---|
| *C07D 239/42* | (2006.01) | |
| *A61K 31/426* | (2006.01) | |
| *C07D 261/14* | (2006.01) | |
| *C07D 213/64* | (2006.01) | |
| *A61K 31/44* | (2006.01) | |
| *C07C 237/22* | (2006.01) | |
| *C07C 235/38* | (2006.01) | |
| *C07C 255/25* | (2006.01) | |
| *C07C 235/36* | (2006.01) | |
| *C07C 235/34* | (2006.01) | |

(52) U.S. Cl.
CPC ............ *C07D 239/42* (2013.01); *C07D 213/64* (2013.01); *A61K 31/44* (2013.01); *C07C 237/22* (2013.01); *C07C 235/38* (2013.01); *C07C 255/25* (2013.01); *C07C 235/36* (2013.01); *C07C 235/34* (2013.01)
USPC ........... 514/247; 514/256; 514/275; 514/357; 514/365; 514/374; 514/406; 514/428; 514/460; 514/461; 514/399; 514/617; 514/622; 544/224; 544/329; 544/332; 546/266; 548/203; 548/204; 548/205; 548/236; 548/335.5; 548/375.1; 548/566; 549/419; 549/496; 564/171

(58) Field of Classification Search
CPC .. C07D 307/42; C07D 239/42; C07D 261/14; A61K 31/341; A61K 31/505; A61K 31/426
USPC .......... 564/171; 514/617, 622, 247, 256, 275, 514/357, 365, 374, 399, 406, 428, 460, 514/461; 544/224, 329, 332; 546/266; 548/203, 204, 205, 236, 335.5, 375.1, 548/566; 549/419, 496
See application file for complete search history.

(56) References Cited

U.S. PATENT DOCUMENTS
2005/0267115 A1  12/2005  Stenkamp et al.

FOREIGN PATENT DOCUMENTS
| | | |
|---|---|---|
| WO | 0183465 A2 | 11/2001 |
| WO | 2009094123 A1 | 7/2009 |
| WO | 2010050445 A1 | 5/2010 |

OTHER PUBLICATIONS

Yu et al., A regioselective synthesis of 3-benzazepinones via intramolecular hydroamidation of acetylenes, Tetrahedron Letters 47 (2006), pp. 3811-3814.*
Zhang et al., Regioselective Synthesis of 3-Benzazepinones and Unexpected 5-Bromo-3-benzazepinones, J. Org. Chem., 2010, 75, pp. 3671-3677 (published on web May 5, 2010).*
International Search Report, form PCT/ISA/210, and Written Opinion, form PCT/ISA/237, for corresponding application PCT/EP2011/065332, date of mailing Oct. 26, 2011.
Corbett et al., Review of recent acetyl-CoA carboxylaase inhibitor patents: mid-2007-2008, Expert Opinion on Therapeutic Patents, vol. 19, No. 7, Jul. 2009, pp. 943-956.
Drefahl et al., Polyphenyl-polyen-ine, Chemische Berichte, vol. 93, No. 4, Apr. 1960, pp. 990-998.

* cited by examiner

*Primary Examiner* — Deepak Rao
(74) *Attorney, Agent, or Firm* — Michael P. Morris; Alan R. Stempel

(57) ABSTRACT

The invention relates to new compounds of the formula I $$Ar^1-C\equiv C-Ar^2-X-Y\diagdown_{N-T^1}^{} \diagup T^2$$

to their use as medicaments, to methods for their therapeutic use and to pharmaceutical compositions containing them.

10 Claims, No Drawings

COMPOUNDS, PHARMACEUTICAL COMPOSITIONS AND USES THEREOF

FIELD OF THE INVENTION

This invention relates to new compounds, in particular ethyne derivatives, to processes for preparing such compounds, to their use as inhibitors of acetyl-CoA carboxylases, to methods for their therapeutic use, in particular in diseases and conditions mediated by the inhibition of acetyl-CoA carboxylase enzyme(s), and to pharmaceutical compositions comprising them.

BACKGROUND OF THE INVENTION

Obesity is a major public health issue not only for the EU, USA, Japan but also for the world in general. It is associated with a number of serious diseases including diabetes, dyslipidemia, hypertension, cardiovascular and cerebrovascular diseases.

Although the underlying mechanisms are not yet fully understood, the impairment of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G1 Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (D Saggerson, Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62(2):237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, nonalcoholic steatohepatitis (NASH) and the metabolic syndrome (L. Tong, H J Harwood Jr., Journal of Cellular Biochemistry 99:1476-1488, 2006; J W Corbett, J H Jr. Harwood, Recent Pat Cardiovasc Drug Discov. 2007 November; 2(3):162-80).

Furthermore recent data show that cellular toxicity mediated by lipids (lipotoxicity) is implicated in the susceptibitlity to diabetes associated nephropathy (for review see M Murea, B I Freedmann, J S Parks, P A Antinozzi, S C Elbein, L M Ma; Clin J Am Soc Nephrol. 2010; 5:2373-9). A large-scale genome-wide association study in japanese patients identified single nucleotide polymorphism in the ACC2 gene (ACACB) associated with diabetic nephropathy risk which was replicated in nine independent cohorts. In the kidney, dysregulation of fatty acid metabolism leading to increased fatty acid levels is believed to lead to glomerular and tubular dysfunction (M Murea, B I Freedmann, J S Parks, P A Antinozzi, S C Elbein, L M Ma; Clin J Am Soc Nephrol. 2010; 5:2373-9). Therefore inhibitors targeting ACC as key molecule involved in lipid oxidation have the potential to be beneficial for favorably affecting diabetic nephropathy.

Additionally, insulin resistance, deregulated lipid metabolism, lipotoxicity and increased intramuscular lipids have also been described to play a role in type 1 diabetes (I E Schauer, J K Snell-Bergeon, B C Bergman, D M Maahs, A Kretowski, R H Eckel, M Rewers Diabetes 2011; 60:306-14; P Ebeling, B Essén-Gustavsson, J A Tuominen and V A Koivisto Diabetologia 41: 111-115; K J Nadeau, J G Regensteiner, T A Bauer, M S Brown, J L Dorosz, A Hull, P Zeitler, B Draznin, J E B. Reusch J Clin Endocrinol Metab, 2010, 95:513-521). Therefore ACC inhibitors are also considered as interesting drugs for the treatment of type 1 diabetes.

In addition ACC inhibitors also have the potential to intervene in the progression of diseases that result from the rapid growth of malignant cells or invading organisms that are dependent on endogenous lipid synthesis to sustain their rapid proliferation. De novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao Front Biosci 2010; 2:515-26)

Furthermore in central nervous system disorders including but not limited to Alzheimer's disease, Parkinson disease and epilepsy, impairments in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (S T Henderson Neurotherapeutics, 2008, 5:470-480; L C Costantini, L J Barr, J L Vogel, S T Henderson BMC Neurosci. 2008, 9 Suppl 2:S16; K W Barañano, A L Hartman. Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, AD, hypoxia, ischemia, amyotrophic lateral sclerosis and glioma (L C Costantini, L J Barr, J L Vogel, S T Henderson BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson BMC Neurosci. 2008, 9 Suppl 2:S16; K W Barañano, A L Hartman. Curr Treat Options Neurol. 2008; 10:410-9).

Furthermore, the potential of ACC inhibitors as antifungal agents and as antibacterial agents is well documented (L. Tong, H J Harwood Jr. Journal of Cellular Biochemistry 99:1476-1488, 2006). In addition, ACC inhibitors can be used to combat viral infections. It was discovered recently that viruses rely on the metabolic network of their cellular hosts to provide energy and building blocks for viral replication (Munger J, B D Bennett, A Parikh, X J Feng, J McArdle, H A Rabitz, T Shenk, J D Rabinowitz. Nat Biotechnol. 2008; 26:1179-86). A flux measurement approach to quantify changes in metabolic activity induced by human cytomegalovirus (HCMV) elucidated that infection with HCMV markedly changed fluxes through much of the central carbon metabolism, including glycolysis, tricarboxylic acid cycle and fatty acid biosynthesis. Pharmacological inhibition of fatty acid biosynthesis suppressed the replication of two divergent enveloped viruses (HCMV and influenza A) indicating that fatty acid synthesis is essential for the replication. These examples show that acetyl-CoA fluxes and de novo fatty acid biosynthesis are critical to viral survival and propagation as the newly synthesized fatty acids and phospholipids are important for formation of viral envelopes. Changing the metabolic flux influences the absolute quantity of phospholipid available, the chemical composition and physical properties of the envelope negatively affect viral growth and replication. Hence, ACC inhibitors acting on key enzymes in the fatty acid metabolism, have the potential to be antiviral drugs.

AIM OF THE PRESENT INVENTION

The aim of the present invention is to provide new compounds, in particular new ethyne derivatives, which are active with regard to acetyl-CoA carboxylase enzyme(s).

Another aim of the present invention is to provide new compounds, in particular new ethyne derivatives, which are active with regard to ACC2.

A further aim of the present invention is to provide new compounds, in particular new ethyne derivatives, which have an inhibitory effect on the enzyme acetyl-CoA carboxylase enzyme(s) in vitro and/or in vivo and possess suitable pharmacological and pharmacokinetic properties to use them as medicaments.

A further aim of the present invention is to provide new compounds, in particular new ethyne derivatives, which have an inhibitory effect on the enzyme ACC2 in vitro and/or in vivo and possess suitable pharmacological and pharmacokinetic properties to use them as medicaments.

A further aim of the present invention is to provide effective ACC inhibitors, in particular for the treatment of metabolic disorders, for example of obesity and/or diabetes.

A further aim of the present invention is to provide methods for treating a disease or condition mediated by the inhibition of acetyl-CoA carboxylase enzyme(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular ethyne derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to enzyme(s) of acetyl-CoA carboxylases.

According to another aspect of the present invention it has been found that the new compounds of general formula (I) as described hereinafter exhibit an inhibiting activity with regard to ACC2.

Therefore, in a first aspect the present invention provides a compound of general formula (I)

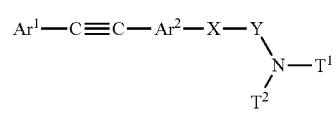

wherein
$Ar^1$ is selected from the group $Ar^1$-G1 consisting of aryl and heteroaryl all of which may be optionally substituted with one or more substituents $R^A$, wherein two substituents $R^A$ linked to adjacent C-atoms of $Ar^1$ may be connected with each other and together form a $C_{3-5}$-alkylene bridging group in which 1, 2 or 3 —$CH_2$-groups may be replaced by O, C(=O), S, S(=O), S(=O)$_2$, NH or N($C_{1-4}$-alkyl)-, wherein the alkylene bridge may optionally be substituted by one or two $C_{1-3}$-alkyl groups; and $R^A$ is selected from the group $R^A$-G1 consisting of H, F, Cl, Br, I, CN, OH, —NO$_2$, $C_{1-6}$-alkyl, $C_{2-6}$-alkenyl, $C_{2-6}$-alkynyl, $C_{3-10}$-carbocyclyl, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{1-6}$-alkyl-S(=O)—, $C_{1-6}$-alkyl-S(=O)$_2$—, $C_{3-10}$-carbocyclyl-S—, $C_{3-10}$-carbocyclyl-$C_{1-3}$-alkyl-S—, $C_{1-4}$-alkyl-C(=O)—, $C_{3-10}$-carbocyclyl-C(=O)—, $R^{N1}R^{N2}N$—, $R^{N1}R^{N2}N$—$C_{1-3}$-alkyl, $R^{N1}R^{N2}N$—$C_{2-3}$-alkyl-O—, $R^{N1}R^{N2}N$—C(=O)—, $R^{N1}R^{N2}N$—S(=O)$_2$—, $C_{1-6}$-alkyl-C(=O)—$NR^{N1}$—, $C_{1-6}$-alkyl-S(=O)$_2$—$NR^{N1}$—, $C_{1-6}$-alkyl-C(=O)—$NR^{N1}$—$C_{1-3}$-alkyl-, HO—C(=O)—, $C_{1-6}$-alkyl-O—C(=O)—, heterocyclyl, heterocyclyl-O—, heterocyclyl-$C_{1-3}$-alkyl, heterocyclyl-$C_{1-3}$-alkyl-O—, heterocyclyl-C(=O)—, aryl, aryl-$C_{1-3}$-alkyl, aryl-O—, aryl-$C_{1-3}$-alkyl-O—, heteroaryl, heteroaryl-$C_{1-3}$-alkyl, heteroaryl-$C_{1-3}$-alkyl-C(=O)—, heteroaryl-O— and heteroaryl-$C_{1-3}$-alkyl-O—, wherein in each carbocyclyl and heterocyclyl a —$CH_2$-group may optionally be replaced by —C(=O)— or —C(=$CR^{Alk}_2$)—, and wherein each carbocyclyl and heterocyclyl may be optionally substituted with one or more $C_{1-4}$-alkyl, which may be optionally substituted with one or more substituents $R^C$, and wherein each alkyl, carbocyclyl and heterocyclyl may be optionally substituted with one or more substituents $R^C$, and wherein each heterocyclyl may be optionally substituted with aryl or heteroaryl, and wherein each aryl and heteroaryl group may be optionally substituted with one or more substituents L, $R^C$ is selected from the group $R^C$-G1 consisting of F, Cl, Br, CN, OH, $C_{1-4}$-alkyl-O—, $C_{3-7}$-cycloalkyl-O—, $C_{3-7}$-cycloalkyl-$C_{1-3}$-alkyl-O—, $H_2N$—, $(C_{1-4}$-alkyl)NH—, $(C_{1-4}$-alkyl)$_2$N—, $C_{1-4}$-alkyl-C(=O)—, $C_{1-4}$-alkyl-S(=O)$_2$—, HO—C(=O)—, $C_{1-4}$-alkyl-O—C(=O)—, $H_2N$—C(=O)—, $(C_{1-4}$-alkyl)HN—C(=O)— and $(C_{1-4}$-alkyl)$_2$N—C(=O)—, wherein each alkyl or cycloalkyl may be optionally substituted with one or more substituents selected from F and OH; and $R^{N1}$ is selected from the group $R^{N1}$-G1 consisting of H, $C_{1-6}$-alkyl, $C_{3-10}$-carbocyclyl, $C_{3-10}$-carbocyclyl-$C_{1-3}$-alkyl, $C_{3-6}$-alkenyl, $C_{3-6}$-alkynyl, heterocyclyl, heterocyclyl-$C_{1-3}$-alkyl, aryl, aryl-$C_{1-3}$-alkyl, heteroaryl and heteroaryl-$C_{1-3}$-alkyl, wherein each carbocyclyl and heterocyclyl may be optionally substituted with one or more $C_{1-4}$-alkyl, and wherein in each carbocyclyl and heterocyclyl a —$CH_2$-group may optionally be replaced by —C(=O)—, and wherein each alkyl, carbocyclyl and heterocyclyl may be optionally substituted with one or more substituents $R^C$, and wherein each aryl and heteroaryl group may be optionally substituted with one or more substituents L, $R^{N2}$ is selected from the group $R^{N2}$-G1 consisting of H and $C_{1-6}$-alkyl; and $R^{Alk}$ is selected from the group $R^{Alk}$-G1 consisting of H and $C_{1-6}$-alkyl which may be substituted with one or more F atoms; and $Ar^2$ is selected from the group $Ar^2$-G1 consisting of phenyl and a 5- or 6-membered monocyclic aromatic carbocyclic ring system containing 1, 2 or 3 heteroatoms selected from N, O, or S, wherein all of the before mentioned groups may be optionally substituted with one or more substituents L; and L is selected from the group L-G1 consisting of F, Cl, Br, CN, OH, $C_{1-4}$-alkyl-, $C_{1-4}$-alkyl-O—, $C_{1-4}$-alkyl-S—, $C_{1-4}$-alkyl-S(=O)$_2$—, $H_2N$—, $(C_{1-4}$-alkyl)NH—, $(C_{1-4}$-alkyl)$_2$N— and heterocyclyl, wherein each alkyl may be optionally substituted with one or more F-atoms and/or with a substituent selected from OH, $C_{1-3}$-alkyl-O— and CN; and wherein two substituents L attached to an aryl or heteroaryl group may be linked to each other and form a $C_{2-5}$-alkylene bridging group in which 1 or 2 —$CH_2$-groups may be replaced by a group independently of each other selected from O, S, NH and N($C_{1-4}$-alkyl)-, wherein the $C_{2-5}$-alkylene bridging group is optionally be substituted by 1 or 2 $C_{1-3}$-alkyl groups; and X is selected from the group X-G1 consisting of a straight chain $C_{1-3}$-alkylene group which may be optionally substituted with one or more groups selected from $C_{1-3}$-alkyl and $C_{1-3}$-alkyl-O—$C_{1-3}$-alkyl, and wherein two alkyl substituents may be connected with each other and together form a $C_{1-5}$-alkylene bridging group in which 1 or 2 —$CH_2$-groups may be replaced by a group independently of each other selected from O, S, NH or N($C_{1-4}$-alkyl)-, wherein the $C_{1-5}$-alkylene bridging group may be optionally substituted by 1 or 2 $C_{1-3}$-alkyl groups; and Y is selected from the group Y-G1 consisting of —C(=O)— and —S(=O)$_2$—;

$T^1$ is selected from the group $T^1$-G1 consisting of H, $C_{1-6}$-alkyl, $C_{2-6}$-alkenyl, $C_{2-6}$-alkynyl, $C_{3-10}$-carbocyclyl, $C_{3-10}$-carbocyclyl-$C_{1-3}$-alkyl, $R^{N1}N^{R2}$—N—$C_{1-3}$-alkyl-, heterocyclyl, heterocyclyl-$C_{1-3}$-alkyl, aryl, aryl-$C_{1-3}$-alkyl, heteroaryl and heteroaryl-$C_{1-3}$-alkyl, wherein in each carbocyclyl and heterocyclyl a —$CH_2$-group may optionally be replaced by —C(=O)—, and wherein each carbocyclyl and heterocyclyl may be optionally substituted with one or more $C_{1-4}$-alkyl, which may be optionally substituted with one or more substituents $R^C$, and wherein each alkyl, carbocyclyl and heterocyclyl may be optionally substituted with one or more substituents $R^C$, and wherein each aryl and heteroaryl group may be optionally substituted with one or more substituents L, or the groups $T^1$ and $T^2$ may be connected with each other and together form a group which is selected from the group $T^1$-$T^2$-G1 consisting of a $C_{3-6}$-alkylene group wherein a —$CH_2$-group may be replaced by O, S or —C(=O)—, and wherein the alkylene group ich may be optionally substituted with one or more substituents selected from F, Cl, Br, OH, CN, $C_{1-4}$-alkyl, $C_{3-10}$-carbocyclyl, $C_{3-10}$-carbocyclyl-$C_{1-3}$-alkyl, $C_{1-4}$-alkyl-O—, $C_{3-7}$-cycloalkyl-O—, $C_{3-10}$-carbocyclyl-$C_{1-3}$-alkyl-O—, $H_2N$—, $(C_{1-4}$-alkyl)NH—, $(C_{1-4}$-alkyl)$_2$N—, $C_{1-4}$-alkyl-C(=O)—, $C_{1-4}$-alkyl-S(=O)$_2$—, HO—C(=O)— and $C_{1-4}$-alkyl-O—C(=O)—, wherein each alkyl or carbocyclyl may be optionally substituted with one or more substituents selected from $R^C$; and $T^2$ is selected from the group $T^2$-G1 consisting of H and $C_{1-6}$-alkyl;

including any tautomers and stereoisomers thereof, or a salt thereof or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase enzyme(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described hereinbefore and hereinafter.

According to another aspect of the invention, there is provided a compound of the general formula (I) or a pharmaceutically acceptable salt thereof for a therapeutic method as described hereinbefore and hereinafter.

In a further aspect this invention relates to a method for treating a disease or condition mediated by the inhibition of acetyl-CoA carboxylase enzyme(s) in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of the enzyme(s) acetyl-CoA carboxylase.

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $Ar^1$, $Ar^2$, X, Y, $T^1$, $T^2$, $R^A$, $R^C$, $R^{N1}$, $R^{N2}$, $R^{Alk}$, L, are defined as above and hereinafter. If residues, substituents, or groups occur several times in a compound, as for example $R^C$, $R^{N1}$, $R^{N2}$ or L, they may have the same or different meanings. Some preferred meanings of individual groups and substituents of the compounds according to the invention will be given hereinafter. Any and each of these definitions may be combined with each other.

$Ar^1$:

$Ar^1$-G1:

The group $Ar^1$ is preferably selected from the group $Ar^1$-G1 as defined hereinbefore and hereinafter.

$Ar^1$-G2:

In one embodiment the group $Ar^1$ is selected from the group $Ar^1$-G2 consisting of phenyl, dihydronaphthyl, tetrahydronaphthyl, naphthyl and a 5- or 6-membered monocyclic or 9- or 10-membered bicyclic-ring system containing 1, 2, 3 or 4 heteroatoms selected from N, O, S, or S(O)$_r$ with r=1 or 2 wherein at least one of the heteroatoms is part of an aromatic ring, and wherein all of the before mentioned groups may be optionally substituted with one or more substituents $R^A$, particularly wherein all of the before mentioned groups may be optionally substituted with a substituent $R^A$ and optionally one or more substituents L, and wherein two substituents $R^A$ linked to adjacent C-atoms of $Ar^1$ may be connected with each other and together form a $C_{3-5}$-alkylene bridging group in which 1, 2 or 3 $CH_2$-groups may be replaced by O, C(=O), S, S(=O), S(=O)$_2$, NH or N($C_{1-4}$-alkyl)-, wherein the alkylene bridging group may optionally be substituted by one or two $C_{1-3}$-alkyl groups.

$Ar^1$-G3:

In another embodiment the group $Ar^1$ is selected from the group $Ar^1$-G3 consisting of phenyl, naphthyl, pyridyl, 2H-pyridin-2-onyl, pyrimidinyl, pyridazinyl, pyrazinyl, furanyl, thienyl, pyrrolyl, imidazolyl, triazolyl, oxazolyl, isoxazolyl, pyrazolyl, thiazolyl, quinolinyl, isoquinolinyl, indolyl, benzofuranyl, indanonyl, benzoimidazolyl, benzooxazolyl, benzotriazolyl, 2,3-dihydrobenzofuranyl, benzo[1,3]dioxolyl, 2,3-dihydro-benzo[1,4]dioxinyl and 3,4-dihydro-2H-benzo[b][1,4]dioxepinyl, wherein the before mentioned bicyclic groups preferably are linked to the —C≡C— group of the core structure of the formula (I) via an aromatic or heteroaromatic ring of the bicyclic group, and wherein all of the before mentioned mono- and bicyclic groups may be optionally substituted with one or more substituents $R^A$, particularly wherein all of the before mentioned mono- or bicyclic groups may be optionally substituted with a substituent $R^A$ and optionally one or more substituents L.

$Ar^1$-G4:

In another embodiment the group $Ar^1$ is selected from the group $Ar^1$-G4 consisting of phenyl, naphthyl, pyridyl, 2H-pyridin-2-onyl, pyrimidinyl, pyridazinyl, pyrazinyl, furanyl, oxazolyl, isoxazolyl, pyrazolyl, thiazolyl, quinolinyl, indolyl, benzofuranyl, 2,3-dihydrobenzofuranyl, indan-1-onyl, benzo[1,3]dioxolyl, 2,3-dihydro-benzo[1,4]dioxinyl and 3,4-dihydro-2H-benzo[b][1,4]dioxepinyl, wherein the before mentioned bicyclic groups preferably are linked to the —C≡C— group of the core structure of the formula (I) via an aromatic or heteroaromatic ring of the bicyclic group, and wherein all of the before mentioned mono- and bicyclic groups may be optionally substituted with one or more substituents $R^A$, particularly wherein all of the before mentioned mono- or bicyclic groups may be optionally substituted with a substituent $R^A$ and optionally one or more substituents L.

$Ar^1$-G5:

In another embodiment the group $Ar^1$ is selected from the group $Ar^1$-G5 consisting of:

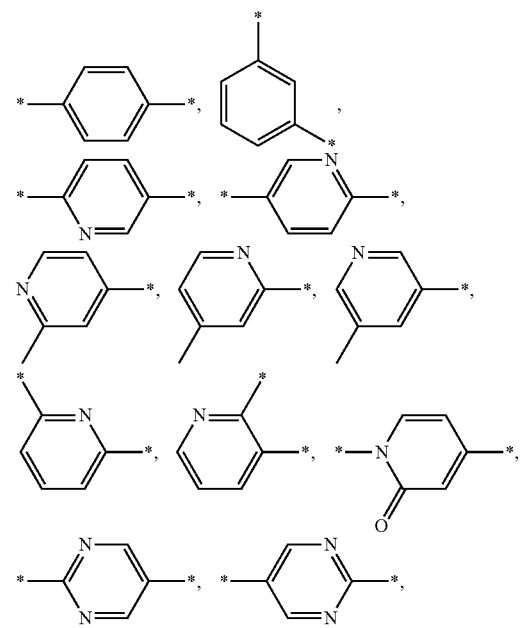

-continued

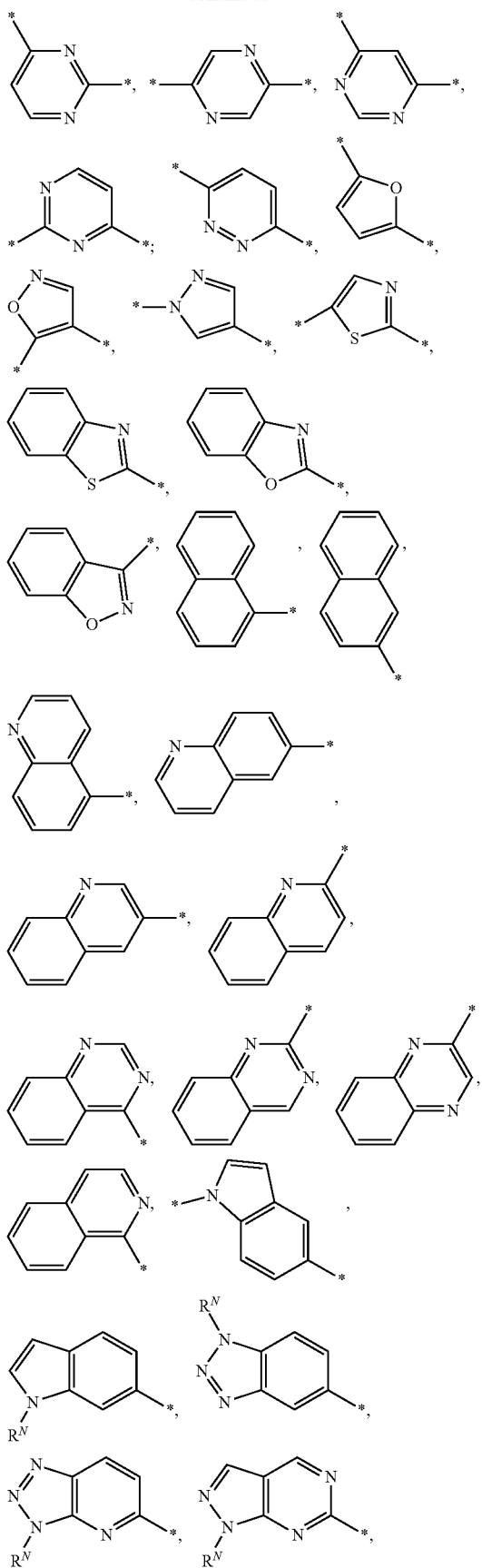

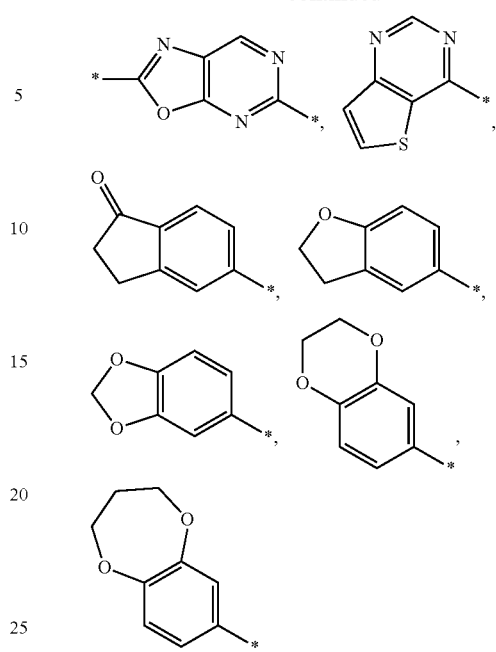

wherein the asterisk to the right side of each cyclic group indicates the bond which is connected to the —C≡C— group of the core structure of the formula (I), and if existing the asterisk to the left side of each cyclic group indicates the bond which is connected to a substituent $R^A$ or H, and in addition each of the before mentioned cyclic groups is optionally substituted with one or more further substituents $R^A$, in particular one or more substituents L, and the substituent $R^N$ is H or $C_{1-4}$-alkyl.

Ar¹-G6:

In another embodiment the group Ar¹ is selected from the group Ar¹-G6 consisting of:

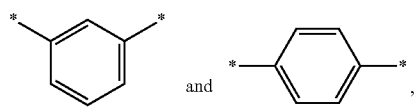 [SMILES: *c1cccc(*)c1 ; *c1ccc(*)cc1]

wherein the asterisk to the right side of the cyclic group indicates the bond which is connected to the —C≡C— group of the core structure of the formula (I), and the asterisk to the left side of the cyclic group indicates the bond which is connected to a substituent $R^A$ or H, and in addition the before mentioned cyclic group is optionally substituted with one or more further substituents $R^A$, in particular one or more substituents L.

Examples of members of the group Ar¹-G6 are without being limited to it:

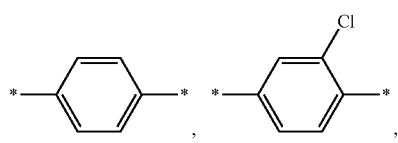

-continued

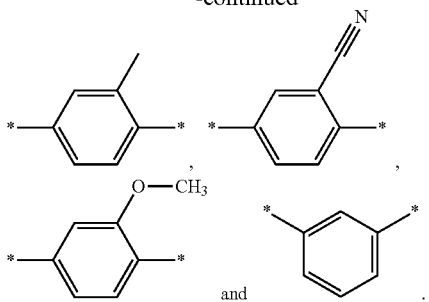

Ar¹-G7:

In another embodiment the group Ar¹ is selected from the group Ar¹-G7 consisting of 6-membered aromatic rings containing 1 or 2 N-atoms, wherein said rings may be optionally substituted with one or more substituents $R^A$, particularly wherein said rings may be optionally substituted with a substituent $R^A$ and optionally one or more substituents L. Examples of members of the group Ar¹-G7 are:

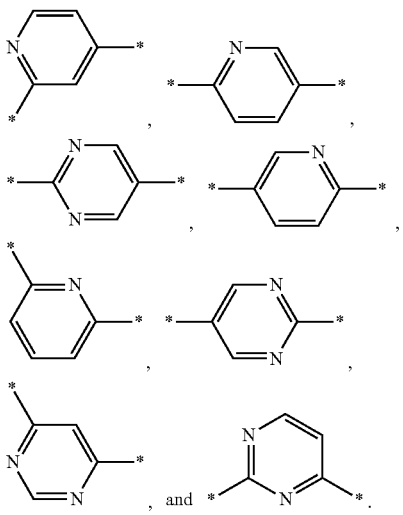

wherein the asterisk to the right side of each cyclic group indicates the bond which is connected to the —C≡C-group of the core structure of the formula (I), and the asterisk to the left side of each cyclic group indicates the bond which is connected to a substituent $R^A$, and in addition each of the before mentioned cyclic groups is optionally substituted with one or more further substituents $R^A$, in particular one or more substituents L.

Preferred examples of members of the group Ar¹-G7 are without being limited to it:

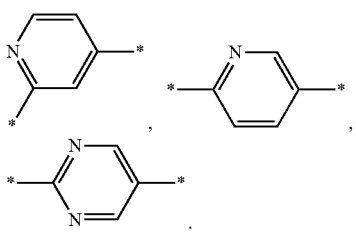

$R^A$:

$R^A$-G1

The group $R^A$ is preferably selected from the group $R^A$-G1 as defined hereinbefore and hereinafter, $R^A$-G2:

In another embodiment the group $R^A$ is selected from the group $R^A$-G2 consisting of H, F, Cl, Br, I, CN, OH, $NO_2$, $C_{1-6}$-alkyl, $C_{3-10}$-carbocyclyl, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, $C_{1-4}$-alkyl-C(=O)—, $R^{N1}R^{N2}N$—, $R^{N1}R^{N2}N$—$C_{2-3}$-alkyl-O—, $R^{N1}R^{N2}N$—C(=O)—, HO—C(=O)—, $C_{1-6}$-alkyl-O—C(=O)—, heterocyclyl, heterocyclyl-O—, heterocyclyl-$C_{1-3}$-alkyl, heterocyclyl-$C_{1-3}$-alkyl-O—, heterocyclyl-C(=O)—, aryl, aryl-$C_{1-3}$-alkyl, aryl-O—, aryl-$C_{1-3}$-alkyl-O—, heteroaryl, heteroaryl-$C_{1-3}$-alkyl, heteroaryl-O— and heteroaryl-$C_{1-3}$-alkyl-O—;

wherein heterocyclyl is defined as hereinbefore and hereinafter, or alternatively each heterocyclyl is selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroquinolinyl, dihydroisoquinolinyl, dihydroindolyl, dihydroisoindolyl, oxetanyl, tetrahydrofuranyl and tetrahydropyranyl, or from the group consisting of

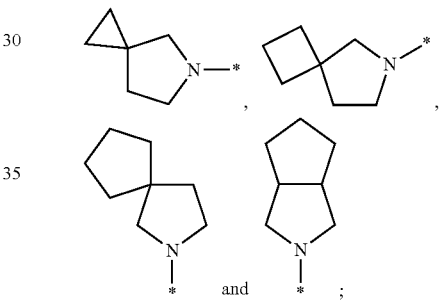

and wherein carbocyclyl is defined as hereinbefore and hereinafter, or each carbocyclyl is preferably selected from $C_{3-7}$-cycloalkyl, indanyl and tetrahydronaphthyl; and wherein heteroaryl is defined as hereinbefore and hereinafter, or each heteroaryl is preferably selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, benzofuranyl, indolyl, quinolinyl and indazolyl; and wherein in each heterocyclyl and carbocyclyl a —$CH_2$-group may optionally be replaced by —C(=O)— or —C(=$CR^{Alk}_2$)—; and wherein each carbocyclyl and heterocyclyl may be optionally substituted with one or more $C_{1-3}$-alkyl, which may be substituted as defined hereinafter, and wherein each alkyl, carbocyclyl and heterocyclyl may be optionally substituted with one or more F atoms; and wherein each alkyl, carbocyclyl and heterocyclyl may be optionally substituted with 1, 2 or 3 substituents $R^C$, which are independently of each other selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH— and ($C_{1-3}$-alkyl)$_2$N—, HO—C(=O)— and $C_{1-4}$-alkyl-O—C(=O)—; and wherein each $R^{N1}$ is selected from the group $R^{N1}$-G1, $R^{N1}$-G2 or $R^{N1}$-G3 as defined hereinbefore and hereinafter; and each $R^{N2}$ is selected from the group $R^{N2}$-G1 or $R^{N2}$-G2 as defined hereinbefore and hereinafter; and wherein each carbocyclyl or heterocyclyl may be optionally substituted with an aryl or heteroaryl group, in particular with phenyl or pyridyl, and wherein each aryl and heteroaryl group may be optionally substituted with one or more substituents L, wherein L is selected from the groups L-G1, L-G2 or L-G3 as defined hereinbefore and hereinafter.

$R^A$-G2a:

In another embodiment the group $R^A$ is selected from the group $R^A$-G2a consisting of $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, heterocyclyl-O— and heterocyclyl-$C_{1-3}$-alkyl-O—, phenyl-O—, phenyl-$C_{1-3}$-alkyl-O—, heteroaryl-O— and heteroaryl-$C_{1-3}$-alkyl-O—;

wherein each heteroaryl is defined as hereinbefore and hereinafter; preferably heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, triazolyl and tetrazolyl; and wherein heterocyclyl is defined as hereinbefore and hereinafter, or each heterocyclyl is preferably selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroquinolinyl, dihydroisoquinolinyl, dihydroindolyl, dihydroisoindolyl, oxetanyl, tetrahydrofuranyl and tetrahydropyranyl, or from the group consisting of

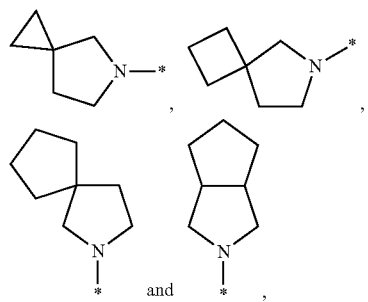

and wherein carbocyclyl is defined as hereinbefore and hereinafter, or each carbocyclyl is preferably selected from $C_{3-7}$-cycloalkyl, indanyl and tetrahydronaphthyl; and wherein in each heterocyclyl and carbocyclyl a $CH_2$-group may optionally be replaced by —C(=O)— or —C(=CR$^{Alk}_2$)—; and wherein each carbocyclyl and heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with 1, 2 or 3 substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2$N—, ($C_{1-3}$-alkyl)NH— and ($C_{1-3}$-alkyl)$_2$N—, HO—C(=O)— and $C_{1-4}$-alkyl-O—C(=O)—; and wherein each phenyl and heteroaryl group may be optionally substituted with one or more substituents L, wherein L is selected from the groups L-G1, L-G2 or L-G3 as defined hereinbefore and hereinafter.

$R^A$-G2b:

In another embodiment the group $R^A$ is selected from the group $R^A$-G2b consisting of $C_{1-6}$-alkyl, $C_{3-10}$-carbocyclyl, $C_{3-10}$-carbocyclyl-$C_{1-3}$-alkyl, heterocyclyl, heterocyclyl-$C_{1-3}$-alkyl, aryl, aryl-$C_{1-3}$-alkyl, heteroaryl and heteroaryl-$C_{1-3}$-alkyl;

wherein heterocyclyl is defined as hereinbefore and hereinafter, or each heterocyclyl is preferably selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroquinolinyl, dihydroisoquinolinyl, dihydroindolyl, dihydroisoindolyl, oxetanyl, tetrahydrofuranyl and tetrahydropyranyl, or from the group consisting of

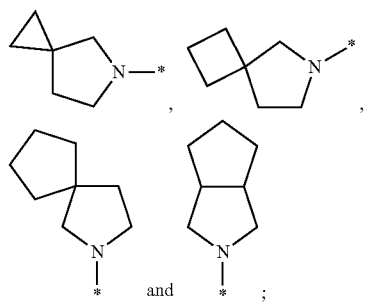

and wherein carbocyclyl is defined as hereinbefore and hereinafter, or each carbocyclyl is preferably selected from $C_{3-7}$-cycloalkyl, indanyl and tetrahydronaphthyl; and wherein heteroaryl is defined as hereinbefore and hereinafter, or each heteroaryl is preferably selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, benzofuranyl, indolyl, quinolinyl and indazolyl; and wherein in each heterocyclyl and carbocyclyl a $CH_2$-group may optionally be replaced by —C(=O)— or —C(=CR$^{Alk}_2$)—; and wherein each carbocyclyl and heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with 1, 2 or 3 substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2$N—, ($C_{1-3}$-alkyl)NH— and ($C_{1-3}$-alkyl)$_2$N—, HO—C(=O)— and $C_{1-4}$-alkyl-O—C(=O)—; and wherein each carbocyclyl or heterocyclyl may be optionally substituted with an aryl or heteroaryl group, in particular with phenyl or pyridyl; and wherein each aryl and heteroaryl group may be optionally substituted with one or more substituents L, wherein L is selected from the groups L-G1, L-G2 or L-G3 as defined hereinbefore and hereinafter.

$R^A$-G3:

In another embodiment the group $R^A$ is selected from the group $R^A$-G3 consisting of F, Cl, Br, I, CN, $NO_2$, $C_{1-6}$-alkyl, $C_{3-10}$-carbocyclyl-, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{1-4}$-alkyl-S—, $C_{3-10}$-carbocyclyl-O—, $C_{3-10}$-carbocyclyl-$C_{1-3}$-alkyl-O—, $C_{1-4}$-alkyl-C(=O)—, $R^{N1}R^{N2}N$—, $R^{N1}R^{N2}N$—$C_{2-3}$-alkyl-O—, $R^{N1}R^{N2}N$—C(=O)—, HO—C(=O)—, $C_{1-4}$-alkyl-O—C(=O)—, heterocyclyl, heterocyclyl-$C_{1-3}$-alkyl, heterocyclyl-O—, heterocyclyl-$C_{1-3}$-alkyl-O—, heterocyclyl-C(=O)—, phenyl, phenyl-O—, phenyl-$C_{1-3}$-alkyl-, phenyl-$C_{1-3}$-alkyl-O—, heteroaryl, heteroaryl-$C_{1-3}$-alkyl, heteroaryl-O— and heteroaryl-$C_{1-3}$-alkyl-O—;

wherein each heterocyclyl is selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroisoindolyl, oxetanyl, tetrahydrofuranyl and tetrahydropyranyl, or from the group consisting of

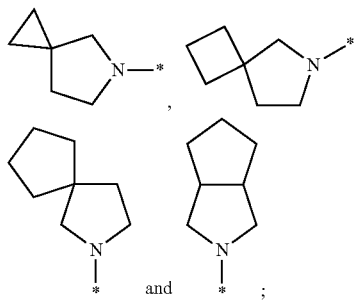

and wherein carbocyclyl is defined as hereinbefore and hereinafter, or each carbocyclyl is preferably selected from $C_{3-6}$-cycloalkyl, indanyl and tetrahydronaphthyl; most preferably carbocyclyl denotes $C_{3-6}$-cycloalkyl; and wherein in each carbocyclyl, pyrrolidinyl and piperidinyl a $CH_2$-group may optionally be replaced by —C(=O)— or —C(=$CR^{Alk}_2$)—; and wherein each heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, indazolyl, benzofuranyl, indolyl and quinolinyl; and wherein each carbocyclyl or heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with one or two substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-4}$-alkyl-O—C(=O)—; and wherein each $R^{N1}$ is selected from the group $R^{N1}$-G1, $R^{N1}$-G2 or $R^{N1}$-G3; and each $R^{N2}$ is selected from the group $R^{N2}$-G1 or $R^{N2}$-G2 as defined hereinbefore and hereinafter; and wherein each carbocyclyl and heterocyclyl may be optionally substituted with an aryl or heteroaryl group, in particular with phenyl or pyridyl; and wherein each phenyl and heteroaryl group may be optionally substituted with one or more substituents L, wherein L is selected from the groups L-G1, L-G2 or L-G3 as defined hereinbefore and hereinafter.

$R^A$-G4:

In another embodiment the group $R^A$ is selected from the group $R^A$-G4 consisting of F, Cl, Br, I, CN, $NO_2$, $C_{1-6}$-alkyl, $C_{3-10}$-carbocyclyl-, $C_{3-10}$-carbocyclyl-$C_{1-3}$-alkyl, $C_{1-6}$-alkyl-O—, $C_{3-5}$-alkenyl-O—, $C_{3-6}$-alkynyl-O—, $C_{3-10}$-carbocyclyl-O—, $C_{3-10}$-carbocyclyl-$C_{1-3}$-alkyl-O—, $R^{N1}R^{N2}N$—, heterocyclyl, heterocyclyl-$C_{1-3}$-alkyl, heterocyclyl-O—, heterocyclyl-$C_{1-3}$-alkyl-O—, phenyl, phenyl-O—, phenyl-$C_{1-3}$-alkyl-, phenyl-$C_{1-3}$-alkyl-O—, heteroaryl, heteroaryl-$C_{1-3}$-alkyl, heteroaryl-O— and heteroaryl-$C_{1-3}$-alkyl-O—;

wherein carbocyclyl is defined as hereinbefore and hereinafter, or each carbocyclyl is preferably selected from $C_{3-6}$-cycloalkyl, indanyl and tetrahydronaphthyl; most preferably carbocyclyl denotes $C_{3-6}$-cycloalkyl; and wherein each heterocyclyl is selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroisoindolyl, oxetanyl, tetrahydrofuranyl and tetrahydropyranyl, or from the group consisting of

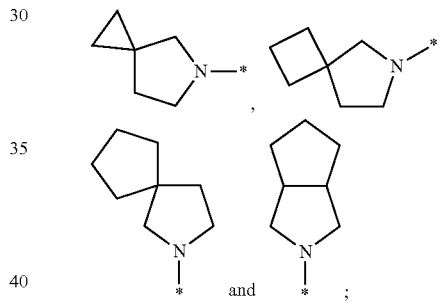

and wherein in each carbocyclyl and heterocyclyl a $CH_2$-group may optionally be replaced by —C(=O)— or —C(=$CR^{Alk}_2$)—; and wherein each heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, indazolyl, benzofuranyl, indolyl, and quinolinyl; and wherein each carbocyclyl and heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with one or two substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-4}$-alkyl-O—C(=O)—; and wherein each $R^{N1}$ is selected from the group $R^{N1}$-G1, $R^{N1}$-G2 or $R^{N1}$-G3; and each $R^{N2}$ is selected from the group $R^{N2}$-G1 or $R^{N2}$-G2 as defined hereinbefore and hereinafter; and wherein each carbocyclyl and heterocyclyl may be optionally substituted with an aryl or heteroaryl group, in particular with phenyl or pyridyl; and wherein each phenyl and heteroaryl group may be optionally substituted with one or more substituents L, wherein L is selected from the groups L-G1, L-G2 or L-G3 as defined hereinbefore and hereinafter.

$R^A$-G5:

In another embodiment the group $R^A$ is selected from the group $R^A$-G5 consisting of F, Cl, Br, I, ON, $C_{1-5}$-alkyl, $C_{3-6}$-cycloalkyl, $C_{1-5}$-alkyl-O—, $C_{3-6}$-cycloalkyl-O—, $C_{3-6}$-cycloalkyl-$C_{1-3}$-alkyl-O—, $R^{N1}R^{N2}N$—, phenyl, phenyl-O—, heteroaryl and heteroaryl-O—; and wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a $CH_2$-group may optionally be replaced by —O—; and wherein each alkyl and cycloalkyl may be optionally substituted with one or two substituents $R^C$, wherein $R^C$ is defined as hereinbefore and hereinafter; preferably $R^C$ is selected from the group consisting of Cl, Br, ON, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-3}$-alkyl-O—C(=O)—; and wherein each $R^{N1}$ is selected from the group $R^{N1}$-G1, $R^{N1}$-G2 or $R^{N1}$-G3 as defined hereinbefore and hereinafter; preferably $R^{N1}$ is selected from the group consisting of H, $C_{1-6}$-alkyl, $C_{3-6}$-cycloalkyl, $C_{3-6}$-cycloalkyl-$CH_2$— and phenyl-$CH_2$—, wherein each cycloalkyl may be optionally substituted with one or more $C_{1-4}$-alkyl, and wherein each alkyl and cycloalkyl may be optionally substituted with one or more substituents selected from F, and wherein each alkyl and cycloalkyl may be optionally substituted with a substituent selected from OH, $C_{1-3}$-alkyl-O— and $H_2N$—; and wherein each $R^{N2}$ is selected from the group $R^{N2}$-G1 or $R^{N2}$-G2 as defined hereinbefore and hereinafter; and wherein heteroaryl is defined as hereinbefore and hereinafter; preferably heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, benzofuranyl, indolyl and quinolinyl; and wherein each phenyl and heteroaryl group may be optionally substituted with one or more substituents L, wherein L is selected from the groups L-G1, L-G2 or L-G3 as defined hereinbefore and hereinafter.

$R^A$-G5a:

In another embodiment the group $R^A$ is selected from the group $R^A$-G5a consisting of $C_{1-5}$-alkyl-O—, $C_{3-5}$-alkenyl-O—, $C_{3-5}$-alkynyl-O—, $C_{3-6}$-cycloalkyl-O—, $C_{3-6}$-cycloalkyl-$C_{1-3}$-alkyl-O—, phenyl-O—, phenyl-$C_{1-3}$-alkyl-O—, heteroaryl-O— and heteroaryl-$C_{1-3}$-alkyl-O—;

wherein each heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, triazolyl and tetrazolyl; and wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a $CH_2$-group may optionally be replaced by —O—; and wherein each alkyl and cycloalkyl may be optionally substituted with one or two substituents $R^C$, wherein $R^C$ is defined as hereinbefore and hereinafter; preferably $R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-3}$-alkyl-O—C(=O)—; and wherein each phenyl and heteroaryl group may be optionally substituted with one or more substituents L, wherein L is selected from the groups L-G1, L-G2 or L-G3 as defined hereinbefore and hereinafter.

$R^A$-G5b:

In another embodiment the group $R^A$ is selected from the group $R^A$-G5b consisting of $C_{1-5}$-alkyl, $C_{3-6}$-cycloalkyl, $C_{3-6}$-cycloalkyl-$C_{1-3}$-alkyl, phenyl, phenyl-$C_{1-3}$-alkyl and heteroaryl;

wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a $CH_2$-group may optionally be replaced by —O—; and wherein each alkyl and cycloalkyl may be optionally substituted with one or two substituents $R^C$, wherein $R^C$ is defined as hereinbefore and hereinafter; preferably $R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-3}$-alkyl-O—C(=O)—; and wherein heteroaryl is defined as hereinbefore and hereinafter; preferably heteroaryl is selected from the group consisting of pyrrolyl, pyridyl, pyrimidinyl, pyridazinyl, pyrazinyl, furanyl, oxazolyl, isoxazolyl, pyrazolyl and thiazolyl; and wherein each phenyl and heteroaryl group may be optionally substituted with one or more substituents L, wherein L is selected from the groups L-G1, L-G2 or L-G3 as defined hereinbefore and hereinafter.

In the embodiments with regard to $R^A$ as described hereinbefore and hereinafter it is to be understood that the double or triple bond in the groups $C_{3-n}$-alkenyl-O— and $C_{3-n}$-alkynyl-O— (with n being an integer) is preferably not conjugated with the O— atom of that group.

$R^A$-G6:

In another embodiment the group $R^A$ is selected from the group $R^A$-G6 consisting of F, Cl, Br, I, CN, methyl, ethyl, n-propyl, i-propyl, n-butyl, t-butyl, $F_3O$—, HO—$CH_2CH_2$—,

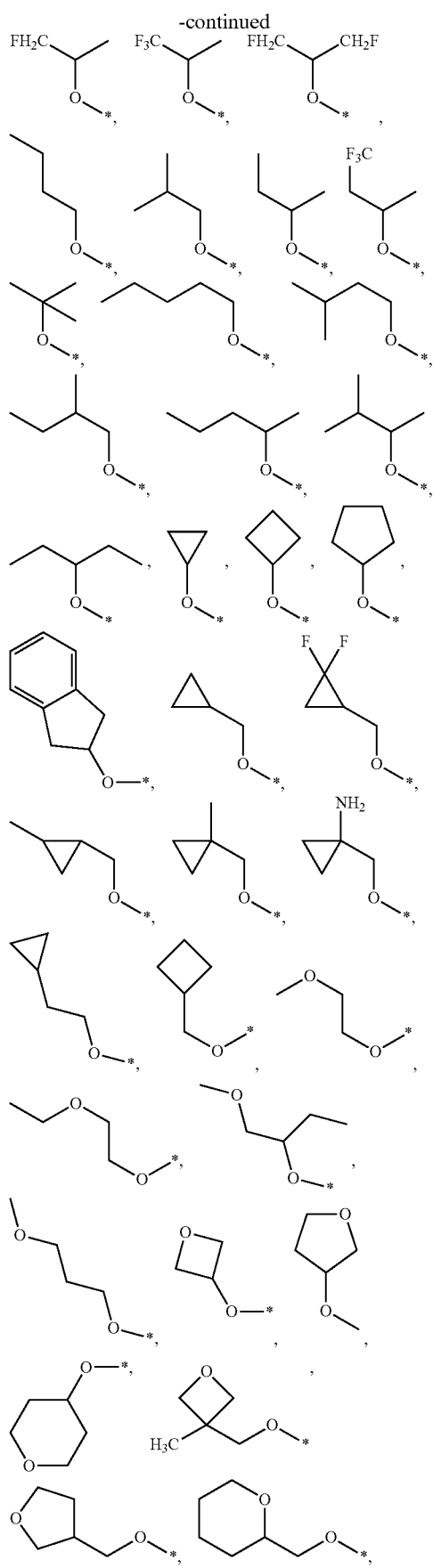
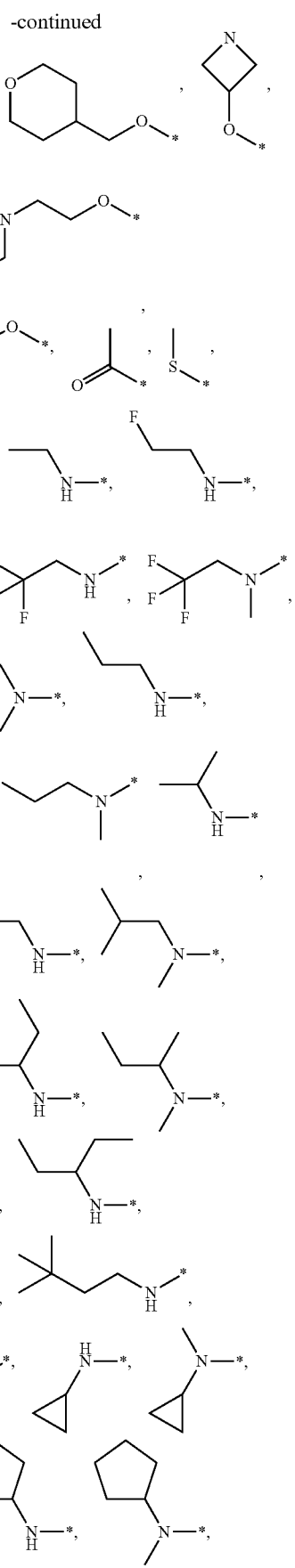

21
-continued
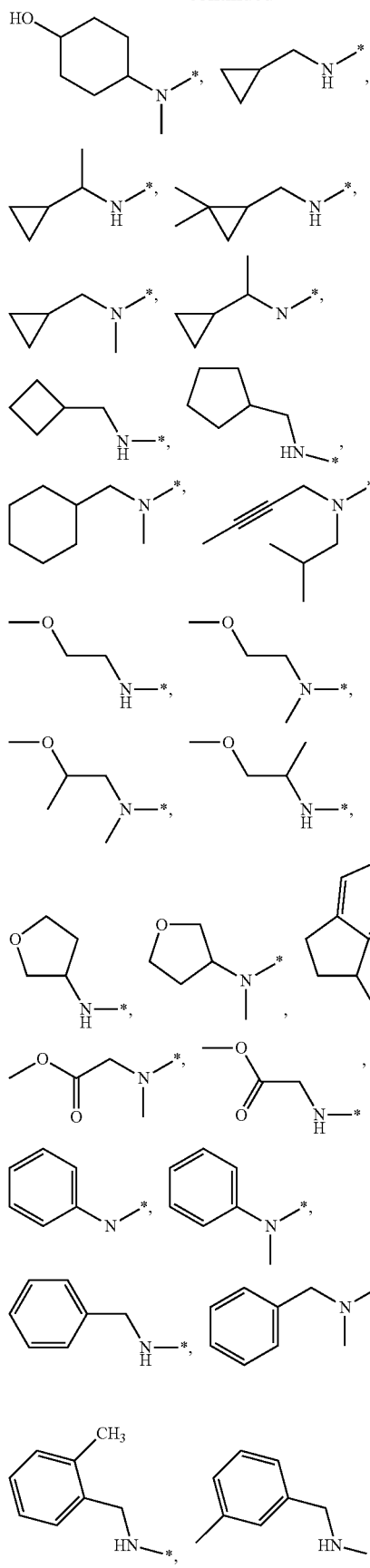
22
-continued
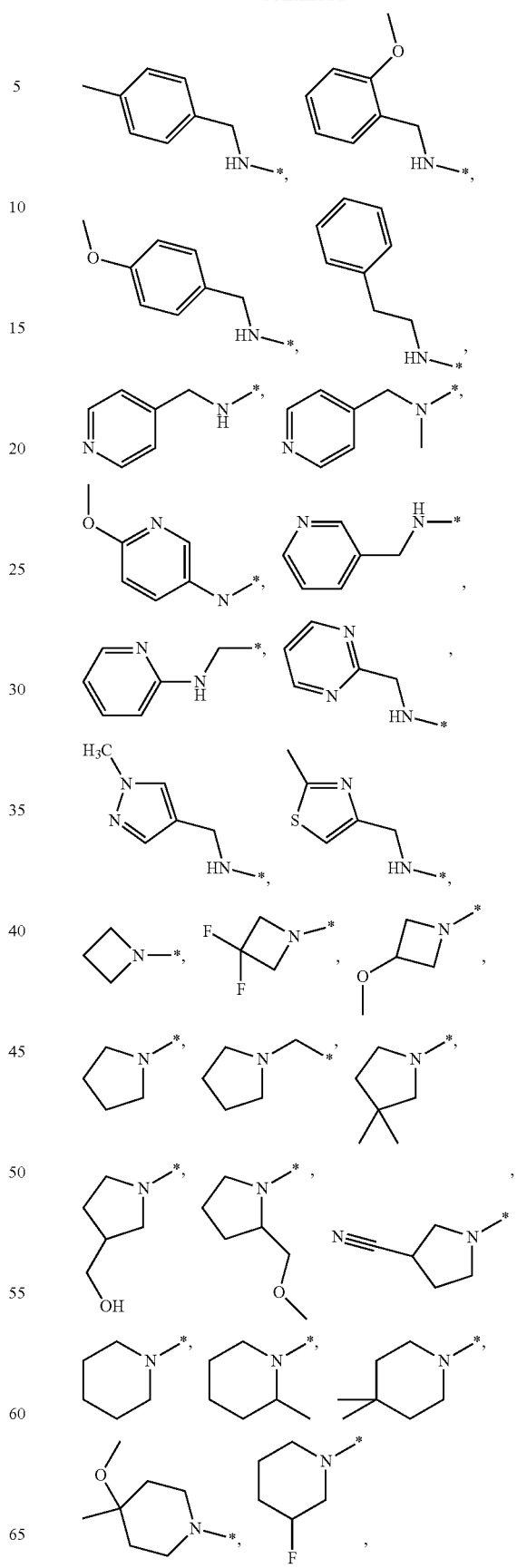

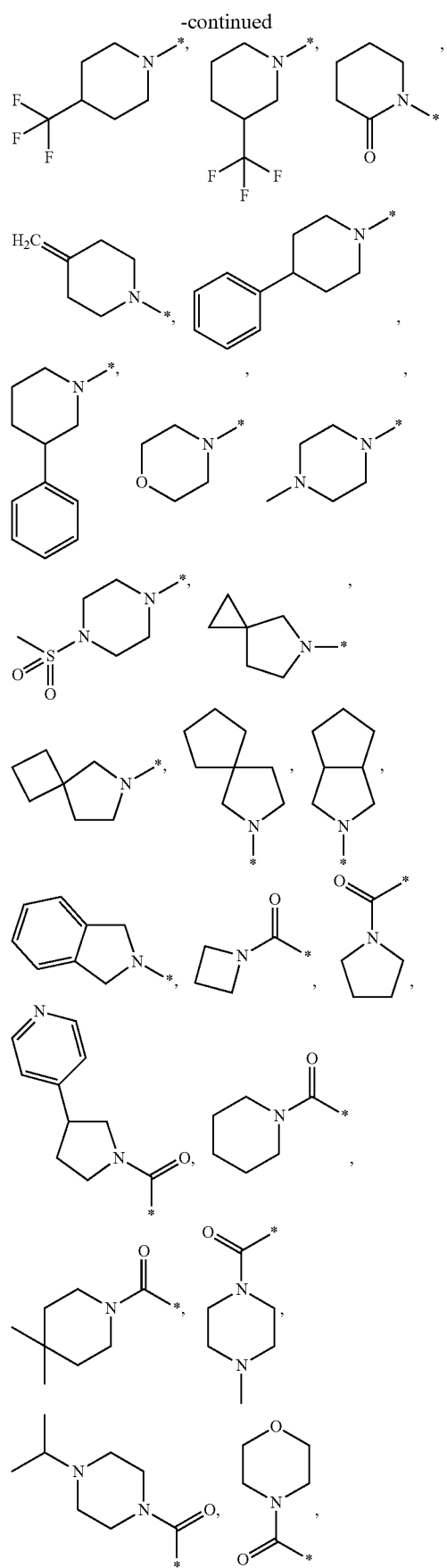
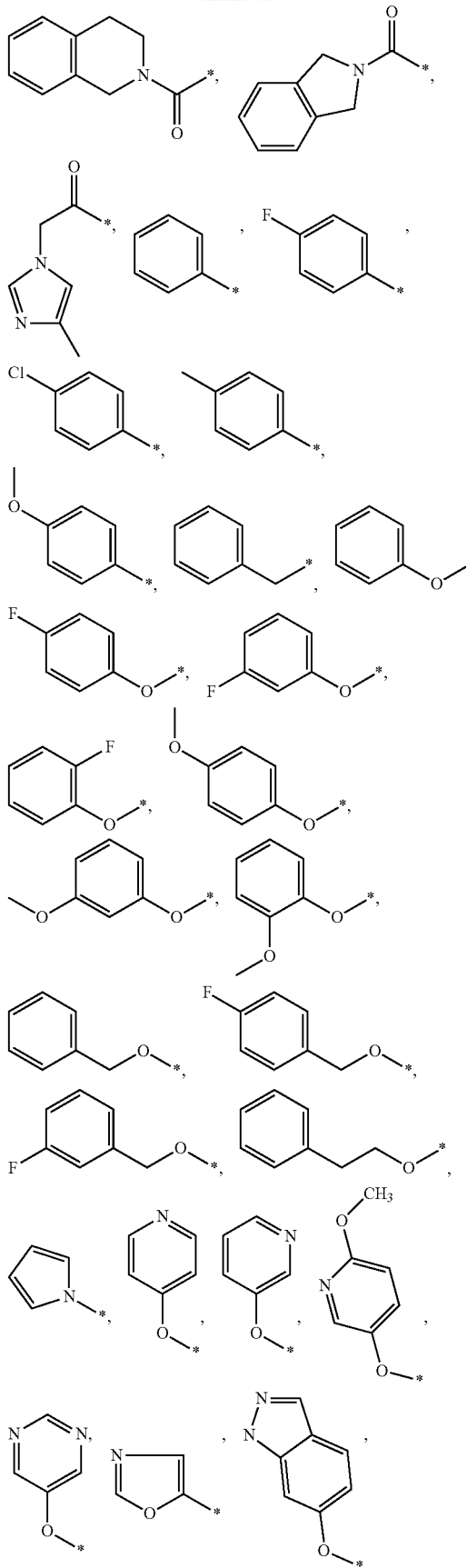

-continued

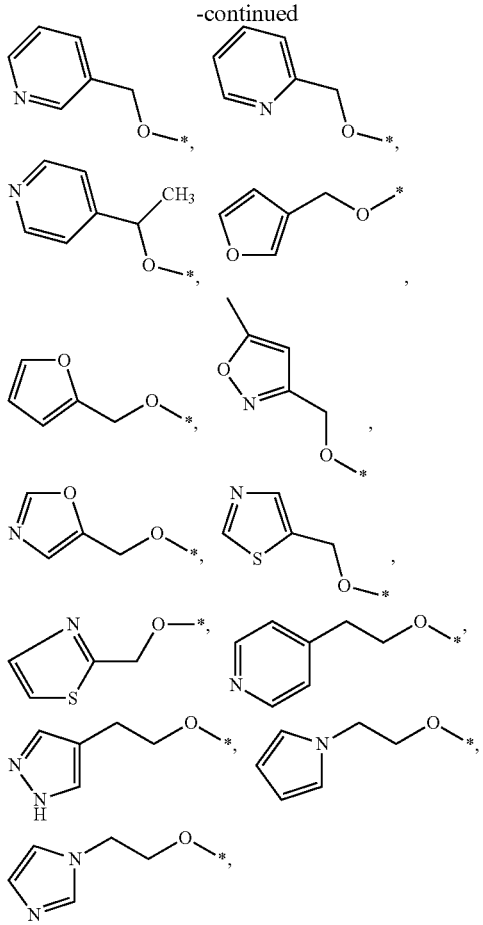

wherein each alkyl group and each cycloalkyl and heterocyclyl ring may be optionally substituted with one or more F atoms; and wherein each phenyl and heteroaryl ring may be optionally substituted with one or more substituents L.

$R^A$-G7:

In another preferred embodiment the group $R^A$ is selected from the group $R^A$-G7 consisting of

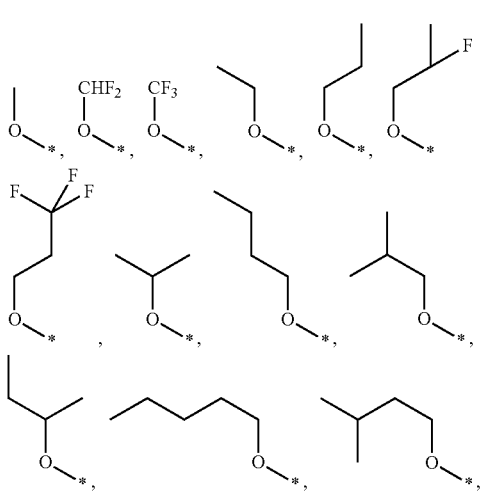

-continued

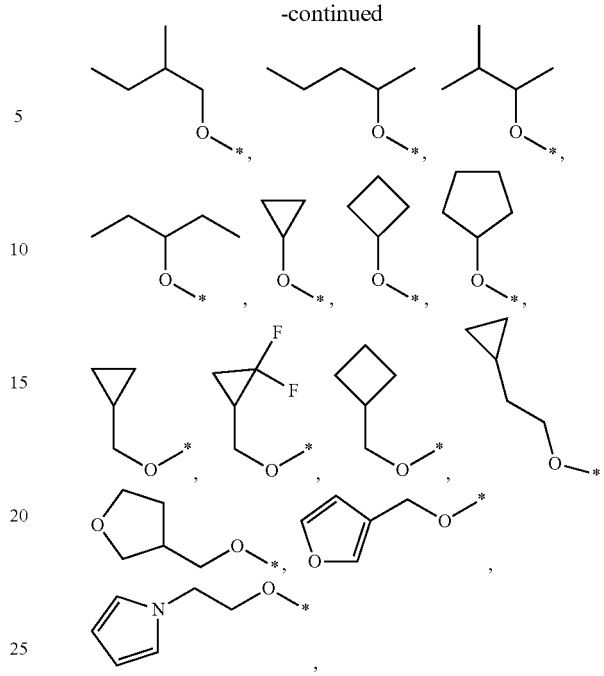

wherein each alkyl or cycloalkyl group may optionally be substituted with one or more F atoms.

$R^C$ $R^C$-G1:

The group $R^C$ is preferably selected from the group $R^C$-G1 as defined hereinbefore and hereinafter.

$R^C$-G2:

In another embodiment the group $R^C$ is selected from the group $R^C$-G2 consisting of F, Cl, Br, CN, OH, $C_{1-4}$-alkyl-O—, $C_{3-6}$-cycloalkyl-O—, $C_{3-6}$-cycloalkyl-$CH_2$—O—, $H_2N$—, ($C_{1-3}$-alkyl)NH—, ($C_{1-3}$-alkyl)$_2$N—, $C_{1-3}$-alkyl-C(=O)—, $C_{1-3}$-alkyl-S(=O)$_2$—, HO—C(=O)—, $C_{1-4}$-alkyl-O—C(=O)— and $H_2N$—C(=O)—, wherein each alkyl or cycloalkyl may be optionally substituted with one or more substituents selected from F and OH.

$R^C$-G3:

In another embodiment the group $R^C$ is selected from the group $R^C$-G3 consisting of F, Cl, Br, CN, OH, $C_{1-3}$-alkyl-O—, $C_{3-6}$-cycloalkyl-O—, $H_2N$—, ($C_{1-3}$-alkyl)NH—, ($C_{1-3}$-alkyl)$_2$N—, $C_{1-3}$-alkyl-C(=O)—, $C_{1-3}$-alkyl-S(=O)$_2$—, HO—C(=O)— and $C_{1-3}$-alkyl-O—C(=O)—, wherein each alkyl may be optionally substituted with one or more F-atoms and/or may be substituted with OH.

$R^{N1}$ $R^{N1}$-G1:

The group $R^{N1}$ is preferably selected from the group $R^{N1}$-G1 as defined hereinbefore and hereinafter.

$R^{N1}$-G2:

In another embodiment the group $R^{N1}$ is selected from the group $R^{N1}$-G2 consisting of H, $C_{1-6}$-alkyl, $C_{3-10}$-carbocyclyl, $C_{3-10}$-carbocyclyl-$C_{1-3}$-alkyl, $C_{3-6}$-alkynyl, heterocyclyl, heterocyclyl-$C_{1-3}$-alkyl, phenyl, phenyl-$C_{1-3}$-alkyl, pyridyl, pyridyl-$C_{1-3}$-alkyl and oxazolyl-$C_{1-3}$-alkyl;

wherein carbocyclyl is defined as hereinbefore and hereinafter, or each carbocyclyl is preferably selected from $C_{3-7}$-cycloalkyl, indanyl and tetrahydrofuranyl; and wherein heterocyclyl is defined as hereinbefore and hereinafter, or each heterocyclyl is preferably selected from tetrahydrofuranyl, tetrahydropyranyl, pyrrolidinyl, piperidinyl, piperazinyl and morpholinyl; and wherein heteroaryl is defined as hereinbefore and hereinafter, or heteroaryl preferably denotes pyridyl, pyrazolyl and oxazolyl; and wherein each carbocyclyl and heterocyclyl, may be optionally substituted with one or more $C_{1-4}$-alkyl; and wherein each alkyl, carbocyclyl, heterocyclyl, including piperazinyl and morpholinyl, may be optionally substituted with one or more substituents selected from F; and wherein each alkyl, carbocyclyl, heterocyclyl, including piperazinyl and morpholinyl, may be optionally substituted with a substituent selected from OH, $C_{1-3}$-alkyl-O—, $H_2N$—, HO—C(=O)— and $C_{1-4}$-alkyl-O—C(=O)—; and wherein each phenyl and heteroaryl may be optionally substituted with one or more substituents L.

With regard to an alkenyl or alkynyl group, for example $R^{N1}$, attached to the N-atom of an amino-group it is to be understood that the double or triple bond is preferably not conjugated with the N-atom.

$R^{N1}$-G3:

In another embodiment the group $R^{N1}$ is selected from the group $R^{N1}$-G3 consisting of H, $C_{1-6}$-alkyl, $C_{3-6}$-cycloalkyl, $C_{3-6}$-cycloalkyl-CH$_2$—, heterocyclyl, heterocyclyl-CH$_2$—, phenyl, phenyl-CH$_2$—, pyridyl, pyridyl-CH$_2$—, pyrazolyl-CH$_2$— and oxazolyl-$C_{1-3}$-alkyl;

wherein heterocyclyl is defined as hereinbefore and hereinafter, or each heterocyclyl is preferably selected from tetrahydrofuranyl, tetrahydropyranyl, pyrrolidinyl and piperidinyl; and wherein each cycloalkyl and heterocyclyl may be optionally substituted with one or more $C_{1-4}$-alkyl; and wherein each alkyl, cycloalkyl and heterocyclyl may be optionally substituted with one or more substituents selected from F; and wherein each alkyl, cycloalkyl and heterocyclyl may be optionally substituted with a substituent selected from OH, $C_{1-3}$-alkyl-O—, $H_2N$—, HO—C(=O)— and $C_{1-4}$-alkyl-O—C(=O)—; and wherein each phenyl and heteroaryl, including pyridyl, pyrazolyl and oxazolyl, may be optionally substituted with one or more substituents L.

With regard to an alkenyl or alkynyl group, for example $R^{N1}$, attached to the N-atom of an amino-group it is to be understood that the double or triple bond is preferably not conjugated with the N-atom.

$R^{N2}$:

$R^{N2}$-G1:

The group $R^{N2}$ is preferably selected from the group $R^{N2}$-G1 as defined hereinbefore and hereinafter.

$R^{N2}$-G2:

In another embodiment the group $R^{N2}$ is selected from the group $R^{N2}$-G2 consisting of H and $C_{1-4}$-alkyl.

$R^{Alk}$:

$R^{Alk}$-G1:

The group $R^{Alk}$ is preferably selected from the group $R^{Alk}$-G1 as defined hereinbefore and hereinafter.

$R^{Alk}$-G2:

In another embodiment the group $R^{Alk}$ is selected from the group $R^{Alk}$-G2 consisting of H and $C_{1-3}$-alkyl which may be substituted with one or more F atoms.

$Ar^2$:

$Ar^2$-G1:

The group $Ar^2$ is preferably selected from the group $Ar^2$-G1 as defined hereinbefore and hereinafter.

$Ar^2$-G2:

In another embodiment the group $Ar^2$ is selected from the group $Ar^2$-G2 consisting of phenyl, pyridyl, pyrimidinyl, pyridazinyl, pyrazinyl, furanyl, thienyl, pyrrolyl, imidazolyl, triazolyl, oxazolyl, isoxazolyl, pyrazolyl and thiazolyl, wherein all of the before mentioned groups may be optionally substituted with one or more substituents L.

$Ar^2$-G3:

In another embodiment the group $Ar^2$ is selected from the group $Ar^2$-G3 consisting of phenyl and pyridyl, wherein all of the before mentioned groups may be optionally substituted with one or more substituents L.

$Ar^2$-G4:

In another embodiment the group $Ar^2$ is selected from the group $Ar^2$-G4 consisting of:

wherein the before mentioned group may be optionally substituted with one or more substituents L.

L:

L-G1:

The group L is preferably selected from the group L-G1 as defined hereinbefore and hereinafter.

L-G2:

In another embodiment the group L is selected from the group L-G2 consisting of F, Cl, Br, CN, OH, $C_{1-3}$-alkyl-, $C_{1-3}$-alkyl-O—, $C_{1-3}$-alkyl-S—, $H_2N$—, ($C_{1-3}$-alkyl)NH—, ($C_{1-3}$-alkyl)$_2$N— and heterocyclyl;

wherein each alkyl may be optionally substituted with one or more F-atoms and/or a substituent selected from OH, $C_{1-3}$-alkyl-O— and CN; and wherein heterocyclyl is defined as hereinbefore and hereinafter, or heterocyclyl preferably denotes a $C_{3-6}$-cycloalkyl ring wherein one or two —CH$_2$-groups are replaced by a group selected from —O—, —NH—, —N($C_{1-3}$-alkyl)-; and wherein two substituents L attached to an aryl or heteroaryl group may be linked to each other and form a $C_{2-5}$-alkylene bridging group in which 1 or 2 —CH$_2$-groups may be replaced by a group independently of each other selected from O, NH and N($C_{1-4}$-alkyl)-, wherein the $C_{2-5}$-alkylene bridging group is optionally be substituted by 1 or 2 $C_{1-3}$-alkyl groups.

L-G3:

In another embodiment the group L is selected from the group L-G3 consisting of F, Cl, CN, OH, $C_{1-3}$-alkyl-, $C_{1-3}$-alkyl-O—, $C_{1-3}$-alkyl-S—, $H_2N$—, ($C_{1-3}$-alkyl)NH—, ($C_{1-3}$-alkyl)$_2$N— and heterocyclyl;

wherein each alkyl may be optionally substituted with one or more F-atoms and/or a substituent selected from OH, $CH_3$—O— and CN; and wherein heterocyclyl is defined as hereinbefore and hereinafter or heterocyclyl preferably denotes a $C_{3-6}$-cycloalkyl ring wherein one or two —CH$_2$-groups are replaced by a group selected from —O—, —NH—, —N($C_{1-3}$-alkyl)-; and wherein two substituents L attached to adjacent C-atoms of an aryl or heteroaryl group may be linked to each other and form a —CH$_2$—CH$_2$—O—, —O—CH$_2$—CH$_2$—O— or —O—CH$_2$—O— bridging group which is optionally substituted by 1 or 2 $CH_3$— groups.

X:

X-G1:

The group X is preferably selected from the group X-G1 as defined hereinbefore and hereinafter, in particular from a group consisting of a straight chain $C_{1-3}$-alkylene group which may be optionally substituted with 1, 2 or 3 groups selected from $C_{1-3}$-alkyl and $C_{1-3}$-alkyl-O—$C_{1-3}$-alkyl; even more preferably optionally substituted with 1 or 2 groups independently selected from methyl, ethyl or methoxymethyl; and wherein two alkyl substituents may be connected with each other and together form a $C_{1-5}$-alkylene bridging group in which 1 or 2 —$CH_2$-groups may be replaced by O, S, NH or N($C_{1-4}$-alkyl)-, wherein the $C_{1-5}$-alkylene bridging group may optionally be substituted by one or two $C_{1-3}$-alkyl groups.

X-G2:

In another embodiment the group X is selected from the group X-G2 consisting of:

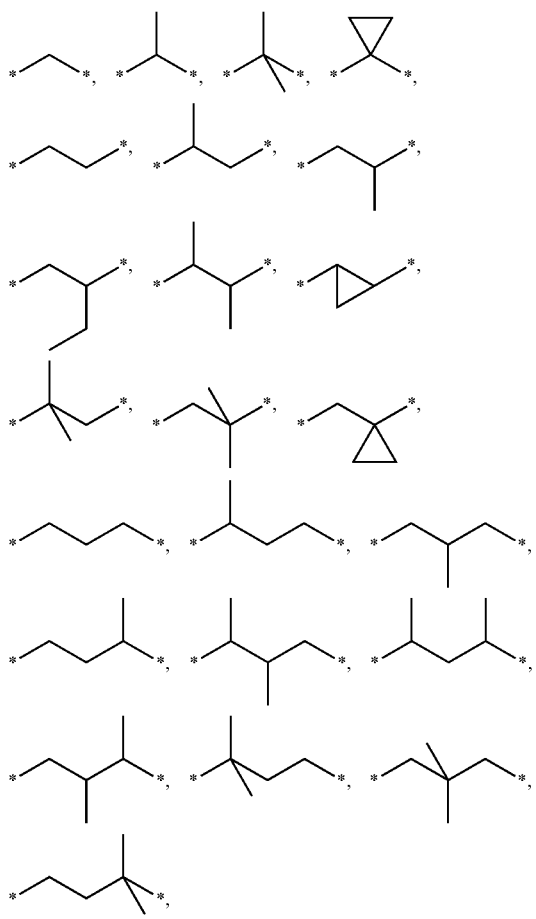

even more preferably selected from the group X-G3 consisting of:

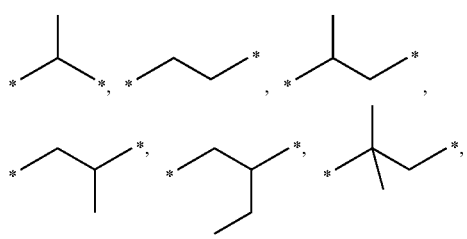

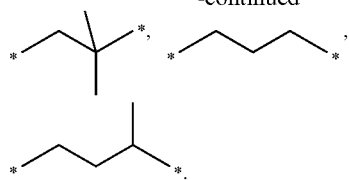

X-GC1:

According an embodiment X-GC1 the group X is —$CH_2$— which may be optionally substituted with one or two $C_{1-3}$-alkyl groups, preferably with one or two groups independently selected from methyl and ethyl, and wherein two alkyl substituents may be connected with each other and together form a $C_{2-5}$-alkylene bridging group in which 1 or 2 —$CH_2$-groups may be replaced by O, S, NH or N($C_{1-4}$-alkyl)-, wherein the $C_{1-5}$-alkylene bridging group may optionally be substituted by one or two $C_{1-3}$-alkyl groups.

Examples of this embodiment are:

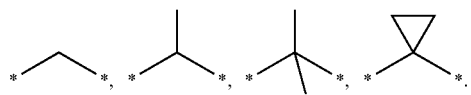

X-GC1a:

According an embodiment X-GC1a the group X is

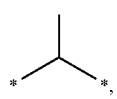

embracing

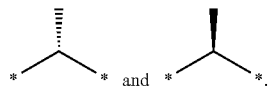

X-GC2:

According to another embodiment X-GC2 the group X is —$CH_2$—$CH_2$— which may be optionally substituted with one or more $C_{1-3}$-alkyl groups, preferably with one or two groups independently selected from methyl and ethyl, and wherein two alkyl substituents may be connected with each other and together form a $C_{1-5}$-alkylene bridging group in which 1 or 2 —$CH_2$-groups may be replaced by O, S, NH or N($C_{1-4}$-alkyl)-, wherein the $C_{1-5}$-alkylene bridging group may optionally be substituted by one or two $C_{1-3}$-alkyl groups.

Examples of this embodiment are:

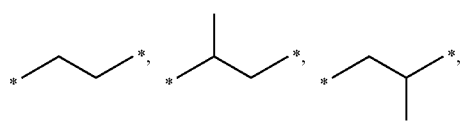

-continued

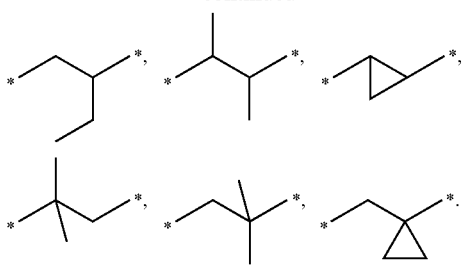

Preferred examples are:

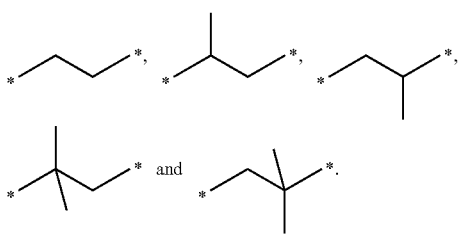

X-GC2a:

According an embodiment X-GC2a the group X is

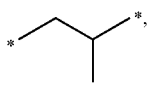

embracing

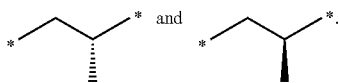

X-GC3:

According another embodiment X-GC3 the group X is —CH$_2$—CH$_2$—CH$_2$— which may be optionally substituted with one or more C$_{1-3}$-alkyl groups, preferably with one or two groups independently selected from methyl and ethyl, and wherein two alkyl substituents may be connected with each other and together form a C$_{1-5}$-alkylene bridging group in which 1 or 2 —CH$_2$-groups may be replaced by O, S, NH or N(C$_{1-4}$-alkyl)-, wherein the C$_{1-5}$-alkylene bridging group may optionally be substituted by one or two C$_{1-3}$-alkyl groups.

Examples of this embodiment are:

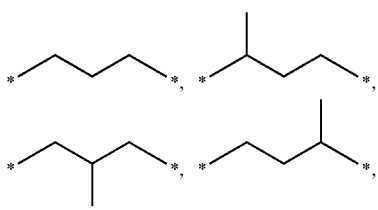

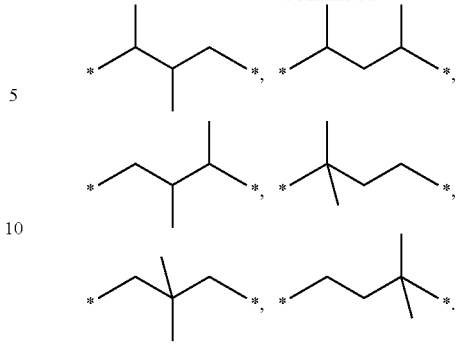

Y:
Y-G1:
The group Y is preferably selected from the group Y-G1 as defined hereinbefore and hereinafter.
Y-G2:
In another embodiment the group Y is selected from the group Y-G2 consisting of —C(=O)—.
Y-G3:
In another embodiment the group Y is selected from the group Y-G3 consisting of —S(=O)$_2$—.
T$^1$:
T$^1$-G1:
The group T is preferably selected from the group T-G1 as defined hereinbefore and hereinafter.
T$^1$-G1:
In another embodiment the group T$^1$ is selected from the group T$^1$-G2 consisting of H, C$_{1-6}$-alkyl, C$_{2-6}$-alkenyl, C$_{2-6}$-alkynyl, C$_{3-7}$-cycloalkyl, heterocyclyl, heterocyclyl-C$_{1-3}$-alkyl, phenyl, phenyl-C$_{1-3}$-alkyl, heteroaryl and heteroaryl-C$_{1-3}$-alkyl,
wherein in each cycloalkyl and heterocyclyl a —CH$_2$-group may optionally be replaced by —C(=O)—; and
wherein each cycloalkyl and heterocyclyl may be optionally substituted with one or more C$_{1-4}$-alkyl, which may be optionally substituted with one or more substituents R$^C$: and
wherein each alkyl, alkenyl, alkynyl, cycloalkyl and heterocyclyl may be optionally substituted with one or more substituents R$^C$; and
wherein R$^C$ is selected from the group consisting of R$^C$-G1, R$^C$-G2 or R$^C$-G3 as defined hereinbefore and hereinafter,
wherein heterocyclyl is defined as hereinbefore and hereinafter; preferably heterocyclyl is azetidinyl, pyrrolidinyl, piperidinyl, oxetanyl, tetrahydrofuranyl or tetrahydropyranyl; and
wherein heteroaryl is selected from the group consisting of pyridyl, pyrimidinyl, pyridazinyl, pyrazinyl, furanyl, thienyl, pyrrolyl, imidazolyl, pyrazolyl, triazolyl, oxazolyl, isoxazolyl, thiazolyl, oxadiazolyl, thiadiazolyl; and
wherein each phenyl and heteroaryl group may be optionally substituted with one or more substituents L.
T$^1$-G3:
In another embodiment the group T$^1$ is selected from the group T$^1$-G3 consisting of H, C$_{1-6}$-alkyl, C$_{3-7}$-cycloalkyl, C$_{3-7}$-cycloalkyl-C$_{1-3}$-alkyl, phenyl, phenyl-C$_{1-3}$-alkyl, heteroaryl and heteroaryl-C$_{1-3}$-alkyl,
wherein each cycloalkyl may be optionally substituted with one or more C$_{1-4}$-alkyl, which may be optionally substituted with one or more substituents R$^C$: and
wherein each alkyl and cycloalkyl may be optionally substituted with one or more substituents R$^C$; and wherein R^C is selected from the group consisting of R^C-G1, R^C-G2 or R^C-G3 as defined hereinbefore and hereinafter, in particular R^C is selected from the group consisting of F, CN, $C_{1-4}$-alkyl-O—, $C_{1-4}$-alkyl-O—C(=O)—, $H_2N$—C(=O)—, $(C_{1-3}$-alkyl)NH—C(=O)—, $(C_{1-3}$-alkyl)$_2$N—C(=O)—, wherein heteroaryl is selected from the group consisting of pyridyl, pyrimidinyl, pyridazinyl, pyrazinyl, furanyl, thienyl, pyrrolyl, imidazolyl, pyrazolyl, triazolyl, oxazolyl, isoxazolyl, thiazolyl, oxadiazolyl, thiadiazolyl; and wherein each phenyl and heteroaryl group may be optionally substituted with one or more substituents L.

$T^1$-G4:

In another embodiment the group $T^1$ is selected from the group $T^1$-G4 consisting of H, $H_3C$—, $H_5C_2$—, NC—$CH_2$—,

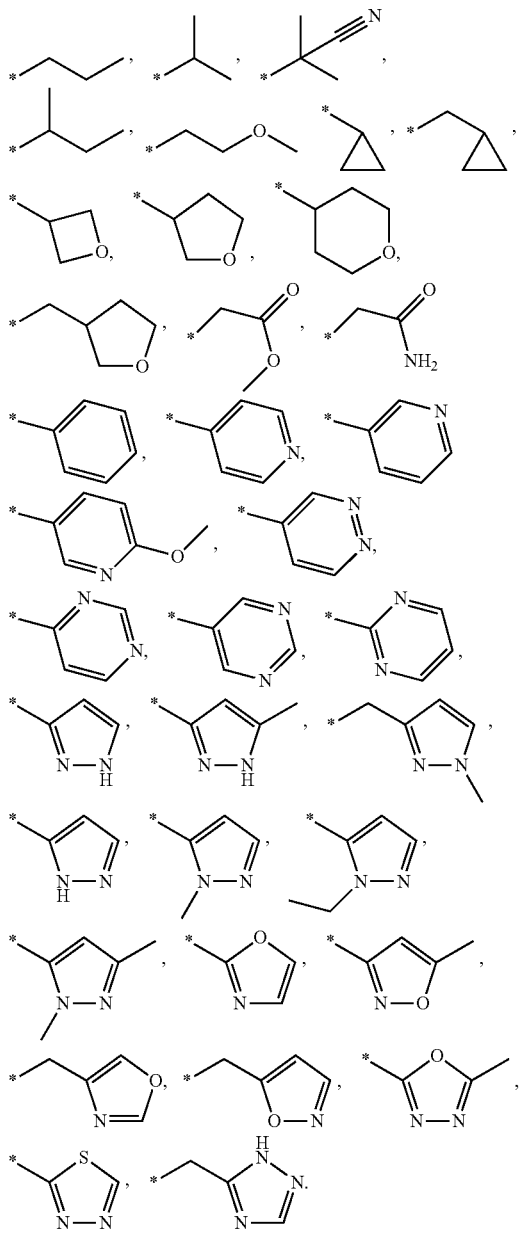

$T^1$-G5:

In another embodiment the group $T^1$ is selected from the group $T^1$-G5 consisting of H, $H_3C$—, $H_5C_2$—,

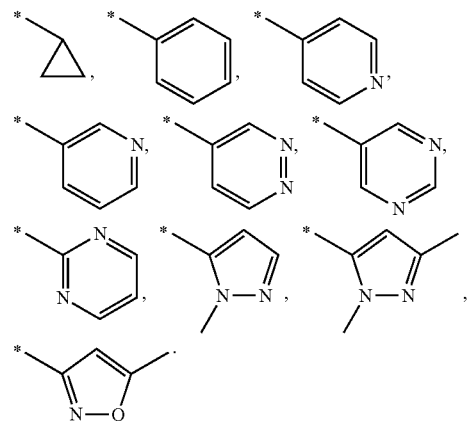

$T^2$:

$T^2$-G1:

The group $T^2$ is preferably selected from the group $T^2$-G1 as defined hereinbefore and hereinafter.

$T^2$-G2:

In another embodiment the group $T^2$ is selected from the group $T^2$-G2 consisting of H, methyl, ethyl, n-propyl, isopropyl.

$T^2$-G3:

In another embodiment the group $T^2$ is selected from the group $T^2$-G3 consisting of H, methyl.

$T^1$-$T^2$:

$T^1$-$T^2$-G1:

In an embodiment the groups $T^1$ and $T^2$ are connected with each other and together form a group which is preferably selected from the group $T^1$-$T^2$-G1 as defined hereinbefore and hereinafter.

$T^1$-$T^2$-G1:

In another embodiment the groups $T^1$ and $T^2$ are connected with each other such that the group $$\overset{*}{\underset{T^2}{N}}-T^1$$

is selected from the group $T^1$-$T^2$-G1 consisting of:

all of which may be optionally substituted with one or more substituents selected from F, Cl, Br, OH, CN, $C_{1-4}$-alkyl, $C_{3-6}$-cycloalkyl, $C_{3-6}$-cycloalkyl-$C_{1-3}$-alkyl, $C_{1-4}$-alkyl-O—, $C_{3-6}$-cycloalkyl-O—, $C_{3-6}$-cycloalkyl-$C_{1-3}$-alkyl-O—, $H_2N$—, $(C_{1-4}$-alkyl)NH—, $(C_{1-4}$-alkyl)$_2$N—, $C_{1-4}$-alkyl-C(=O)—, HO—C(=O)— and $C_{1-4}$-alkyl-O—C(=O)—, wherein each alkyl or cycloalkyl may be optionally substituted with one or more substituents selected from F, and wherein each alkyl or cycloalkyl may be optionally substituted with a substituent selected from Cl, Br, OH, CN, $C_{1-3}$-alkyl-O—, $C_{3-6}$-cycloalkyl-O—, $C_{3-6}$-cycloalkyl-$C_{1-3}$-alkyl-O—, $H_2N$—, ($C_{1-3}$-alkyl)NH—, ($C_{1-3}$-alkyl)$_2$N—, $C_{1-4}$-alkyl-C(=O)—, $C_{1-4}$-alkyl-S(=O)$_2$—, HO—C(=O)— and $C_{1-4}$-alkyl-O—C(=O)—.

which may be substituted with one or more F atoms and/or $C_{1-3}$-alkyl.

Examples of preferred subgeneric embodiments according to the present invention are set forth in the following table, wherein each substituent group of each embodiment is defined according to the definitions set forth hereinbefore and wherein all other substituents of the formula (I) are defined according to the definitions set forth hereinbefore:

| Embodiment | $Ar^1$ | $R^A$ | $Ar^2$ | X | Y | $T^1$ and $T^2$ |
|---|---|---|---|---|---|---|
| E-1 | $Ar^1$-G1 | $R^A$-G1 | $Ar^2$-G1 | X-G1 | Y-G1 | $T^1$-G1, $T^2$-G1 or $T^1$-$T^2$-G1 |
| E-2 | $Ar^1$-G2 | $R^A$-G2 | $Ar^2$-G2 | X-G1 | Y-G1 | $T^1$-G2, $T^2$-G2 or $T^1$-$T^2$-G2 |
| E-3 | $Ar^1$-G3 | $R^A$-G3 | $Ar^2$-G2 | X-G1 | Y-G1 | $T^1$-G2, $T^2$-G2 or $T^1$-$T^2$-G2 |
| E-4 | $Ar^1$-G4 | $R^A$-G4 | $Ar^2$-G3 | X-G1 | Y-G1 | $T^1$-G3, $T^2$-G2 |
| E-5 | $Ar^1$-G4 | $R^A$-G4 | $Ar^2$-G3 | X-G1 | Y-G1 | $T^1$-$T^2$-G2 |
| E-6 | $Ar^1$-G6 | $R^A$-G4 | $Ar^2$-G3 | X-G1 | Y-G1 | $T^1$-G3, $T^2$-G2 or $T^1$-$T^2$-G2 |
| E-7 | $Ar^1$-G7 | $R^A$-G4 | $Ar^2$-G3 | X-G1 | Y-G1 | $T^1$-G3, $T^2$-G2 or $T^1$-$T^2$-G2 |
| E-8 | $Ar^1$-G6 | $R^A$-G5 | $Ar^2$-G4 | X-G1 | Y-G1 | $T^1$-G3, $T^2$-G2 or $T^1$-$T^2$-G2 |
| E-9 | $Ar^1$-G7 | $R^A$-G5 | $Ar^2$-G4 | X-G1 | Y-G1 | $T^1$-G3, $T^2$-G2 or $T^1$-$T^2$-G2 |
| E-10 | $Ar^1$-G5 | $R^A$-G6 | $Ar^2$-G3 | X-G2 | Y-G1 | $T^1$-G3, $T^2$-G2 or $T^1$-$T^2$-G2 |
| E-11 | $Ar^1$-G1 | $R^A$-G1 | $Ar^2$-G1 | X-GC1 | —C(=O)— | $T^1$-G1, $T^2$-G1 or $T^1$-$T^2$-G1 |
| E-12 | $Ar^1$-G1 | $R^A$-G1 | $Ar^2$-G1 | X-GC2 | —C(=O) | $T^1$-G1, $T^2$-G1 or $T^1$-$T^2$-G1 |
| E-13 | $Ar^1$-G1 | $R^A$-G1 | $Ar^2$-G1 | X-GC3 | —C(=O) | $T^1$-G1, $T^2$-G1 or $T^1$-$T^2$-G2 |
| E-14 | $Ar^1$-G6 | $R^A$-G4 | $Ar^2$-G3 | X-GC1 | —C(=O)— | $T^1$-G3, $T^2$-G2 or $T^1$-$T^2$-G2 |
| E-15 | $Ar^1$-G6 | $R^A$-G4 | $Ar^2$-G3 | X-GC2 | —C(=O) | $T^1$-G3, $T^2$-G2 or $T^1$-$T^2$-G2 |
| E-16 | $Ar^1$-G6 | $R^A$-G4 | $Ar^2$-G3 | X-GC3 | —C(=O) | $T^1$-G3, $T^2$-G2 or $T^1$-$T^2$-G2 |
| E-17 | $Ar^1$-G7 | $R^A$-G4 | $Ar^2$-G3 | X-GC1 | —C(=O)— | $T^1$-G3, $T^2$-G2 or $T^1$-$T^2$-G2 |
| E-18 | $Ar^1$-G7 | $R^A$-G4 | $Ar^2$-G3 | X-GC2 | —C(=O) | $T^1$-G3, $T^2$-G2 or $T^1$-$T^2$-G2 |
| E-19 | $Ar^1$-G7 | $R^A$-G4 | $Ar^2$-G3 | X-GC3 | —C(=O) | $T^1$-G3, $T^2$-G2 or $T^1$-$T^2$-G2 |
| E-20 | $Ar^1$-G1 | $R^A$-G1 | $Ar^2$-G1 | X-G1 | —S(=O)$_2$— | $T^1$-G1, $T^2$-G1 or $T^1$-$T^2$-G1 |
| E-21 | $Ar^1$-G4 | $R^A$-G4 | $Ar^2$-G2 | X-GC1 | —S(=O)$_2$— | $T^1$-G3, $T^2$-G2 or $T^1$-$T^2$-G2 |
| E-22 | $Ar^1$-G4 | $R^A$-G4 | $Ar^2$-G2 | X-GC2 | —S(=O)$_2$— | $T^1$-G3, $T^2$-G2 or $T^1$-$T^2$-G2 |
| E-23 | $Ar^1$-G4 | $R^A$-G4 | $Ar^2$-G2 | X-GC3 | —S(=O)$_2$— | $T^1$-G3, $T^2$-G2 or $T^1$-$T^2$-G2 |

$T^1$-$T^2$-G3:

In another embodiment the groups $T^1$ and $T^2$ are connected with each other such that the group

is selected from the group $T^1$-$T^2$-G3 consisting of:

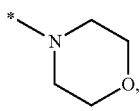

The following preferred embodiments of compounds of the formula (I) are described using generic formulas (I.1a) to (I.1c) and (I.1) to (I.5), wherein any tautomers and stereoisomers, solvates, hydrates and salts thereof, in particular the pharmaceutically acceptable salts thereof, are encompassed.

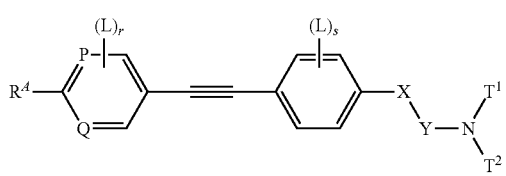

(I.1)

-continued

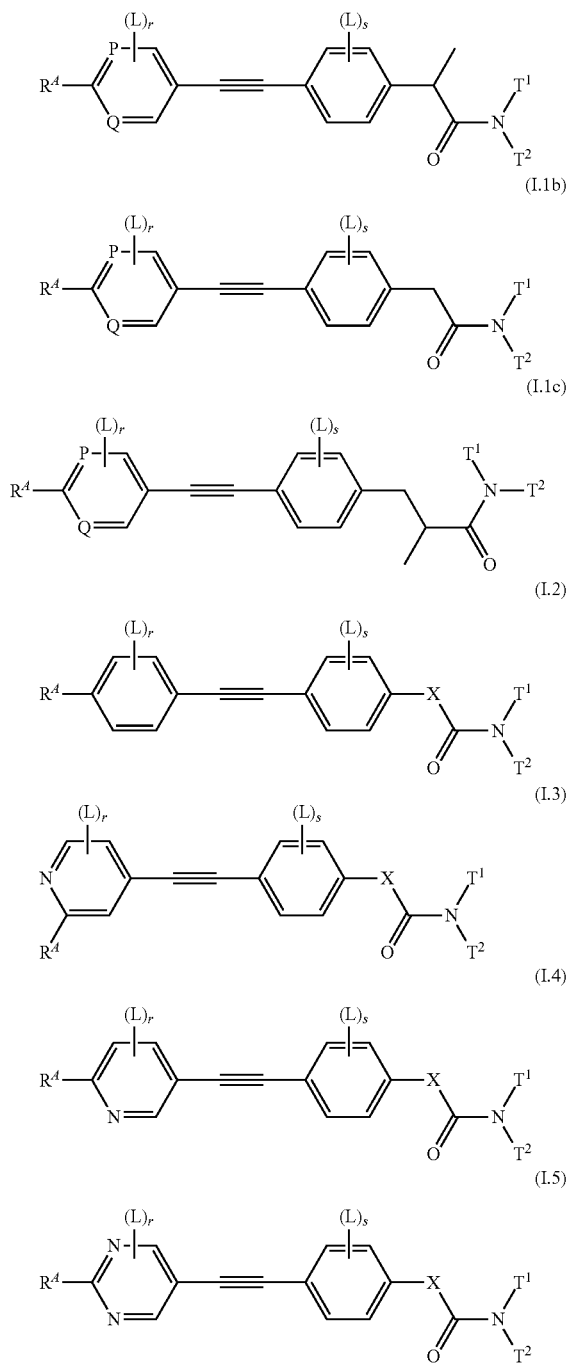

wherein in each of the above formulas (I.1a) to (I.1c) and (I.1) to (I.5), the groups $R^4$, L, X, $T^1$ and $T^2$ are defined as hereinbefore and hereinafter; and
P is N or CH, wherein CH may be optionally substituted by L as defined; and
Q is N or CH, wherein CH may be optionally substituted by L as defined; and
r is 0, 1 or 2; and
s is 0, 1 or 2.

Preferred embodiments of the above formulas (I.1a) to (I.1c) and (I.1) to (I.5) according to the present invention are set forth in the following table, wherein each group $R^4$, X, $T^1$, $T^2$, L of each embodiment is defined according to the definitions set forth hereinbefore and wherein all other substituents of the formula (I) are defined according to the definitions set forth hereinbefore and P, Q, r and s are defined as hereinbefore:

| Embodiment | Formula | $R^4$ | X | $T^1$ | $T^2$ | L |
|---|---|---|---|---|---|---|
| E-A | (I.1) | RA-G2 | X-G1 | T-G1 | T-G1 | L-G2 |
| E-B | (I.1) | RA-G4 | X-G2 | T-G3 | T-G2 | L-G2 |
| E-C | (I.1a) | RA-G2 | X-G1 | T-G1 | T-G1 | L-G2 |
| E-D | (I.1a) | RA-G4 | X-G2 | T-G3 | T-G2 | L-G2 |
| E-E | (I.2) | RA-G2 | X-G1 | T-G1 | T-G1 | L-G2 |
| E-F | (I.2) | RA-G4 | X-G2 | T-G3 | T-G2 | L-G2 |
| E-G | (I.3) | RA-G2 | X-G1 | T-G1 | T-G1 | L-G2 |
| E-H | (I.3) | RA-G4 | X-G2 | T-G3 | T-G2 | L-G2 |
| E-I | (I.4) | RA-G2 | X-G1 | T-G1 | T-G1 | L-G2 |
| E-J | (I.4) | RA-G4 | X-G2 | T-G3 | T-G2 | L-G2 |
| E-K | (I.5) | RA-G2 | X-G1 | T-G1 | T-G1 | L-G2 |
| E-L | (I.5) | RA-G4 | X-G2 | T-G3 | T-G2 | L-G2 | including any tautomers and stereoisomers, solvates, hydrates and salts thereof, in particular the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably the compounds are obtained analogously to the methods of preparation explained more fully hereinafter, in particular as described in the experimental section.

Compounds of the general formula (I) can be prepared by the following methods:

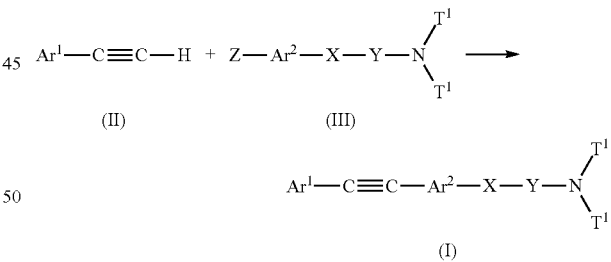

Compounds of general formula (I) may be prepared by palladium-mediated Sonogashira reactions of alkynes (II) with aryl halogenides or aryl triflates (III) wherein Z is a leaving group which for example denotes Cl, Br, I or OTf (triflate).

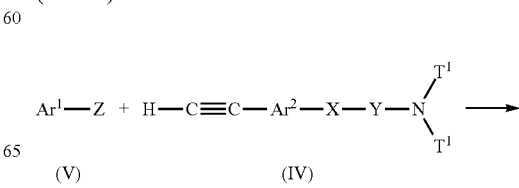

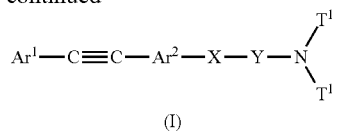

(I)

Compounds of general formula (I) may be prepared by palladium-mediated Sonogashira reactions of alkynes (IV) with aryl halogenides or aryl triflates (V) wherein Z is a leaving group which for example denotes Cl, Br, I or OTf (triflate).

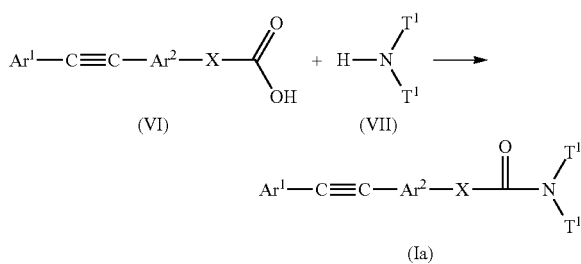

(Ia)

Compounds of general formula (Ia) may be prepared by amide coupling reactions of amines (VII) with carboxylic acids (VI) mediated by coupling reagents such as eg chloro-N,N,N',N'-tetramethylformamidinium hexafluorophosphate, TBTU, HOBt or HATU or by activation via acylhalide intermediates.

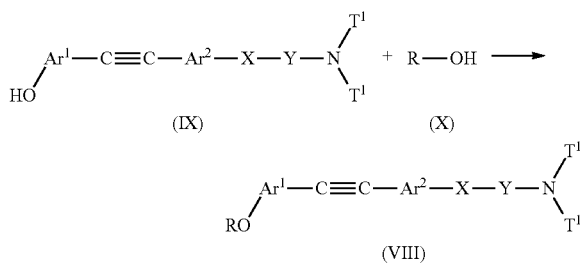

(VIII)

Compounds of general formula (VIII) may be prepared by Mitsunobu reactions of aromatic alcohols (IX) with alcohols (X) mediated by coupling reagents such as azodicarboxylates (e.g. DEAD, DIAD etc.) and phosphines (e.g. triphenylphosphine).

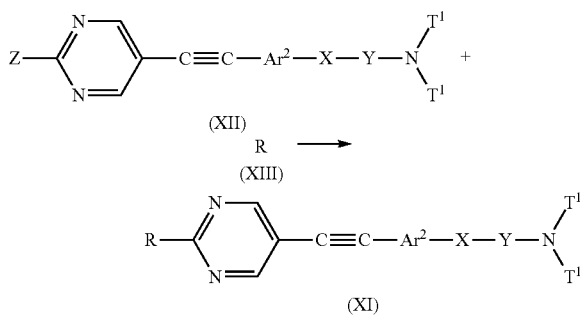

(XI)

Compounds of general formula (XI) may be prepared by nucleophilic aromatic substitution reactions (SNAr) of pyrimidines (XII) with nucleophiles R(XIII), wherein Z is a leaving group which for example denotes Cl, Br, I, S(=O)CH3 or triflate and wherein R is a nucleophile, such as for example an alcohol or an amine and wherein the reaction may be performed with other regioisomers of pyrimidine or other hetaryls also.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of the Acetyl-CoA carboxylases (ACC) enzyme(s) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached. For example, the term "3-carboxypropyl-group" represents the following substituent:

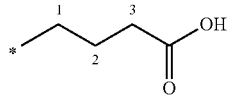

wherein the carboxy group is attached to the third carbon atom of the propyl group. The terms "1-methylpropyl-", "2,2-dimethylpropyl-" or "cyclopropylmethyl-" group represent the following groups:

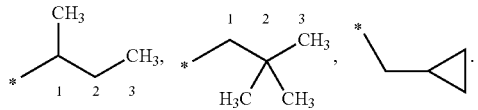

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. ...) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methyl nitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—

CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

The term "C$_{2-n}$-alkenyl", is used for a group as defined in the definition for "C$_{1-n}$-alkyl" with at least two carbon atoms, if at least two of those carbon atoms of said group are bonded to each other by a double bond. For example the term C$_{2-3}$-alkenyl includes —CH=CH$_2$, —CH=CH—CH$_3$, —CH$_2$—CH=CH$_2$.

The term "C$_{2-n}$-alkenylene" is used for a group as defined in the definition for "C$_{1-n}$-alkylene" with at least two carbon atoms, if at least two of those carbon atoms of said group are bonded to each other by a double bond. For example the term C$_{2-3}$-alkenylene includes —CH=CH—, —CH=CH—CH$_2$—, —CH$_2$—CH=CH—.

The term "C$_{2-n}$-alkynyl", is used for a group as defined in the definition for "C$_{1-n}$-alkyl" with at least two carbon atoms, if at least two of those carbon atoms of said group are bonded to each other by a triple bond. For example the term C$_{2-3}$-alkynyl includes —C≡CH, —CH$_2$—C≡CH.

The term "C$_{2-n}$-alkynylene" is used for a group as defined in the definition for "C$_{1-n}$-alkylene" with at least two carbon atoms, if at least two of those carbon atoms of said group are bonded to each other by a triple bond. For example the term C$_{2-3}$-alkynylene includes The term "C$_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term C$_{3-10}$-carbocyclyl includes C$_{3-10}$-cylcoalkyl, C$_{3-10}$-cycloalkenyl, octahydropentalenyl, octahydroindenyl, decahydronaphthyl, indanyl, tetrahydronaphthyl. Most preferably the term C$_{3-n}$-carbocyclyl denotes C$_{3-n}$-cylcoalkyl, in particular C$_{3-7}$-cycloalkyl.

The term "C$_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "C$_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term C$_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)$_r$ with r=0, 1 or 2 which in addition may have a carbonyl group. The term "heterocyclyl is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

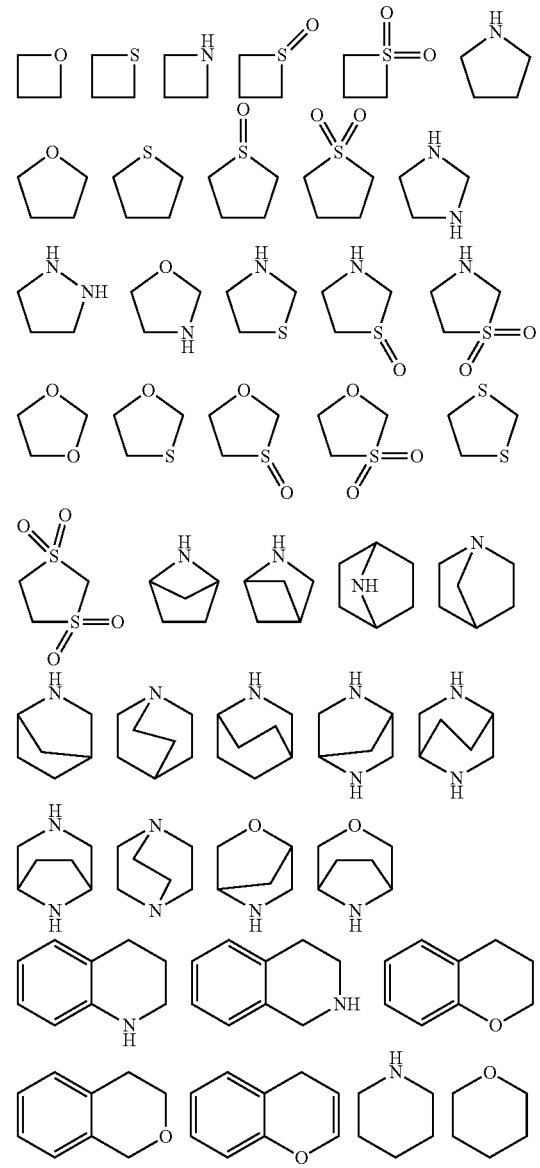

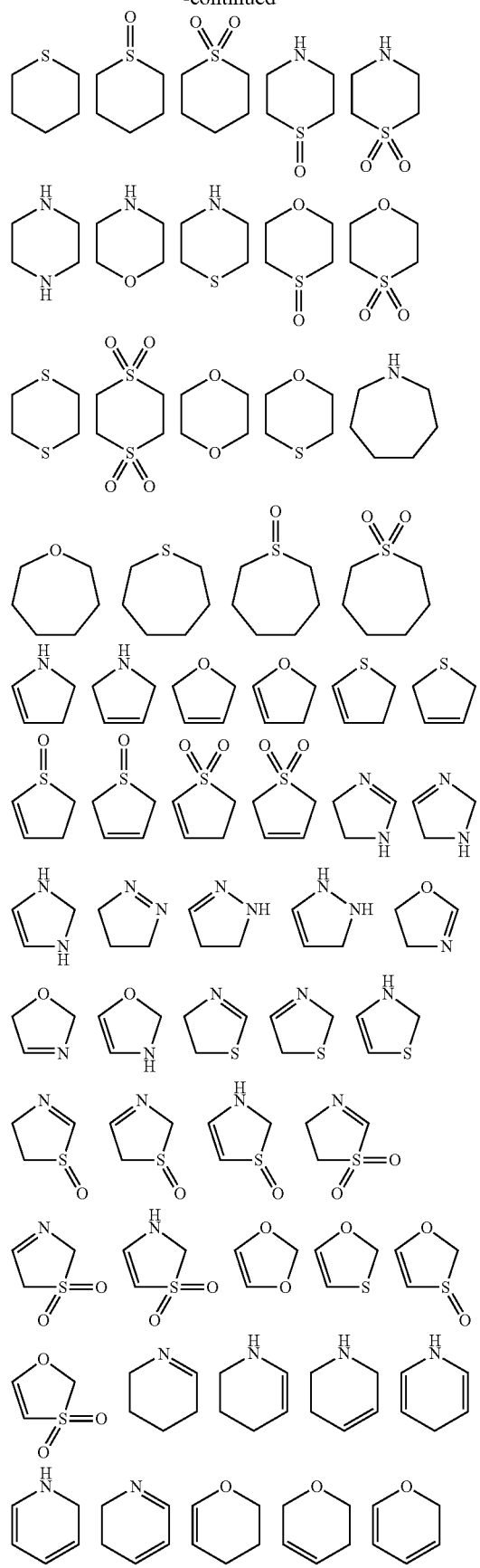
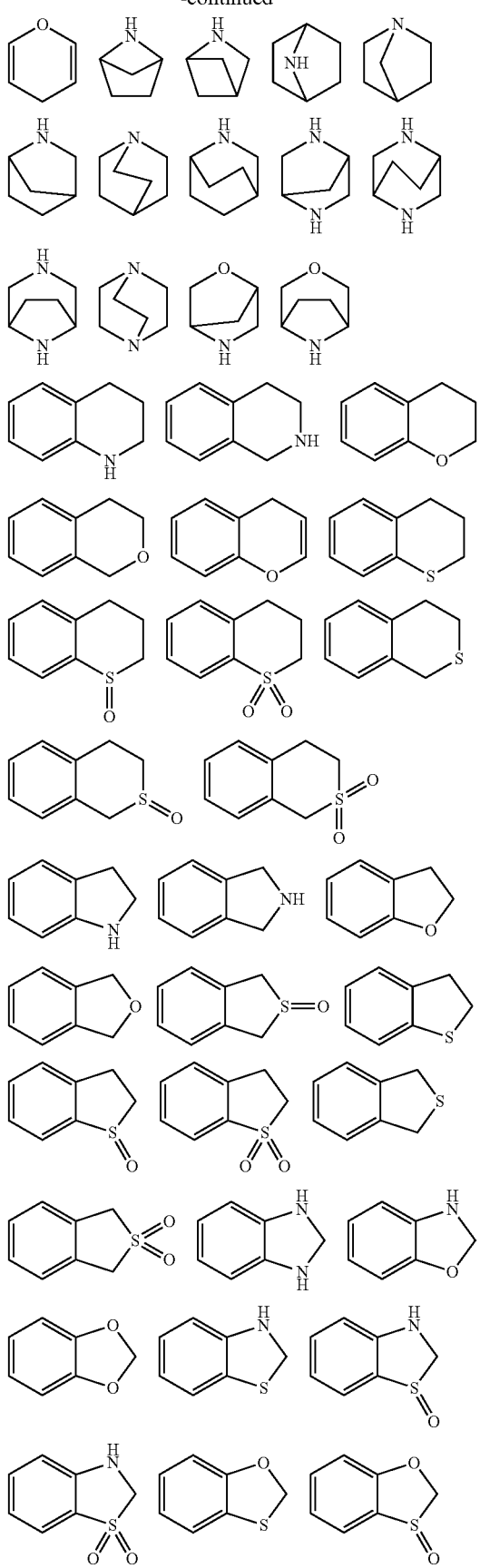

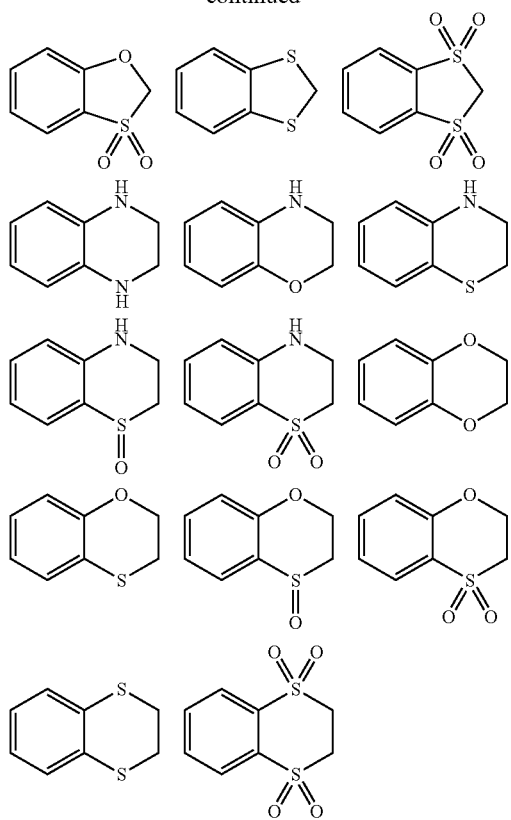

The term "heteroaryl" means a mono- or polycyclic, preferably mono- or bicyclic-ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

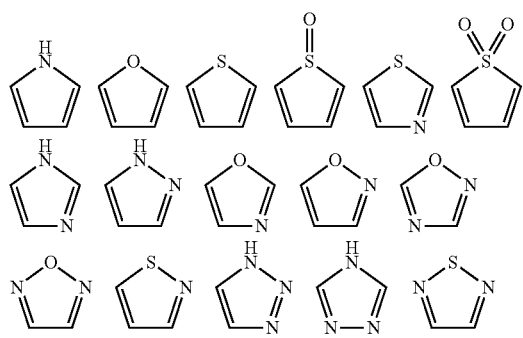

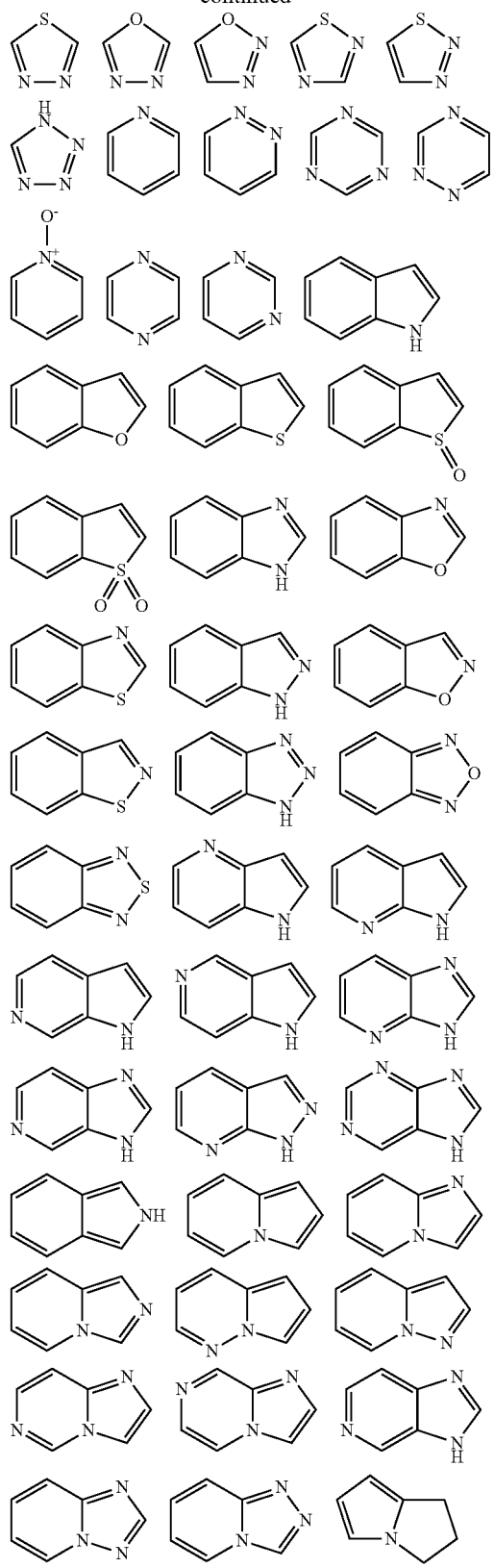

Many of the terms given above may be used repeatedly in the definition of a formula or group and in each case have one of the meanings given above, independently of one another.

Pharmacological Activity

The activity of the compounds of the invention may be demonstrated using the following ACC2 assay:

Spectrophotometric 384 Well Assay

Malonyl CoA formation by acetyl CoA carboxylases is stoichiometrically linked to the consumption of ATP. ACC2 activity is measured in a NADH-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM $KHCO_3$, 10 mM $MgCl_2$, 0.5 mg/mL BSA, 3.75 mM reduced L-glutathione, 15 U/mL lactate dehydrogenase, 0.5 mM phosphoenolpyruvate, 15 U/mL pyruvate kinase, compounds at different concentrations at final DMSO concentrations of 1%.

The enzymatic reaction is then started by addition of a mixture of NADH, acetyl Coenzyme A (both 200 μM f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW'). The slope S is used for calculation of % CTL=(S(compound)−S('LOW'))/(S('HIGH')—S('LOW'))*100. Compounds will give values between 100% CTL (no inhibition) and 0% CTL (complete inhibition).

For IC50 value determination, the sample slope in the presence of the test compound after subtraction of the low controls (S(compound)−S('LOW')) are used.

An IC50 value is derived from the compound slopes at different dosages after subtraction of the low controls (S(compound)−S('LOW')) by non-linear regression curve fitting (equation y=(A+((B−A)/(1+((C/x)^D))))).

The compounds of general formula (I) according to the invention for example have $IC_{50}$ values below 30000 nM, particularly below 1000 nM, preferably below 300 nM.

In the following table the activity expressed as IC50 (μM) of compounds according to the invention is presented wherein the IC50 values are determined in the ACC2 assay as described hereinbefore. The term "Ex." refers to the example numbers according to the following experimental section.

| Ex. | IC50 [μM] |
|---|---|
| 1.1 | 4.3 |
| 1.2 | 29.7 |
| 1.3 | 0.22 |
| 1.4 | 16.1 |
| 1.5 | 0.09 |
| 1.6 | 5.4 |
| 1.7 | 28.7 |
| 1.8 | 2.4 |
| 1.9 | 0.22 |
| 1.10 | 0.53 |
| 1.11 | 0.66 |
| 1.12 | 9.7 |
| 1.13 | 2.8 |
| 1.14 | 0.60 |
| 1.15 | 0.08 |
| 1.16 | 0.61 |
| 1.17 | 0.12 |
| 1.18 | 1.3 |
| 1.19 | 29.2 |
| 1.20 | 13.2 |
| 1.21 | 30.0 |
| 1.22 | 3.6 |
| 1.23 | 1.0 |
| 1.24 | 2.7 |
| 1.25 | 0.73 |
| 2.1 | 0.69 |
| 2.2 | 3.7 |
| 2.3 | 0.71 |
| 2.4 | 0.39 |
| 2.5 | 3.0 |
| 2.6 | 0.41 |
| 2.7 | 3.7 |
| 2.8 | 0.28 |
| 2.9 | 2.5 |
| 2.10 | 2.3 |
| 2.11 | 0.27 |
| 2.12 | 0.69 |
| 2.13 | 0.24 |
| 2.14 | 6.8 |
| 2.15 | 1.5 |
| 2.16 | 7.4 |
| 3.1 | 8.4 |
| 3.2 | 0.40 |
| 3.3 | 0.92 |
| 3.4 | 0.46 |
| 4.1 | 0.26 |
| 4.2 | 0.87 |
| 5.1 | 1.5 |
| 5.2 | 1.8 |
| 5.3 | 0.24 |
| 5.4 | 1.1 |
| 5.5 | 0.20 |
| 5.6 | 0.23 |
| 5.7 | 0.17 |
| 5.8 | 1.5 |
| 5.9 | 0.08 |
| 5.10 | 3.7 |
| 5.11 | 0.87 |
| 5.12 | 0.44 |
| 5.13 | 0.89 |
| 5.14 | 0.11 |
| 5.15 | 2.7 |
| 5.16 | 1.4 |
| 5.17 | 0.93 |
| 5.18 | 1.9 |
| 5.19 | 0.25 |
| 5.20 | 0.09 |
| 5.21 | 0.54 |
| 6.1 | 0.23 |
| 6.2 | 0.52 |
| 6.3 | 0.83 |
| 6.4 | 0.41 |
| 6.5 | 0.06 |
| 6.6 | 3.6 |
| 6.7 | 3.3 |
| 6.8 | 0.62 |
| 6.9 | 1.8 |
| 6.10 | 0.19 |
| 6.11 | 0.84 |
| 6.12 | 0.13 |
| 6.13 | 0.40 |
| 6.14 | 0.24 |
| 6.15 | 0.29 |
| 6.16 | 0.10 |
| 6.17 | 18.7 |
| 6.18 | 18.7 |

-continued

| Ex. | IC50 [µM] |
|---|---|
| 6.19 | 4.5 |
| 6.20 | 8.3 |
| 6.21 | 25.5 |
| 6.22 | 1.5 |
| 6.23 | 23.1 |
| 6.24 | 1.8 |
| 6.25 | 12.8 |
| 6.26 | 18.7 |
| 7.1 | 1.3 |
| 7.2 | 0.62 |
| 7.3 | 0.11 |
| 7.4 | 0.15 |
| 7.5 | 4.4 |
| 7.6 | 4.3 |
| 7.7 | 0.25 |
| 7.8 | 2.5 |
| 7.9 | 0.25 |
| 7.10 | 0.27 |
| 7.11 | 0.38 |
| 7.12 | 1.0 |
| 7.13 | 2.0 |
| 7.14 | 5.0 |
| 7.15 | 4.0 |
| 7.16 | 1.5 |
| 7.17 | 0.36 |
| 7.18 | 2.2 |
| 7.19 | 7.7 |
| 7.20 | 0.50 |
| 7.21 | 22.5 |
| 7.22 | 0.33 |
| 7.23 | 0.56 |
| 7.24 | 0.26 |
| 7.25 | 0.07 |
| 7.26 | 25.5 |
| 7.27 | 10.9 |
| 7.28 | 2.9 |
| 7.29 | 0.25 |
| 7.30 | 0.22 |
| 7.31 | 0.64 |
| 7.32 | 0.44 |
| 7.33 | 5.4 |
| 7.34 | 1.1 |
| 7.35 | 2.1 |
| 7.36 | 3.8 |
| 7.37 | 3.2 |
| 7.38 | 2.9 |
| 7.39 | 1.2 |
| 7.40 | 0.14 |
| 7.41 | 0.51 |
| 7.42 | 0.09 |
| 7.43 | 0.17 |
| 7.44 | 0.25 |
| 7.45 | 0.39 |
| 7.46 | 0.11 |
| 7.47 | 0.49 |
| 7.48 | 25.7 |
| 7.49 | 0.06 |

In view of their ability to inhibit the enzyme(s) acetyl-CoA carboxylase, the compounds of general formula (I) according to the invention and the corresponding salts thereof are theoretically suitable for the treatment, including preventative treatment of all those diseases or conditions which may be affected or which are mediated by the inhibition of the enzyme(s) acetyl-CoA carboxylase, in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase enzyme(s), in particular ACC2, in a patient, preferably in a human.

In yet another aspect the present invention relates a method for treating, including preventing a disease or condition mediated by the inhibition of acetyl-CoA carboxylase enzyme(s) in a mammal that includes the step of administering to a patient, preferably a human, in need of such treatment a therapeutically effective amount of a compound of the present invention, or a pharmaceutical composition thereof.

Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as is hyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, microalbuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or greater.

According to another aspect the compounds of the present invention are particularly suitable for treating, including preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:

A. disorders of fatty acid metabolism and glucose utilization disorders; disorders in which insulin resistance is involved;
B. hepatic disorders and conditions related thereto, including: fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;
C. skin disorders and conditions and those associated with polyunsaturated fatty acids, such as
  eczema, acne, sebaceous gland diseases, psoriasis, keloid scar formation or prevention, other diseases related to mucous membrane fatty acid composition;
D. primary hypertriglyceridemia or secondary hypertriglyceridemias following familial histiocytic reticulosis, lipoprotein lipase deficiency, hyperlipo-proteinemias, apolipoprotein deficiency (e.g. apoCII or apoE deficiency);
E. diseases or conditions related to neoplastic cellular proliferation, for example benign or malignant tumors, cancer, neoplasias, metastases, carcinogenesis;
F. diseases or conditions related to neurological, psychiatric or immune disorders or conditions;
G. other diseases or conditions in which inflammatory reactions, cell differentiation and/or other ACC-mediated aspects may for example be involved are:
  atherosclerosis such as, for example (but not restricted thereto), coronary sclerosis including angina pectoris or myocardial infarction, stroke, ischemic, stroke and transient ischemic attack (TIA),
  peripheral occlusive disease,
  vascular restenosis or reocclusion,
  chronic inflammatory bowel diseases such as, for example, Crohn's disease and ulcerative colitis,
  pancreatitis,
  sinusitis,
  retinopathy, ischemic retinopathy,
  adipose cell tumors,
  lipomatous carcinomas such as, for example, liposarcomas,
  solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc.,
  tumors in which ACC is up regulated,
  acute and chronic myeloproliferative disorders and lymphomas, angiogenesis
  neurodegenerative disorders including Alzheimer's disease, multiple sclerosis, Parkinson's disease, epilepsy,
  erythemato-squamous dermatoses such as, for example, psoriasis,
  acne vulgaris,
  other skin disorders and dermatological conditions which are modulated by PPAR,
  eczemas and neurodermatitis,
  dermatitis such as, for example, seborrheic dermatitis or photodermatitis,
  keratitis and keratoses such as, for example, seborrheic keratoses, senile keratoses, actinic keratoses, photo-induced keratoses or keratosis follicularis,
  keloids and keloid prophylaxis,
  bacterial infections,
  fungal infections,
  warts, including condylomata or condylomata acuminata
  viral infections such as, for example, human hepatitis B virus (HBV), hepatitis C virus (HCV), West Nile virus (WNV) or Dengue virus, human Immunodeficiency virus (HIV), poxvirus and Vaccinia virus (VV), HCMV, influenza A, human papilloma viral (HPV). venereal papillomata, viral warts such as, for example, molluscum contagiosum, leukoplakia,
  papular dermatoses such as, for example, lichen planus,
  skin cancer such as, for example, basal-cell carcinomas, melanomas or cutaneous T-cell lymphomas,
  localized benign epidermal tumors such as, for example, keratoderma, epidermal naevi,
  chilblains;
  high blood pressure,
  polycystic ovary syndrome (PCOS),
  asthma,
  cystic fibrosis,
  osteoarthritis,
  lupus erythematosus (LE) or inflammatory rheumatic disorders such as, for example rheumatoid arthritis,
  vasculitis,
  wasting (cachexia),
  gout,
  ischemia/reperfusion syndrome,
  acute respiratory distress syndrome (ARDS)
  viral diseases and infections
  lipodystrophy and lipodystrophic conditions, also for treating adverse drug effect;
  myopathies and lipid myopathis (such as carnitine palmitoyltransferase I or II deficiency);
H. formation of muscles and a lean body or muscle mass formation.

The dose range of the compounds of general formula (I) applicable per day is usually from 0.001 to 10 mg, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11beta-hydroxy steroid dehydrogenase-1 (11beta-HSD type 1) inhibitors, stearoyl-CoA desaturase-1 (SCD-1) inhibitors, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-Y antagonists (e.g., NPY Y5 antagonists), $PY_{Y3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, GOAT (Ghrelin O-Acyltransferase) inhibitors, histamine 3 antagonists or inverse agonists, neuromedin U agonists, MTP/ApoB inhibitors (e.g., gut-selective MTP inhibitors), opioid antagonists, orexin antagonists, and the like.

Preferred anti-obesity agents for use in the combination aspects of the present invention include gut-selective MTP inhibitors CCKa agonists, 5HT2c agonists, MCR4 agonists, lipase inhibitors, opioid antagonists, oleoyl-estrone, obinepitide, pramlintide (Symlin®), tesofensine (NS2330), leptin, liraglutide, bromocriptine, orlistat, exenatide (Byetta®), AOD-9604 (CAS No. 221231-10-3) and sibutramine.

Suitable anti-diabetic agents include sodium-glucose co-transporter (SGLT) inhibitors, 11beta-hydroxy steroid dehydrogenase-1 (11beta-HSD type 1) inhibitors, phosphodiesterase (PDE) 10 inhibitors, diacylglycerol acyltransferase (DGAT) 1 or 2 inhibitors, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, an alpha-amylase inhibitors (e.g., tendamistat, trestatin and AL-3688), alpha-glucoside hydrolase inhibitors (e.g., acarbose), alpha-glucosidase inhibitors (e.g., adiposine, camiglibose, emiglitate, miglitol, voglibose, pradimicin-Q, and salbostatin), PPAR gamma agonists (e.g., balaglitazone, ciglitazone, darglitazone, englitazone, isaglitazone, pioglitazone, rosiglitazone and troglitazone), PPAR alpha/gamma agonists (e.g., CLX-0940, GW-1536, GW-20 1929, GW-2433, KRP-297, L-796449, LR-90, MK-0767 and SB-219994), biguanides (e.g., metformin), GLP-1 derivatives, glucagon-like peptide 1 (GLP-1) agonists (e.g., Byetta™, exendin-3 and exendin-4), GLP-1 receptor and glucagon receptor co-agonists, glucagon receptor antagonists, GIP receptor antagonists, protein tyrosine phosphatase-1 B (PTP-1 B) inhibitors (e.g., trodusquemine, hyrtiosal extract), SIRT-1 activators (e.g. reservatrol), dipeptidyl peptidase IV (DPP-IV) inhibitors (e.g., sitagliptin, vildagliptin, alogliptin, linagliptin and saxagliptin), insulin secretagogues, GPR119 agonists, GPR40 agonists, TGR5 agonists, MNK2 inhibitors, GOAT (Ghrelin O-Acyltransferase) inhibitors, fatty acid oxidation inhibitors, A2 antagonists, c-jun amino-terminal kinase (JNK) inhibitors, insulins, insulin derivatives, fast acting insulins, inhalable insulins, oral insulins, insulin mimetics, glycogen phosphorylase inhibitors, VPAC2 receptor agonists and glucokinase activators.

Preferred anti-diabetic agents are metformin, glucagon-like peptide 1 (GLP-1) agonists (e.g., Byetta™), GLP-1 receptor and glucagon receptor co-agonists, sodium-glucose co-transporter (SGLT) inhibitors, 11beta-hydroxy steroid dehydrogenase-1 (11beta-HSD type 1) inhibitors and DPP-IV inhibitors (e.g. sitagliptin, vildagliptin, alogliptin, linagliptin and saxagliptin).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of the enzyme(s) acetyl-CoA carboxylase, in particular ACC2, in particular diseases or conditions as described hereinbefore and hereinafter.

In yet another aspect the present invention relates a method for treating, including preventing a disease or condition mediated by the inhibition of acetyl-CoA carboxylase enzyme(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

EXAMPLES

The Examples that follow are intended to illustrate the present invention without restricting it. The terms "ambient temperature" and "room temperature" are used interchangeably and designate a temperature of about 20° C.

Preliminary Remarks:

As a rule, 1H-NMR and/or mass spectra have been obtained for the compounds prepared. The $R_f$ values are determined using Merck silica gel 60 $F_{254}$ plates and UV light at 254 nm.

Experimental Part

The following abbreviations are used above and hereinafter:

aq. aqueous
ACN acetonitrile
CDI N,N-carbonyldiimidazole
CuI copper(I) iodide
DCM dichloromethane
DIAD diisopropyl azodicarboxylate
DIPEA N,N-diisopropylethylamine
DMF N,N-dimethylformamide
dppf 1,1'-bis[diphenylphosphino]-ferrocene
EtOAc ethyl acetate
EtOH ethanol
FA formic acid
MeOH methanol
NaOH soda lye
PE petroleum ether
RP reversed phase
rt room temperature (about 20° C.)
sat. saturated
TBME tert-butyl methyl ether
TEA triethylamine
TFA trifluoroacetic acid
THF tetrahydrofuran
TBTU 2-(1H-benzotriazol-1-yl)-1,1,3,3-tetramethyluronium tetrafluoroborat Analytic Methods

1) HPLC

Method A

| time (min) | Vol % water (incl. 0.1% FA) | Vol % acetonitrile (incl. 0.1% FA) |
|---|---|---|
| 0.0 | 95 | 5 |
| 0.1 | 95 | 5 |
| 3.1 | 2 | 98 |
| 4.5 | 2 | 98 |
| 5.0 | 95 | 5 |

Analytical column: X-terra MS C18 (Waters) 2.5 μm; 4.6×30 mm; column temperature: rt; flow: 1.0 mL/min.

Method B

| time (min) | Vol % water (incl. 0.2% NH$_4$OH) | Vol % methanol (incl. 3% water) |
|---|---|---|
| 0.0 | 95 | 5 |
| 0.2 | 95 | 5 |
| 2.8 | 5 | 95 |
| 3.0 | 5 | 95 |
| 3.1 | 0 | 100 |
| 3.8 | 0 | 100 |

Analytical column: XBridge C18 (Waters) 2.5 μm; 3.0×30 mm; column temperature: rt; flow: 1.0 mL/min.

Method C

| time (min) | Vol % water (incl. 0.2% NH$_4$OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters) 2.5 μm; 3.0×30 mm; column temperature: 40° C.; flow: 1.3 mL/min.

Method D

| time (min) | Vol % water (incl. 0.2% NH$_4$OH) | Vol % methanol (incl. 3% water) |
|---|---|---|
| 0.0 | 95 | 5 |
| 1.0 | 10 | 90 |
| 2.2 | 10 | 90 |
| 2.3 | 0 | 100 |
| 2.5 | 0 | 100 |

Analytical column: XBridge C18 (Waters) 2.5 μm; 3.0×30 mm; column temperature: 40° C.; flow: 1.3 mL/min.

Method E

| time (min) | Vol % water (incl. 0.2% FA) | Vol % methanol (incl. 3% water) |
|---|---|---|
| 0.00 | 95 | 5 |
| 1.00 | 10 | 90 |
| 2.20 | 10 | 90 |
| 2.30 | 0 | 100 |
| 2.50 | 0 | 100 |

Analytical column: Zorbax StableBond C18 (Agilent) 1.8 μm; 3.0×30 mm; column temperature: 40° C.; flow: 1.3 mL/min.

Method F

| time (min) | Vol % water (incl. 0.1% TFA) | Vol % methanol |
|---|---|---|
| 0.0 | 80 | 20 |
| 1.7 | 0 | 100 |
| 2.5 | 0 | 100 |
| 2.6 | 80 | 20 |

Analytical column: Sunfire C18 (Waters) 3.5 μm; 4.6×50 mm; column temperature: 60° C.; flow: 2.0 mL/min.

Method G

| time (min) | Vol % water (incl. 0.2% FA) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: Zorbax Stable Bond C18 (Agilent) 1.8 μm; 3.0×30 mm; column temperature: 40° C.; flow: 1.3 mL/min.

Method H

| time (min) | Vol % water (incl. 0.1% FA) | Vol % ACN (incl. 0.1% FA) |
|---|---|---|
| 0.00 | 95 | 5 |
| 0.10 | 95 | 5 |
| 1.75 | 5 | 95 |
| 1.90 | 5 | 95 |
| 1.95 | 95 | 5 |
| 2.00 | 95 | 5 |

Analytical column: Zorbax StableBond C18 (Agilent) 1.8 µm; 3.0×30 mm; column temperature: rt; flow: 1.6 mL/min.

Method I

| time (min) | Vol % water (incl. 0.1% FA) | Vol % acetonitrile (incl. 0.1% FA) |
|---|---|---|
| 0.0 | 95 | 5 |
| 3.5 | 2 | 98 |
| 6.0 | 2 | 98 |

Analytical column: XBridge C18 (Waters) 3.5 µm; 2.1×50 mm; column temperature: 35° C.; flow: 0.8 mL/min.

Method J

| time (min) | Vol % water (incl. 0.1% TFA) | Vol % methanol |
|---|---|---|
| 0.0 | 95 | 5 |
| 1.3 | 0 | 100 |
| 2.5 | 0 | 100 |
| 2.6 | 95 | 5 |

Analytical column: Sunfire C18 (Waters) 3.5 µm; 4.6×50 mm; column temperature: 40° C.; flow: 1.5 mL/min.

Method K

| time (min) | Vol % water (incl. 0.1% FA) | Vol % MeOH (incl. 0.1% FA) |
|---|---|---|
| 0.0 | 95 | 5 |
| 4.5 | 10 | 90 |
| 5.0 | 10 | 90 |
| 5.50 | 95 | 5 |

Analytical column: Symmetrie (Waters) 3.5 µm; 4.6×75 mm; column temperature: rt; flow: 1.6 mL/min.

Method L

| time (min) | Vol % water (incl. 0.1% TFA) | Vol % methanol |
|---|---|---|
| 0.0 | 80 | 20 |
| 1.7 | 0 | 100 |
| 2.5 | 0 | 100 |
| 2.6 | 80 | 20 |

Analytical column: Sunfire C18 (Waters) 3.5 µm; 4.6×50 mm; column temperature: 60° C.; flow: 2 ml/min.

Method M

| time (min) | Vol % water (incl. 0.032% NH₄OH) | Vol % methanol |
|---|---|---|
| 0.0 | 80 | 20 |
| 1.7 | 0 | 100 |
| 2.5 | 0 | 100 |
| 2.6 | 80 | 20 |

Analytical column: XBridge C18 (Waters) 3.5 µm; 4.6×50 mm; column temperature: 60° C.; flow: 2 ml/min.

Method N

| time (min) | Vol % water (incl. 0.1% TFA) | Vol % CAN (incl. 0.08% TFA) |
|---|---|---|
| 0.0 | 95 | 5 |
| 2.0 | 0 | 100 |
| 2.5 | 0 | 100 |
| 2.6 | 95 | 5 |

Analytical column: Sunfire C18 (Waters) 3.5 µm; 4.6×50 mm; column temperature: 60° C.; flow: 1.5 ml/min.

Method O

| time (min) | Vol % water (incl. 0.1% NH₄OH) | Vol % methanol |
|---|---|---|
| 0.0 | 90 | 10 |
| 0.15 | 90 | 10 |
| 4.0 | 0 | 100 |
| 4.4 | 0 | 100 |
| 4.55 | 90 | 10 |
| 5.0 | 90 | 10 |

Analytical column: XBridge C18 (Waters) 2.5 µm; 3.0×30 mm; column temperature: rt; flow: 1.6 ml/min.

Method P

| time (min) | Vol % water (incl. 0.1% FA) | Vol % methanol (incl. 0.1% FA) |
|---|---|---|
| 0.0 | 90 | 10 |
| 2.5 | 2 | 98 |
| 6.0 | 2 | 98 |

Analytical column: XBridge C18 (Waters) 3.5 µm; 2.1×50 mm; column temperature: 35° C.; flow: 0.8 mL/min.

2) GC:

Method A

Analytical column: SLB-5MS 15 m; ID 100 µm; df 0.10 µm; average velocity: 45 cm/s; carrier gas: He.

Initial temp: 60° C.; initial time: 1.0 min; solvent delay: 0.6 min; rate: 50° C./min, final temp: 250° C., final time: 1.0 min.

Preparation of Starting Compounds

Example I

Example I.1

1-Iodo-4-isobutoxybenzene

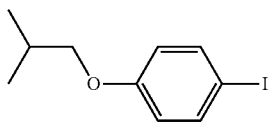

3.00 g (13.6 mmol) 4-iodophenol, 1.60 mL (15.0 mmol) 1-bromo-2-methylpropane and 7.50 g (54.5 mmol) $K_2CO_3$ are dissolved in 30 mL DMF and stirred at 80° C. for 4 h. Afterwards the reaction mixture is diluted with water and extracted with EtOAc. The organic layer is washed with diluted aq. NaOH (2×) and water (2×), dried over $MgSO_4$ and the solvent is removed in vacuo. The crude product is used without further purification.

$C_{10}H_{13}IO$ (M=276.1 g/mol)
ESI-MS: 276 $[M]^+$
$R_t$ (HPLC): 1.39 min (method E)

The following compounds are prepared analogously to example I.1:

Example II

Example II.1

2-Ethoxy-4-iodopyridine

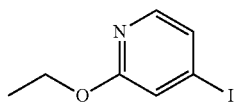

To 2.00 g (8.35 mmol) 2-chloro-4-iodopyridine in 15 mL ethanol are added 3.4 mL (9.2 mmol) sodium ethoxide and stirred at reflux for 12 h. The solvent is evaporated in vacuo and the residue is partitioned between water and DCM. The organic layer is dried over sodium sulphate and the solvent is removed in vacuo. The crude product is purified by column chromatography (silica gel; DCM/MeOH gradient 100/0→96/4).

$C_7H_8INO$ (M=249.1 g/mol)
ESI-MS: 250 $[M+H]^+$
$R_t$ (HPLC): 3.43 (method A)

| Example | Starting material | Product structure | ESI-MS [m/z] | $R_t$(HPLC) [min] (method) |
|---|---|---|---|---|
| I.1 | HO-C6H4-I | iBuO-C6H4-I | 276 $[M]^+$ | 1.39 E |
| I.2 | HO-C6H4-I | cyclopentyl-O-C6H4-I | 287 $[M-H]^-$ | 2.36 (C) |
| I.3 | HO-C6H4-I | cyclobutyl-O-C6H4-I | 274 $[M]^+$ | 2.29 (C) |
| I.4 | HO-C6H4-I | iPrO-C6H4-I | 262 $[M]^+$ | 1.29 (E) |
| I.5 | HO-C6H4-I | nPrO-C6H4-I | 262 $[M]^+$ | 2.88 (B) |

The following compounds are prepared analogously to example II.1:

| Ex. | Starting material | Product structure | ESI-MS [m/z] | $R_t$(HPLC) [min] (method) | $R_f$(TLC) |
|---|---|---|---|---|---|
| II.1 | | | 250 [M + H]$^+$ | 3.43 (A) | n.d. |
| II.2* | | | 251 [M + H]$^+$ | n.d. | 0.5 (silica gel; DCM/MeOH 50/1) |
| II.3# | | | 313 [M + H]$^+$ | 3.86 (O) | n.d. |

*the mixture is stirred at rt
the mixture is stirred at rt, solvent: THF

Example III

Example III.1

2-(4-Iodo-phenyl)-propionic acid

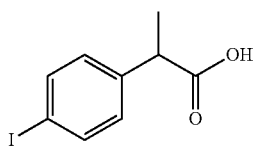

0.610 g (14.6 mmol) lithiumhydroxide monohydrate in 15 mL water are added to 2.12 g (7.31 mmol) 2-(4-iodo-phenyl)-propionic acid methyl ester (Bioorg. Med. Chem. Lett. 2010, 20, 896) in 20 mL THF and 12 mL MeOH at 0° C. Cooling is removed and the mixture is stirred at rt for 2 h. After that time, the mixture is acidified with 1 N HCl to pH~1 and extracted with DCM. The organic layer is washed with brine, dried over sodium sulphate and the solvent is evaporated. The product is used without further purification in Example IV.1

Example IV

Example IV.1

N-Ethyl-2-(4-iodo-phenyl)-propionamide

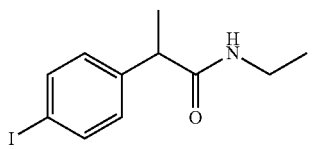

1.97 g (7.14 mmol) 2-(4-Iodo-phenyl)-propionic acid (III.1) and 1.25 mL (7.14 mmol) DIPEA are added to 582 mg (7.14 mmol) ethylamine hydrochlorid in 70 mL DCM.

1.64 g (8.57 mmol) N-(3-Dimethylaminopropyl)-N-ethylcarbodiimide hydrochloride and 194 mg (1.43 mmol) 1-hydroxy-7-azabenotriazole are added at 0° C. Subsequently, cooling is removed and the mixture is stirred for 20 h at rt. After that time, the mixture is washed with water and brine, dried over sodium sulphate and the solvent is evaporated. The residue is purified by column chromatography (silicia gel; heptane:EtOAc 50:50).

$C_{11}H_{14}INO$ (M=303.14 g/mol)

ESI-MS: 304 [M+H]$^+$

Example V

Example V.1

2-(4-Iodo-benzyl)-2-methyl-malonic acid diethyl ester

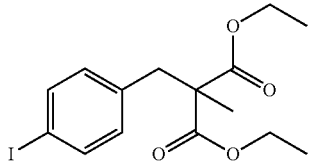 [SMILES: CCOC(=O)C(C)(Cc1ccc(I)cc1)C(=O)OCC]

220 mg (10 mmol) sodium in small pieces are added to 15 mL EtOH. After 15 min 1.65 mL (9.70 mmol) 2-methylmalonic acid diethyl ester are added. The mixture is stirred at reflux for 15 min and subsequently 3.00 g (10.1 mmol) 4-iodobenzyl bromide are added. The mixture is stirred at reflux for 12 h. After that time, the solvent is evaporated and the residue is purified by column chromatography (silicia gel; cyclohexane:EtOAc 98:2) to yield the desired product.

$C_{15}H_{19}IO_4$ (M=390.21 g/mol)

ESI-MS: 391 [M+H]$^+$

Example VI

Example VI.1

3-(4-Iodo-phenyl)-2-methyl-propionic acid

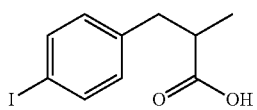

To 2.30 g (5.89 mmol) 2-(4-iodo-benzyl)-2-methyl-malonic acid diethyl ester (V.1) in 30 mL EtOH are added 30 mL 1N NaOH. The mixture is stirred at reflux for 2 h. The solvent is evaporated and 35 mL 4N HCl are added. The mixture is stirred at 60° C. for 12 h. The solid is filtered off to yield the desired product.

$C_{10}H_{11}IO_2$ (M=290.1 g/mol)
ESI-MS: 289 [M−H]⁻

Example VII

Example VII.1

4-Iodo-2-propoxy-pyridine

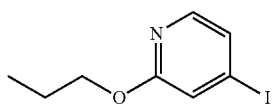

0.58 g (25 mmol) sodium are carefully added to 40 mL n-propanol in several portions. The mixture is stirred for 45 min. After that time, 6.0 g (25 mmol) 2-chloro-4-iodo-pyridine are slowly added to the mixture. The mixture is stirred at reflux for 3 h. Subsequently, water is added and the solvent is removed in vacuo. The residue is taken up in 20 mL DMF/MeOH, filtrated and the filtrate is purified by RP-HPLC (MeOH/H₂O/NH₃).

$C_8H_{10}INO$ (M=263.1 g/mol)
ESI-MS: 264 [M+H]⁺
$R_t$ (HPLC): 2.15 min (method C)

Example VIII

Example VIII.1

(4-Iodo-benzyl)-pyridin-2-yl-amine

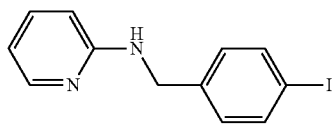

2.00 g (8.62 mmol) 4-iodo-benzaldehyde are added to 0.811 g (8.62 mmol) 2-amino-pyridine in 20 mL THF and the mixture is stirred for 1 h at 50° C. After that time, 4.57 g (21.5 mmol) sodium triacetoxyborohydride are added and the mixture is stirred for 1 h at 50° C. Subsequently, water is added and the mixture is extracted with EtOAc. The organic layer is dried over magnesium sulphate and the solvent is removed in vacuo. The residue is purified by RP-HPLC to yield the desired product.

$C_{11}H_{11}IN_2$ (M=310.13 g/mol)
ESI-MS: 311 [M+H]⁺

Example IX

Example IX.1

1-(4-Iodo-phenyl)-2-(4-methyl-imidazol-1-yl)-ethanone

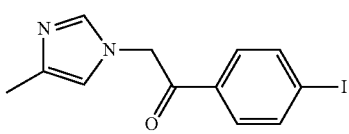 [SMILES: Cc1cn(CC(=O)c2ccc(I)cc2)cn1]

To 2.50 g (7.69 mmol) 2-bromo-1-(4-iodo-phenyl)-ethanone in 30 mL ACN are added 1.90 g (23.1 mmol) 4-methylimidazole and the mixture is stirred at rt for 48 h. After that time, the solvent is evaporated and the residue is taken up in EtOAc. The mixture is washed with water and brine (2×) and the organic layer is dried over magnesium sulphate. The solvent is evaporated and the residue is recrystallized from diethyl ether to yield the desired product.

$C_{12}H_{11}IN_2O$ (M=326.13 g/mol)
ESI-MS: 327 [M+H]⁺

Example X

Example X.1

2-(4-Iodo-phenyl)-2-methyl-propionic acid methyl ester

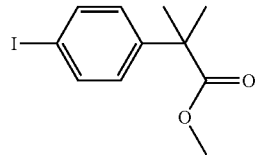

To 0.45 g (1.7 mmol) 2-(4-bromo-phenyl)-2-methyl-propionic acid methyl ester (WO2008/002671) in 1.5 mL 1,4-dioxane are added 34 mg (0.18 mmol) copper(I) iodide, 0.53 g (3.5 mmol) sodium iodide and 0.04 mL (0.35 mmol) N,N'-dimethylethylendiamine under inert gas atmosphere. The mixture is stirred at 110° C. for 12 h. After cooling, the mixture is diluted with EtOAc and washed with 5% ammonia and water. The organic layer is dried over sodium sulphate. The solvent is evaporated to yield the desired product.

$C_{11}H_{13}IO_2$ (M=304.12 g/mol)
ESI-MS: 305 [M+H]⁺
$R_t$ (HPLC): 2.21 min (method C)

Example X.2

5-Iodo-2-propoxy-pyridine

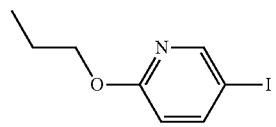

The compound is prepared according to the procedure described in Example X.1 using 5-bromo-2-propoxy-pyridine.
$C_8H_{10}INO$ (M=263.07 g/mol)
ESI-MS: 264 [M]$^+$
$R_t$ (HPLC): 2.14 min (method C)

Example XI

Example XI.1

1-Bromo-4-[(4-ethoxyphenyl)ethynyl]benzene

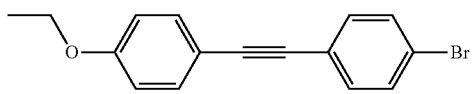 [SMILES: CCOc1ccc(C#Cc2ccc(Br)cc2)cc1]

To 1.60 g (11.0 mmol) 4-ethoxyphenylacetylene in 40 mL THF are added 3.10 g (11.0 mmol) 1-bromo-4-iodo-benzene under argon, followed by 0.18 g (0.22 mmol) Pd(dppf)Cl$_2$CH$_2$Cl$_2$ as catalyst, 0.04 g (0.22 mmol) copper(I)iodide and 3.10 mL (21.9 mmol) diisopropylamine as base. The mixture is stirred at rt for 3 h. After that time, EtOAc is added and the organic layer is washed with ammonia (5%, 2×) and water (1×). The organic layer is separated, dried over magnesium sulphate and the solvent is evaporated. The residue is purified by column chromatography (silicia gel; PE:EtOAc 9:1) to yield the desired product.
$C_{16}H_{13}BrO$ (M=301.2 g/mol)
ESI-MS: 309 [M+H]$^+$
$R_t$ (HPLC): 3.99 min (method I)

The following compounds of general formula (XI-1) are prepared analogously to Example XI.1, the educts used being shown in the column headed "E 1":

(XI-1)

| Example | Ar$^1$ | R$^1$ | E 1 | catalyst base | ESI-MS [m/z] | R$_t$ HPLC [min] (method) |
|---|---|---|---|---|---|---|
| XI.1 | 4-ethoxyphenyl | *—Br | 1-bromo-4-iodobenzene | c1 | 309 [M + H]$^+$ | 3.99 (I) |
| XI.2 | 4-ethoxyphenyl | *—CH(CH$_3$)COOH | III.1 | c2 | 407 [M + H]$^+$ | 2.30 (A) |
| XI.3$^\#$ | 4-propoxyphenyl | *—CH$_2$COOCH$_3$ | methyl 4-iodophenylacetate | c3 | 295 [M + H]$^+$ | 5.72 (K) |
| XI.4 | 4-ethoxyphenyl | *—C(CH$_3$)$_2$COOCH$_3$ | X.1 | c2 | 295 [M + H]$^+$ | 2.24 (C) |
| XI.5 | 4-ethoxyphenyl | *—C(CH$_3$)(OH)COOH | VI.1 | c1 | 337 [M + H]$^+$ | 1.46 (D) |
| XI.6$^{\#\#}$ | 4-ethoxyphenyl | *—CH(CH$_3$)COOCH$_3$ | methyl 2-(4-iodophenyl)propanoate | c4 | 309 [M + H]$^+$ | n.d. |

$^\#$Using 4-propoxyphenylacetylene as reactant, for E 1 refer to Bioorg. Med. Chem. Lett. 2008, 18, 749.
$^{\#\#}$For E 1 refer to Bioorg. Med. Chem. Lett. 2010, 20, 896.
c1: Pd(PPh$_3$)$_2$Cl$_2$, diisopropyl-amine
c2: Pd(dppf)Cl$_2$ CH$_2$Cl$_2$, diisopropyl-amine
c3: Pd(dppf)Cl$_2$, diisopropyl-amine
c4: Pd(PPh$_3$)$_2$Cl$_2$, TEA

Example XII

Example XII.1

1-Ethoxy-4-[(4-iodophenyl)ethynyl]benzene

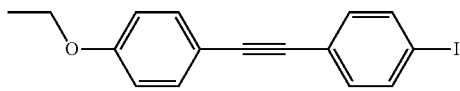 [SMILES: CCOc1ccc(C#Cc2ccc(I)cc2)cc1]

The compound is prepared according to the procedure described in Example X using 1-bromo-4-[(4-ethoxyphenyl)ethynyl]benzene (XI.1).

$C_{16}H_{31}IO$ (M=348.19 g/mol)
ESI-MS: 348 [M]$^+$
$R_t$ (HPLC): 2.47 min (method C)

Example XIII

Example XIII.1

3-[4-(4-Ethoxy-phenylethynyl)-phenyl]-propionic acid ethyl ester

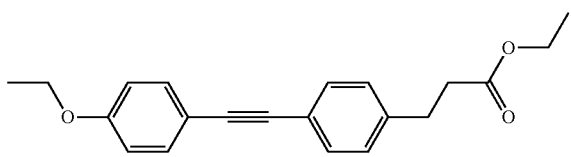 [SMILES: CCOC(=O)CCc1ccc(C#Cc2ccc(OCC)cc2)cc1]

To 1.80 g (5.17 mmol) 1-ethoxy-4-((4-iodophenyl)ethynyl)benzene (XII.1) in 24 mL DMF are added 2.36 mL (15.5 mmol) 3,3-diethoxy-propene, 3.69 mL (15.5 mmol) tributylamine, 1.44 g (5.17 mmol) tetrabutylammoniumchloride and 0.04 g (0.16 mmol) palladium(II)acetate under argon. The mixture is stirred at 120° C. for 12 h. After that time, 1.18 mL (7.76 mmol) 3,3-diethoxy-propene are added and the mixture is stirred at 120° C. for 5 d. After cooling, EtOAc is added and the mixture is washed with 1N potassium hydrogensulfate solution and water. The organic layer is dried over sodium sulphate and the solvent is evaporated. The residue is purified by column chromatography (silica gel; PE:DCM 1:1) to yield the desired product.

$C_{21}H_{22}O_3$ (M=322.40 g/mol)
ESI-MS: 323 [M+H]$^+$
$R_t$ (HPLC): 2.36 min (method C)

Example XIV

Example XIV.1

3-[4-(4-Ethoxy-phenylethynyl)-phenyl]-propionic acid

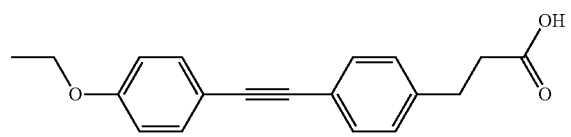 [SMILES: CCOc1ccc(C#Cc2ccc(CCC(=O)O)cc2)cc1]

To 750 mg (2.33 mmol) 3-[4-(4-ethoxy-phenylethynyl)-phenyl]-propionic acid ethyl ester (XIII.1) in 15 mL MeOH are added 3.49 mL (6.98 mmol) 2N NaOH solution and the mixture is stirred at rt for 12 h. After that time, 7.0 mL 2N HCl are added and the mixture is diluted with water. The precipitate is filtered off, washed with water and dried at 45° C. to yield the desired product.

$C_{19}H_{18}O_3$ (M=294.34 g/mol)
ESI-MS: 295 [M+H]$^+$
$R_t$ (HPLC): 1.70 min (method C)

Example XIV.2

[4-(4-Ethoxy-phenylethynyl)-phenyl]acetic acid

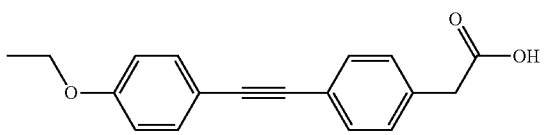 [SMILES: CCOc1ccc(C#Cc2ccc(CC(=O)O)cc2)cc1]

The compound is prepared analogously to Example XIV.1 using [4-(4-ethoxy-phenylethynyl)phenyl]-acetic acid methyl ester (XI.3).

$C_{18}H_{16}O_3$ (M=280.32 g/mol)
ESI-MS: 281 [M+H]$^+$
$R_t$ (HPLC): 1.56 min (method C)

Example XV

Example XV.1

2-Methyl-2-[4-(4-propoxy-phenylethynyl)-phenyl]-propionic acid

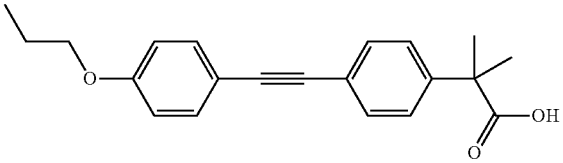 [SMILES: CCCOc1ccc(C#Cc2ccc(C(C)(C)C(=O)O)cc2)cc1]

A mixture of 26 mg (1.1 mmol) lithiumhydroxide and 99 µL (1.1 mmol) hydrogen peroxide in 0.7 mL water is added to 0.25 g (0.74 mmol) 2-methyl-2-[4-(4-propoxy-phenylethynyl)-phenyl]-propionic acid methyl ester (XI.4) in 7 mL THF. The reaction mixture is stirred at rt for 5 d. After that time, 0.5 N potassium hydrogensulfate solution is added. The precipitate is filtered off, washed with water and dried at 45° C. to yield the desired product.

$C_{21}H_{22}O_3$ (M=322.40 g/mol)
ESI-MS: 323 [M+H]$^+$
$R_t$ (HPLC): 2.38 min (method G)

Example XVI

Example XVI.1

N-Ethyl-2-(4-trimethylsilanylethynyl-phenyl)-propionamide

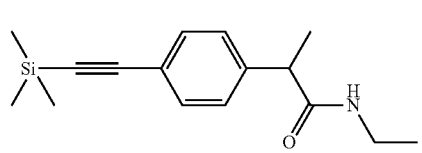

To 4.90 g (49.9 mmol) trimethylsilylacetylene in 450 mL acetonitrile are added 12.1 g (39.9 mmol) N-ethyl-2-(4-iodo-phenyl)-propionamide (IV.1) under argon, followed by 1.68 g (2.40 mmol) Pd(PPh$_3$)$_2$Cl$_2$ as catalyst, 0.23 g (1.20 mmol) copper(I)iodide and 11.1 mL (80 mmol) TEA as base. The mixture is stirred at rt for 2.5 h. After that time, EtOAc is added and the organic layer is washed with saturated ammonium chloride solution and brine. The organic layer is separated, dried over sodium sulphate and the solvent is evaporated. The residue is purified by column chromatography (silicia gel; EtOAc/heptane, gradient 50% to 80%) to yield the desired product.
C$_{16}$H$_{23}$NOSi (M=273.44 g/mol)
ESI-MS: 274 [M+H]$^+$ Example XVII Example XVII.1

N-Ethyl-2-(4-ethynyl-phenyl)-propionamide

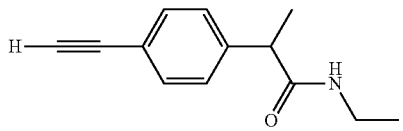

To 9.73 g (35.6 mmol) N-ethyl-2-(4-trimethylsilanylethynyl-phenyl)-propionamide (XVI.1) in 400 mL THF, an aqueous solution of 24.81 g (71.2 mmol) tetra-n-butyl-ammonium fluoride (75%) is added. The mixture is stirred at rt for 45 min. After that time, water is added and the mixture is extracted with EtOAc twice. The combined organic layers are washed with brine and dried over sodium sulphate. The solvent is evaporated and the residue is purified by column chromatography (silicia gel; EtOAc/heptane, gradient 50% to 80%) to yield the desired product.
C$_{13}$H$_{15}$NO (M=201.26 g/mol)
ESI-MS: 202 [M+H]$^+$ Example XVIII Example XVIII.1

2-[4-(2-Chloro-pyrimidin-5-ylethynyl)-phenyl]-N-ethyl-propionamide

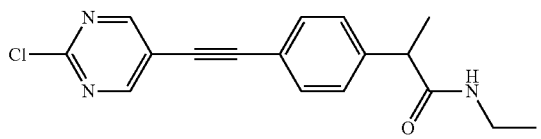 [SMILES: CCNC(=O)C(C)c1ccc(C#Cc2cnc(Cl)nc2)cc1]

To 1.10 g (5.46 mmol) N-ethyl-2-(4-ethynyl-phenyl)-propionamide (XVII.1) in 10 mL THF are added 1.31 g (5.46 mmol) 2-chloro-5-iodo-pyrimidine under argon, followed by 0.42 g (0.60 mmol) Pd(PPh$_3$)$_2$Cl$_2$ as catalyst, 57 mg (0.30 mmol) copper(I)iodide and 2.1 mL (12 mmol) DIPEA as base. The mixture is stirred at rt for 4 h. After that time, the mixture is filtered and the solvent is evaporated from the filtrate. The residue is purified by column chromatography (silicia gel; DCM:MeOH gradient 1:0/1:1).
C$_{17}$H$_{16}$ClN$_3$O (M=313.78 g/mol)
ESI-MS: 314 [M+H]$^+$
R$_t$ (HPLC): 2.12 min (method L)

Example XVIII.2

N-Ethyl-2-[4-(4-hydroxy-phenylethynyl)-phenyl]-propionamide

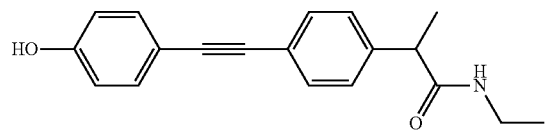 [SMILES: CCNC(=O)C(C)c1ccc(C#Cc2ccc(O)cc2)cc1]

The compound is prepared analogously to Example XVIII.1 using 4-iodophenol.
C$_{19}$H$_{19}$NO$_2$ (M=293.36 g/mol)
ESI-MS: 294 [M+H]$^+$ Example IXX Example IXX.1

N-Ethyl-3-(4-iodo-phenyl)-2-methyl-propionamide

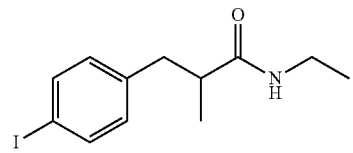

To 0.17 mg (0.59 mmol) 3-(4-iodo-phenyl)-2-methyl-propionic acid (XI.5) in 1 mL DMF, 0.28 mg (0.88 mmol) TBTU and 0.50 mL (2.9 mmol) DIPEA are added. The mixture is stirred for 15 min at rt. After that time, 106 mg (2.34 mmol) ethylamine are added and the mixture is stirred for 12 h at rt. After that time, the solvent is evaporated and the residue is purified by HPLC (Waters Xbridge 5 μm; eluent A: water+ 0.3% NH$_4$OH, eluent B: MeOH) to yield the desired product.
C$_{12}$H$_{16}$INO (M=317.16 g/mol)
ESI-MS: 318 [M+H]$^+$ Example XX Example XX.1

N-(4-Iodo-benzyl)-acetamide

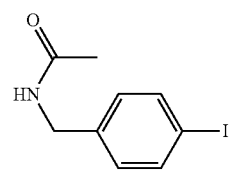

0.34 mL (3.5 mmol) acetic anhydride are added to 750 mg (3.22 mmol) 4-iodo-benzylamine in 15 ml acetic acid and the mixture is stirred at rt for 4 h. After that time, the solvent is evaporated and the residue partitionated between TBME and water. The organic layer is separated, washed with water (1×) and saturated NaHCO$_3$ solution (2×). The organic layer is dried over sodium sulphate and the solvent is evaporated to yield the desired product.

$C_9H_{10}INO$ (M=275.08 g/mol)
ESI-MS: 276 [M+H]$^+$
$R_t$ (HPLC): 1.60 min (method C)

Example XXI

Example XXI.1

4-Iodo-1H-pyridin-2-one

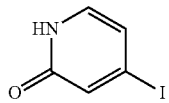

2.00 g (9.05 mmol) 4-iodo-2-pyridone (XXII.1) are added to 1.00 mL (10.9 mmol) 1-bromopropane and 3.13 g (22.6 mmol) $K_2CO_3$ in 10 mL DMF. The mixture is stirred at rt over night. After that time, water is added and the mixture is extracted with EtOAc. The organic layer is washed with aq. $NaHCO_3$ solution, dried over sodium sulphate and the solvent is removed in vacuo. The residue is purified by RP-HPLC (water+0.15% FA, MeOH).

$C_8H_{10}INO$ (M=263.1 g/mol)
ESI-MS: 264 [M+H]$^+$
$R_t$ (HPLC): 1.51 min (method C)

The following compounds are prepared analogously to example XXII.1

| Ex. | Starting material | Product structure | ESI-MS [m/z] | $R_t$(HPLC) [min] (method) |
|---|---|---|---|---|
| XXII.1 | 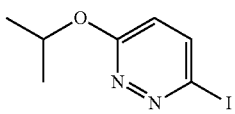 | | 264 [M + H]$^+$ | 1.51 (C) |
| XXII.2 | | | 278 [M + H]$^+$ | 2.99 (P) |
| XXII.3 | | | 278 [M + H]$^+$ | 3.03 (P) |

17.1 g (208 mmol) sodium acetate are added to 10.0 g (41.8 mmol) 2-chloro-4-iodopyridine in 100 mL acetic acid and the mixture is heated at 180° C. for 2 h in a microwave oven. DCM and water are added to the mixture. The organic layer is separated and washed with water, dried over sodium sulphate and the solvent is removed in vacuo. The crude product is triturated with TBME.

$C_5H_4INO$ (M=221.0 g/mol)
ESI-MS: 222 [M+H]$^+$
$R_f$ (TLC): 0.3 (silicia gel; DCM:MeOH 9:1)

Example XXII

Example XXII.1

4-Iodo-N-propyl-2-pyridone

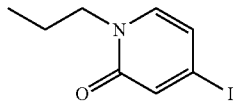

Example XXIII

Example XXIII.1

3-Iodo-6-isopropoxy-pyridazine 0.50 mL (6.6 mmol) isopropanol are added to 289 mg (7.23 mmol) sodium hydride (60%) in 100 mL THF and the mixture is stirred for 30 min at rt. After that time, 2.0 g (6.0 mmol) 3,6-diiodo-pyridazine are added and the mixture is stirred for 14 h at rt and for 14 h at 50° C. After that time, the mixture is poured into water and extracted with EtOAc. The organic layer is washed with water (2×) and dried over sodium sulphate. The solvent is removed in vacuo and the residue is purified by column chromatography (silicia gel; heptane:EtOAc gradient 0 to 50%).

$C_7H_9IN_2O$ (M=264.06 g/mol)
ESI-MS: 265 [M+H]$^+$
$R_t$ (HPLC): 3.14 min (method P)

The following compounds are prepared analogously to example XXIII.1

| Example | Starting material | Product structure | ESI-MS [m/z] | R$_t$(HPLC) [min] (method) |
|---|---|---|---|---|
| XXIII.1 |  |  | 265 [M + H]$^+$ | 3.14 (P) |
| XXIII.2 |  |  | 279 [M + H]$^+$ | 3.35 (P) |

Example XXIV

Example XXIV.1

5-Bromo-2-(2-methoxyethoxy)pyridine

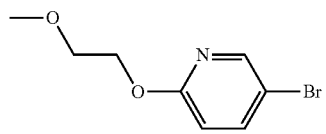

0.25 mL 2-methoxyethanol (3.17 mmol) are added to a mixture of 80 mg (3.17 mmol) sodium hydride and 5 mL THF. The mixture is stirred at rt for 10 min. Subsequently, 500 mg (2.11 mmol) 2,5-dibromopyridine are added and the mixture is stirred for 5 h at 75° C. After that time, the reaction mixture is diluted with sat. aq. NaHCO$_3$ solution and extracted with EtOAc. The organic layer is dried over magnesium sulphate and the solvent is removed in vacuo. The crude product is purified by column chromatography (silica gel, PE/EtOAc 85/15).

C$_8$H$_{10}$BrNO$_2$ (M=232.1 g/mol)
ESI-MS: 232 [M+H]$^+$
R$_t$ (HPLC): 1.72 min (method C)

The following compounds are prepared analogously to example XXIV.1:

| Example | Starting material | Product structure | ESI-MS [m/z] | R$_t$(HPLC) [min] (method) |
|---|---|---|---|---|
| XXIV.1 |  | 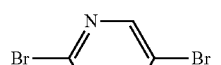 | 232 [M + H]$^+$ | 1.72 (C) |
| XXIV.2* |  | 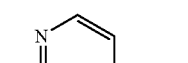 | 298 [M + H]$^+$ | 3.64 (P) |
| XXIV.3 |  | 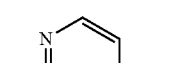 | 278 [M + H]$^+$ | 4.00 (P) |
| XXIV.4* |  | 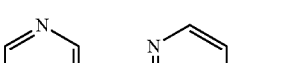 | 300 [M + H]$^+$ | 2.87 (P) |

*DMF is used as solvent.

Example XXV

Example XXV.1

1-Iodo-2-methyl-4-propoxybenzene

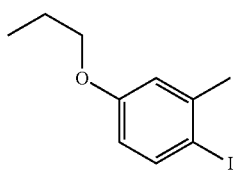

3.44 mL (45.8 mmol) 1-propanol are added to 3.42 g (30.5 mmol) KOtBu in 18 mL DMF at 0° C. After stirring the solution for 10 min at rt, 1.80 g (7.63 mmol) 4-fluoro-1-iodo-2-methylbenzene are added and the mixture is stirred at 80° C. for 3 h. The reaction is quenched by the addition of sat. aq. NH$_4$Cl solution and extracted with EtOAc (2×). The combined organic layers are washed with sat. aq. NH$_4$Cl solution and brine, dried over sodium sulphate and the solvent is removed in vacuo. The crude product is purified by column chromatography (silica gel, heptane/EtOAc 9/1).

C$_{10}$H$_{13}$IO (M=276.1 g/mol)
EI-MS: 276 [M]$^+$
R$_t$ (GC): 4.31 min (method A)

The following compounds are prepared analogously to example XXV.1:

| Example | Starting material | Product structure | ESI-MS [m/z] | R$_t$(GC) [min] (method) |
|---|---|---|---|---|
| XXV.1 | F-phenyl-I (with methyl) | propoxy-methyl-phenyl-I | 276 [M + H]$^+$ | 4.31 (A) |
| XXV.2* | F-phenyl-I (with Cl) | propoxy-Cl-phenyl-I | 296 [M]$^+$ | 4.56 (A) |

*the mixture is stirred at rt for 3 h

Example XXVI

Example XXVI.1

1-Bromo-2-methoxy-4-propoxybenzene

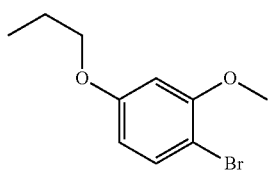

1.50 g (7.39 mmol) 4-bromo-3-methoxy-phenol are added to 1.36 g (11.1 mmol) 1-bromopropane in 10 mL DMF. 2.04 g (14.8 mmol) K$_2$CO$_3$ are added and the mixture is stirred at 80° C. for 12 h. After that time, the mixture is diluted with water and extracted with DCM. The organic layer is dried over sodium sulphate and the solvent is removed in vacuo.

C$_{10}$H$_{13}$BrO (M=245.1 g/mol)
ESI-MS: 245 [M+H]$^+$
R$_t$ (HPLC): 2.12 (method C)

Example XXVII

Example XXVII.1

1-Iodo-2-methoxy-4-propoxybenzene

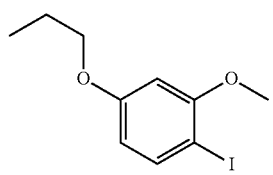

11.1 mL (17.8 mmol) BuLi (1.6M solution in hexane) are added to 3.64 g (14.9 mmol) 1-bromo-2-methoxy-4-propoxybenzene (XXVI.1) in 100 mL THF at −78° C. The mixture is stirred for 5 min at −78° C. After that time, 5.65 g (22.3 mmol) I$_2$ in 10 mL THF are added. The mixture is allowed to reach rt. The solvent is removed in vacuo and the residue is purified by column chromatography (silica gel, heptane/EtOAc 1/1).

C$_{10}$H$_{13}$IO$_2$ (M=292.1 g/mol)
EI-MS: 292 [M]$^+$.
R$_t$ (GC): 4.64 (method A)

Example XXVIII

Example XXVIII.1

Methyl-5-propoxy-2-iodobenzoate

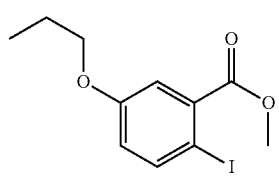

2.97 mL (32.7 mmol) 1-bromopropane and 299 mg (1.80 mmol) KI are added to a mixture of 3.39 g (24.5 mmol) K$_2$CO$_3$ and 200 mL acetone. The mixture is stirred for 30 min at reflux. Subsequently, 5.00 g (18.0 mmol) methyl-5-hydroxy-2-iodobenzoate are added and the resulting mixture is refluxed for 2 h. One additional equivalent of 1-bromopropane and of K$_2$CO$_3$ is added and refluxing is continued for 12 h. Water is added and the mixture is extracted with EtOAc. The organic layer is dried over sodium sulphate and the solvent is removed in vacuo. The crude product is purified by column chromatography (silica gel, heptane/EtOAc 100/0→60/40). The product is used without further characterization.

Example XXIX

Example XXIX.1

2-Iodo-5-propoxy-benzamide

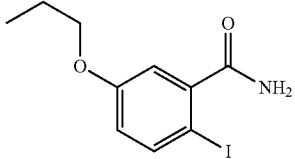

129 mL (258 mmol) 2N NaOH are added to 4.12 g (12.9 mmol) methyl-5-propoxy-2-iodobenzoate (XXVII.1) 60 mL MeOH. The mixture is stirred at 50° C. for 3 h. After that time, the mixture was acidified to pH 5 with 1N aq. HCl and extracted with EtOAc (2×). The combined organic layers are washed with water and brine, dried over sodium sulphate and the solvent is removed in vacuo. The crude product is taken up in 30 mL THF and 2.04 g (12.6 mmol) CDI are added. The mixture is stirred at rt for 1 h. Additional 0.5 eq CDI are added and stirring is continued for 20 min. 20 mL of 35% ammonia in water are added and the resulting mixture is stirred at rt for 5 min. The solvent was partly removed in vacuo until precipitation of a white solid. The product is filtered off and dried at 40° C. in vacuo.

$C_{10}H_{12}NIO_2$ (M=305.1 g/mol)
ESI-MS: 306 [M+H]$^+$
$R_t$ (HPLC): 2.98 (method P)

Example XXX

Example XXX.1

1-Iodo-2-cyano-4-propoxy-benzene

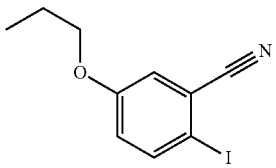

1.67 mL (22.9 mmol) SOCl$_2$ are added to 1.40 g (4.59 mmol) 2-iodo-5-propoxy-benzamide (XXIX.1) in 40 mL DMF. The mixture is stirred at 115° C. for 1 h. After that time, water is added and the mixture is extracted with EtOAc (3×). The combined organic layers are washed with water and brine, dried over sodium sulphate and the solvent is removed in vacuo. The crude product is purified by column chromatography (silica gel, heptane/EtOAc 100/0→60/40).

$C_{10}H_{10}INO$ (M=287.1 g/mol)
EI-MS: 287 [M]$^+$
$R_t$ (GC): 4.84 (method A)

Example XXXI

Example XXXI.1

4-Iodo-2-isopropoxy-pyridine

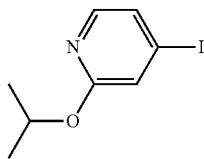

0.88 mL (11.4 mmol) 2-propanol and 3.00 (11.4 mmol) triphenylphosphine are added to 2.30 g (10.4 mmol) 4-iodo-1H-pyridin-2-one (XXI.1) in 130 mL DCM. Finally, 2.23 mL (11.4 mmol) DIAD are added at 0° C. After 5 min stirring, cooling is suspended and the mixture is stirred at rt for 2 h. After that time, the mixture is washed with water and brine, dried over sodium sulphate and the solvent is removed in vacuo. The crude product is purified by column chromatography (silicia gel; heptane/EtOAc 90/10).

$C_8H_{10}INO$ (M=279.1 g/mol)
ESI-MS: 264 [M+H]$^+$
$R_t$(HPLC): 3.72 (method P)

Preparation of Final Compounds

Example 1

Example 1.1

3-[4-(4-Ethoxy-phenylethynyl)-phenyl]-N-methyl-propionamide

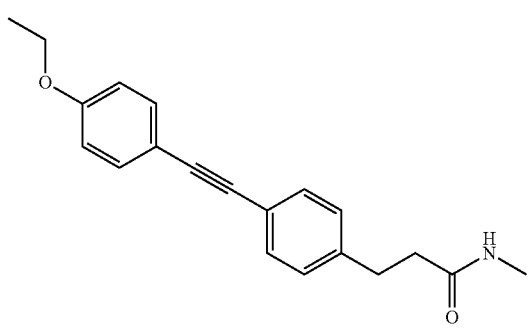 [SMILES: CCOc1ccc(C#Cc2ccc(CCC(=O)NC)cc2)cc1]

To 100 mg (0.34 mmol) 3-[4-(4-ethoxy-phenylethynyl)-phenyl]-propionic acid (XIV.1) in 5 mL DMF are added 0.12 mL (0.85 mmol) TEA and 0.12 g (0.37 mmol) TBTU and the mixture is stirred for 5 min at rt. After that time, 21 mg (0.68 mmol) methylamine are added and the mixture is stirred at rt for 2 h. Subsequently saturated potassium hydrogencarbonate solution and water are added. The precipitate is filtered, washed with water and dried at 45° C.

$C_{20}H_{21}NO_2$ (M=307.39 g/mol)
ESI-MS: 308 [M+H]$^+$
$R_t$ (HPLC): 2.09 min (method C)

The following compounds of general formula (I-1) are prepared analogously to Example 1.1, the educts used being shown in the column headed "E 1" and "E 2":

(1-1)

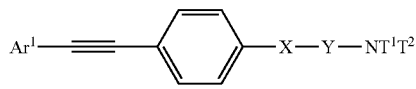

| Ex. | Ar¹ | T¹ | E 1 | E 2 | ESI-MS [m/z] | R, HPLC [min] method |
|---|---|---|---|---|---|---|
| 1.1 | 4-ethoxyphenyl | *-CH2CH2-C(=O)-NH-CH3 | XIV.1 | methylamine | 308 [M + H]⁺ | 2.09 (C) |
| 1.2 | 4-ethoxyphenyl | *-CH(CH3)-C(=O)-morpholine | XI.2 | morpholine | 407 [M + H]⁺ | 2.30 (A) |
| 1.3 | 4-ethoxyphenyl | *-CH(CH3)-C(=O)-NH-CH3 | XI.2 | methylamine | 308 [M + H]⁺ | 1.55 (H) |
| 1.4 | 4-ethoxyphenyl | *-CH(CH3)-C(=O)-N(CH3)2 | XI.2 | dimethyl-amine | 322 [M + H]⁺ | 1.67 (H) |
| 1.5 | 4-ethoxyphenyl | *-CH(CH3)-C(=O)-NH-Et | XI.2 | ethylamine | 322 [M + H]⁺ | 1.62 (H) |
| 1.6 | 4-ethoxyphenyl | *-CH2-C(=O)-NH-CH3 | XIV.2 | methylamine | 294 [M + H]⁺ | 2.04 (C) |
| 1.7 | 4-ethoxyphenyl | *-CH(CH3)-C(=O)-NH-CH2-cyclopropyl | XI.2 | cyclopropylmethylamine | 348 [M + H]⁺ | 2.23 (C) |
| 1.8 | 4-propoxyphenyl | *-C(CH3)2-C(=O)-NH-Et | XV.1 | ethylamine | 350 [M + H]⁺ | 2.31 (C) |
| 1.9 | 4-ethoxyphenyl | *-CH(CH3)-C(=O)-NH2 | XI.2 | ammonia | 294 [M + H]⁺ | 1.49 (H) |
| 1.10 | 4-ethoxyphenyl | *-CH(CH3)-C(=O)-NH-CH2-C(=O)-NH2 | XI.2 | glycinamide | 351 [M + H]⁺ | 2.02 (C) |

-continued

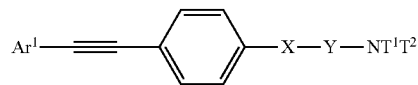

(1-1)

| Ex. | Ar¹ | T¹ | E 1 | E 2 | ESI-MS [m/z] | R$_t$ HPLC [min] method |
|---|---|---|---|---|---|---|
| 1.11 | 4-ethoxyphenyl | *CH(CH₃)C(O)NHCH₂CN | XI.2 | H₂N-CH₂-C≡N | 333 [M + H]⁺ | 2.22 (C) |
| 1.12 | 4-ethoxyphenyl | *CH(CH₃)C(O)NHCH₂CH₂OCH₃ | XI.2 | H₂N-CH₂CH₂-O-CH₃ | 352 [M + H]⁺ | 2.15 (C) |
| 1.13 | 4-ethoxyphenyl | *CH(CH₃)C(O)NH-sec-Bu | XI.2 | 2-butylamine | 350 [M + H]⁺ | 2.25 (C) |
| 1.14 | 4-propoxyphenyl | *C(CH₃)₂C(O)NH-cyclopropyl | XV.1 | cyclopropyl-amine | 362 [M + H]⁺ | 2.32 (C) |
| 1.15 | 4-ethoxyphenyl | *CH(CH₃)C(O)NHPh | XI.2 | aniline | 370 [M + H]⁺ | 2.28 (C) |
| 1.16 | 4-ethoxyphenyl | *CH(CH₃)C(O)NHPr | XI.2 | propylamine | 336 [M + H]⁺ | 2.22 (C) |
| 1.17 | 4-ethoxyphenyl | *CH(CH₃)C(O)NH-cyclopropyl | XI.2 | cyclopropyl-amine | 334 [M + H]⁺ | 2.17 (C) |
| 1.18 | 4-ethoxyphenyl | *CH(CH₃)C(O)NHCH₂C(O)OCH₃ | XI.2 | H₂N-CH₂-C(O)-O-CH₃ | 366 [M + H]⁺ | 2.12 (C) |
| 1.19 | 4-propoxyphenyl | *C(CH₃)₂C(O)NH₂ | XV.1 | ammonia | 322 [M + H]⁺ | 2.25 (C) |

(1-1)

Ar¹—≡—[phenyl]—X—Y—NT¹T²

| Ex. | Ar¹ | T¹ | E 1 | E 2 | ESI-MS [m/z] | R$_t$ HPLC [min] method |
|---|---|---|---|---|---|---|
| 1.20 | 4-ethoxyphenyl | *-CH(CH₃)-C(=O)-NH-iPr | XI.2 | 2-propyl-amine | 336 [M + H]⁺ | 2.21 (C) |
| 1.21 | 4-ethoxyphenyl | *-CH₂-C(=O)-N(CH₃)₂ | XIV.2 | dimethyl-amine | 308 [M + H]⁺ | 2.09 (C) |
| 1.22 | 4-ethoxyphenyl | *-CH₂-C(=O)-NH-Et | XIV.2 | ethylamine | 308 [M + H]⁺ | 2.07 (C) |
| 1.23 | 4-ethoxyphenyl | *-CH₂-C(=O)-NH-cyclopropyl | XIV.2 | cyclopropyl-amine | 320 [M + H]⁺ | 2.09 (C) |
| 1.24 | 4-ethoxyphenyl | *-CH₂-CH(CH₃)-C(=O)-NH-CH₃ | XI.5 | methylamine | 322 [M + H]⁺ | 2.11 (C) |
| 1.25 | 4-ethoxyphenyl | *-CH₂-CH(CH₃)-C(=O)-NH-cyclopropyl | XI.5 | cyclopropyl-amine | 348 [M + H]⁺ | 2.21 (C) |

Example 2

Example 2.1

N-Ethyl-2-[4-(2-isopropylamino-pyrimidin-5-ylethynyl)-phenyl]-propionamide

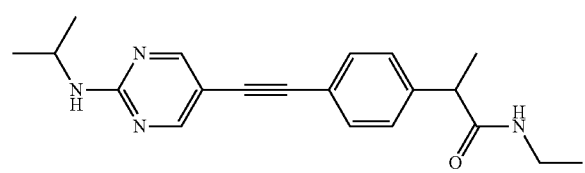 [SMILES: CCNC(=O)C(C)c1ccc(C#Cc2cnc(NC(C)C)nc2)cc1]

To 9.3 mg (0.16 mmol) isopropylamine in 0.5 mL DMSO are added 31 mg (0.10 mmol) 2-[4-(2-chloro-pyrimidin-5-ylethynyl)-phenyl]-N-ethyl-propionamide (XVIII.1) in 1 mL DMSO, followed by 254 (16 mmol) DIPEA. The mixture is stirred at rt for 12 h. After that time, the mixture is directly purified by HPLC (preparative column: Sunfire; eluent A: water+0.1% TFA, eluent B: MeOH) to yield the desired product.

$C_{20}H_{24}N_4O$ (M=336.44 g/mol)

ESI-MS: 337 [M+H]⁺

R$_t$ (HPLC): 2.10 min (method J)

The following compounds of general formula (2-1) are prepared analogously to Example 2.1, the educts used being shown in the column headed "E 1" and "E 2":

(2-1)

| Ex. | Ar¹ | X—Y—NT¹T² | E 1 | E 2 | ESI-MS [m/z] | $R_t$ HPLC [min] method |
|---|---|---|---|---|---|---|
| 2.1 | isopropyl-NH-pyrimidin-2-yl | *-CH(CH₃)-C(O)-NH-Et | XVIII.1 | isopropyl-amine | 337 [M + H]⁺ | 2.10 (J) |
| 2.2 | pyrrolidin-1-yl-pyrimidin-2-yl | *-CH(CH₃)-C(O)-NH-Et | XVIII.1 | pyrrolidine | 349 [M + H]⁺ | 2.10 (J) |
| 2.3 | cyclopentyl-NH-pyrimidin-2-yl | *-CH(CH₃)-C(O)-NH-Et | XVIII.1 | cyclopentyl-amine | 363 [M + H]⁺ | 2.10 (J) |
| 2.4 | cyclopropyl-NH-pyrimidin-2-yl | *-CH(CH₃)-C(O)-NH-Et | XVIII.1 | cyclobutyl-amine | 335 [M + H]⁺ | 2.00 (J) |
| 2.5 | (pyridin-3-yl-methyl)-NH-pyrimidin-2-yl | *-CH(CH₃)-C(O)-NH-Et | XVIII.1 | pyridin-3-yl-methyl-NH₂ | 386 [M + H]⁺ | 1.70 (J) |
| 2.6 | (sec-butyl)-NH-pyrimidin-2-yl | *-CH(CH₃)-C(O)-NH-Et | XVIII.1 | 2-butyl-amine | 351 [M + H]⁺ | 2.10 (J) |
| 2.7 | azetidin-1-yl-pyrimidin-2-yl | *-CH(CH₃)-C(O)-NH-Et | XVIII.1 | azetidine | 335 [M + H]⁺ | 2.00 (J) |
| 2.8 | ethyl-NH-pyrimidin-2-yl | *-CH(CH₃)-C(O)-NH-Et | XVIII.1 | ethylamine | 323 [M + H]⁺ | 2.10 (J) |
| 2.9 | (2-fluoroethyl)-NH-pyrimidin-2-yl | *-CH(CH₃)-C(O)-NH-Et | XVIII.1 | 2-fluoro-ethylamine | 341 [M + H]⁺ | 2.00 (J) |

-continued

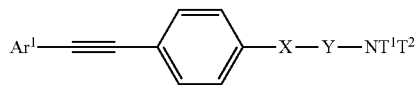

(2-1)

| Ex. | Ar¹ | X—Y—NT¹T² | E 1 | E 2 | ESI-MS [m/z] | $R_t$ HPLC [min] method |
|---|---|---|---|---|---|---|
| 2.10 | (spiro[2.4]heptane-pyrrolidinyl)-pyrimidinyl | isopropyl-C(O)NH-ethyl | XVIII.1 | spiro[2.4]heptane-pyrrolidine | 375 [M + H]⁺ | 2.20 (J) |
| 2.11 | (octahydrocyclopenta[c]pyrrol-2-yl)-pyrimidinyl | isopropyl-C(O)NH-ethyl | XVIII.1 | octahydrocyclopenta[c]pyrrole | 389 [M + H]⁺ | 2.30 (J) |
| 2.12 | cyclobutylamino-pyrimidinyl | isopropyl-C(O)NH-ethyl | XVIII.1 | cyclobutyl-amine | 349 [M + H]⁺ | 2.10 (J) |
| 2.13 | benzylamino-pyrimidinyl | isopropyl-C(O)NH-ethyl | XVIII.1 | benzyl-amine | 385 [M + H]⁺ | 2.10 (J) |
| 2.14 | N-cyclopropyl-N-methylamino-pyrimidinyl | isopropyl-C(O)NH-ethyl | XVIII.1 | N-methyl-cyclopropyl-amine | 349 [M + H]⁺ | 1.99 (M) |
| 2.15 | piperidinyl-pyrimidinyl | isopropyl-C(O)NH-ethyl | XVIII.1 | piperidine | 363 [M + H]⁺ | 2.12 (M) |
| 2.16 | (pyridin-4-yl-methylamino)-pyrimidinyl | isopropyl-C(O)NH-ethyl | XVIII.1 | (pyridin-4-yl)methylamine | 386 [M + H]⁺ | 1.75 (M) |

Example 3

Example 3.1

N-Ethyl-2-{4-[2-(2-fluoro-ethoxy)-pyrimidin-5-yl-ethynyl]-phenyl}-propionamide

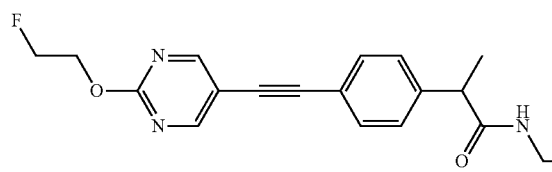

To 13 mg (0.21 mmol) 2-fluoro-ethanol in 0.5 mL 1,4-dioxane are added 34 mg (0.10 mmol) 2-[4-(2-chloro-pyrimidin-5-ylethynyl)-phenyl]-N-ethyl-propionamide (XVIII.1) in 1 mL 1,4-dioxane, followed by 12 mg (0.30 mmol) sodium hydride (60% in mineral oil). The mixture is stirred at rt for 12 h. After that time, the solvent is evaporated and the residue s purified by HPLC (preparative column: Sunfire, eluent A: water+0.1% TFA, eluent B: MeOH) to yield the desired product.

$C_{19}H_{20}FN_3O_2$ (M=341.38 g/mol)
ESI-MS: 342 [M+H]$^+$
$R_t$ (HPLC): 2.00 min (method H)

The following compounds of general formula (3-1) are prepared analogously to Example 3.1, the educts used being shown in the column headed "E 1" and "E 2":

Example 4

Example 4.1

N-Ethyl-2-[4-(4-methoxy-phenylethynyl)-phenyl]-propionamide

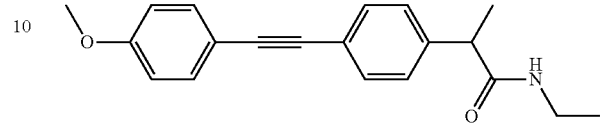

300 mg (0.99 mmol) N-Ethyl-2-(4-iodo-phenyl)-propionamide (XVIII.1) are added to 148 µL (1.14 mmol) 1-ethynyl-4-methoxybenzene in 8 mL ACN under inert gas atmosphere. 276 µL (1.99 mmol) TEA as base, 6 mg (0.03 mmol) copper(I)iodide and 42 mg (0.060 mmol) bis(triphenylphosphine)palladium(II)chloride as catalyst are added and the mixture is stirred at rt under inert gas atmosphere for 5 h. After that time, the mixture is diluted with EtOAc, washed with saturated ammonium chloride solution and brine, and the organic layer is dried over sodium sulphate. The solvent is evaporated and the residue is purified by column chromatography (silicia gel; heptane:EtOAc 50:50).

$C_{20}H_{21}NO_2$ (M=307.39 g/mol)
ESI-MS: 308 [M+H]$^+$
$R_t$ (HPLC): 3.48 min (method H)

The following compounds of general formula (4-1) are prepared analogously to Example 4.1, the educts used being shown in the column headed "E 1" and "E 2":

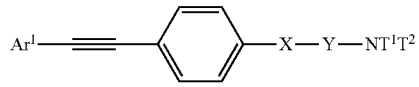

(3-1)

| Ex. | Ar$^1$ | X—Y—NT$^1$T$^2$ | E 1 | E 2 | ESI-MS [m/z] | $R_t$ HPLC [min] method |
|---|---|---|---|---|---|---|
| 3.1 | ![F-CH2CH2-O-pyrimidine] | ![propanamide-NHEt] | XVIII.1 | 2-fluoro-ethanol | 342 [M + H]$^+$ | 2.00 (H) |
| 3.2 | ![cyclobutyl-O-pyrimidine] | ![propanamide-NHEt] | XVIII.1 | cyclobutanol | 350 [M + H]$^+$ | 2.10 (H) |
| 3.3 | ![phenyl-O-pyrimidine] | ![propanamide-NHEt] | XVIII.1 | phenol | 372 [M + H]$^+$ | 2.10 (H) |
| 3.4 | ![isopropyl-O-pyrimidine] | ![propanamide-NHEt] | XVIII.1 | isopropanol | 338 [M + H]$^+$ | 2.10 (H) |

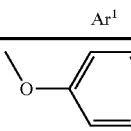
(4-1)

| Ex. | Ar¹ | X—Y—NT¹T² | E 1 | E 2 | ESI-MS [m/z] | $R_t$ HPLC [min] method |
|---|---|---|---|---|---|---|
| 4.1 | 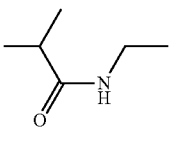 | 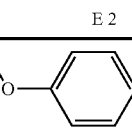 | IV.1 | 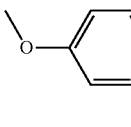 | 308 [M + H]⁺ | 3.48 (H) |
| 4.2* | 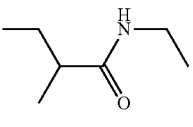 | 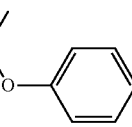 | IXX.1 | 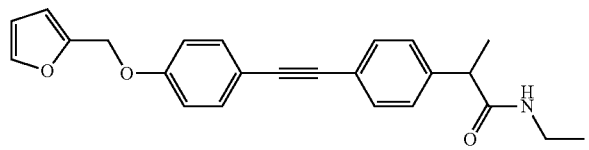 | 336 [M + H]⁺ | 2.15 (C) |

*diisoproylethylamine is used as base

Example 5

Example 5.1

N-Ethyl-2-{4-[4-(furan-2-ylmethoxy)-phenylethynyl]-phenyl}-propionamide

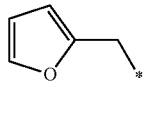

To 0.015 g (0.15 mmol) furan-2-ylmethanol in 0.75 mL THF are added 0.03 g (0.10 mmol) N-Ethyl-2-[4-(4-hydroxy-phenylethynyl)-phenyl]-propionamide (XVIII.2) and 40 mg polymer-bound triphenylphosphine (3 mmol/g resin). The mixture is cooled to 0° C. and 0.03 g (0.15 mmol) di-tert-butyl azodicarboxylate dissolved in 0.5 mL THF are added. The mixture is stirred over night at rt. After that time additional 0.03 g (0.15 mmol) di-tert-butyl azodicarboxylate dissolved in 0.5 mL THF are added and stirring is continued over night. Subsequently the mixture is filtered (Alox), washed (DMF/MeOH 9:1) and concentrated. The residue is dissolved in DMF and the desired product was purified using RP-HPLC (narrow gradient, water/MeOH+0.1% TFA).

$C_{24}H_{23}NO_3$ (M=373.45 g/mol)
ESI-MS: 374 [M+H]⁺
$R_t$ (HPLC): 2.14 min (method N)

The following compounds of general formula (5-1) are prepared analogously to Example 5.1, the educts used being shown in the column headed "E 1" and "E 2":

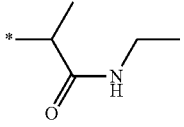
(5-1)

| Ex. | R¹ | X—Y—NT¹T² | E 1 | E 2 | ESI-MS [m/z] | $R_t$ HPLC [min] method |
|---|---|---|---|---|---|---|
| 5.1 | 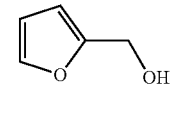 | 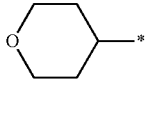 [SMILES: *C1CCOCC1] | XVIII.2 | 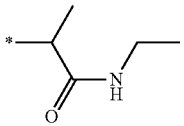 [SMILES: *C(C)C(=O)NCC] | 374 [M + H]⁺ | 2.14 (N) |
| 5.2 | 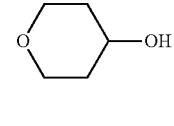 | 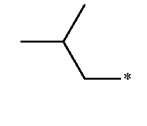 [SMILES: *CC(C)C] | XVIII.2 | 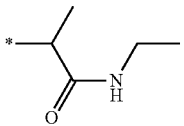 [SMILES: *C(C)C(=O)NCC] | 378 [M + H]⁺ | 2.06 (F) |
| 5.3 | 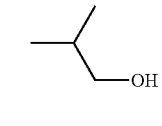 |  | XVIII.2 |  | 350 [M + H]⁺ | 2.41 (N) |

(5-1)
| Ex. | R¹ | X—Y—NT¹T² | E 1 | E 2 | ESI-MS [m/z] | $R_f$ HPLC [min] method |
|---|---|---|---|---|---|---|
| 5.4 | 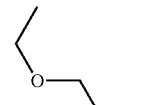 | 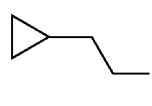 | XVIII.2 | 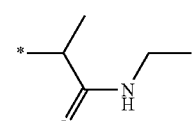 | 366 [M + H]⁺ | 2.08 (N) |
| 5.5 | 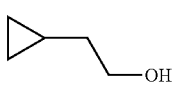 | 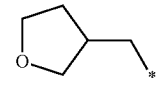 [SMILES: *CC1CCOC1] | XVIII.2 | 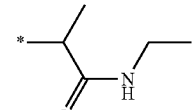 | 362 [M + H]⁺ | 2.38 (N) |
| 5.6 | 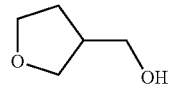 | 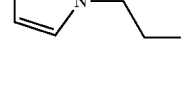 | XVIII.2 | 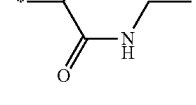 | 378 [M + H]⁺ | 2.04 (N) |
| 5.7 | 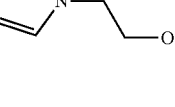 | 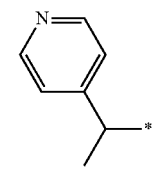 [SMILES: *C(C)c1ccncc1] | XVIII.2 | 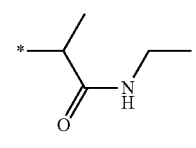 [SMILES: *C(C)C(=O)NCC] | 387 [M + H]⁺ | 2.16 (N) |
| 5.8 | 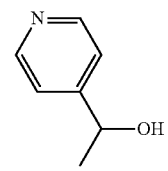 | 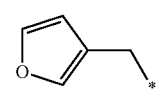 [SMILES: *Cc1ccoc1] | XVIII.2 | 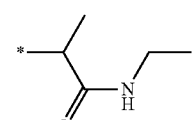 | 399 [M + H]⁺ | 1.40 (N) |
| 5.9 | 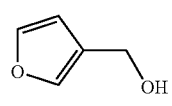 | 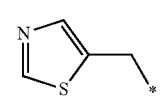 | XVIII.2 | 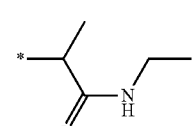 | 374 [M + H]⁺ | 2.16 (N) |
| 5.10 | 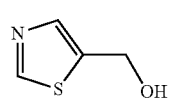 | 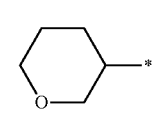 [SMILES: *C1CCCOC1] | XVIII.2 | 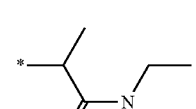 | 391 [M + H]⁺ | 1.93 (N) |
| 5.11 | 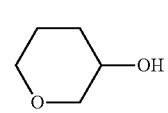 |  | XVIII.2 | 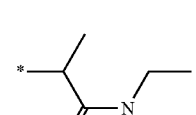 | 378 [M + H]⁺ | 2.07 (N) |
| 5.12 |  | 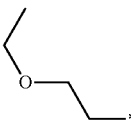 | XVIII.2 | 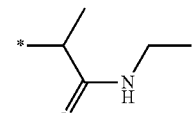 | 366 [M + H]⁺ | 2.13 (N) |

-continued (5-1)

R¹―O―⟨phenyl⟩―C≡C―⟨phenyl⟩―X―Y―NT¹T²

| Ex. | R¹ | X—Y—NT¹T² | E 1 | E 2 | ESI-MS [m/z] | $R_t$ HPLC [min] method |
|---|---|---|---|---|---|---|
| 5.13 | tetrahydropyran-4-ylmethyl | *-CH(CH₃)-C(O)-NH-Et | XVIII.2 | (tetrahydropyran-4-yl)-CH₂OH | 392 [M + H]⁺ | 2.12 (N) |
| 5.14 | F₃C-CH₂-CH₂-* | *-CH(CH₃)-C(O)-NH-Et | XVIII.2 | F₃C-CH₂-CH₂-OH | 390 [M + H]⁺ | 2.19 (N) |
| 5.15 | 3-methyloxetan-3-ylmethyl | *-CH(CH₃)-C(O)-NH-Et | XVIII.2 | (3-methyloxetan-3-yl)-CH₂OH | 378 [M + H]⁺ | 2.02 (N) |
| 5.16 | MeO-CH₂-CH(Et)-* | *-CH(CH₃)-C(O)-NH-Et | XVIII.2 | MeO-CH₂-CH(Et)-OH | 380 [M + H]⁺ | 2.23 (N) |
| 5.17 | 1H-pyrazol-4-yl-CH₂-CH₂-* | *-CH(CH₃)-C(O)-NH-Et | XVIII.2 | 1H-pyrazol-4-yl-CH₂-CH₂-OH | 388 [M + H]⁺ | 1.64 (N) |
| 5.18 | imidazol-1-yl-CH₂-CH₂-* | *-CH(CH₃)-C(O)-NH-Et | XVIII.2 | imidazol-1-yl-CH₂-CH₂-OH | 388 [M + H]⁺ | 1.33 (N) |
| 5.19 | CH₃-CHF-CH₂-* | *-CH(CH₃)-C(O)-NH-Et | XVIII.2 | CH₃-CHF-CH₂-OH | 354 [M + H]⁺ | 2.08 (N) |
| 5.20 | (2,2-difluorocyclopropyl)-CH₂-* | *-CH(CH₃)-C(O)-NH-Et | XVIII.2 | (2,2-difluorocyclopropyl)-CH₂-OH | 384 [M + H]⁺ | 2.16 (N) |
| 5.21 | oxazol-5-yl-CH₂-* | *-CH(CH₃)-C(O)-NH-Et | XVIII.2 | oxazol-5-yl-CH₂-OH | 375 [M + H]⁺ | 1.86 (N) |

Example 6

Example 6.1

N-(2,5-Dimethyl-2H-pyrazol-3-yl)-2-[4-(4-ethoxy-phenylethynyl)-phenyl]-propionamide

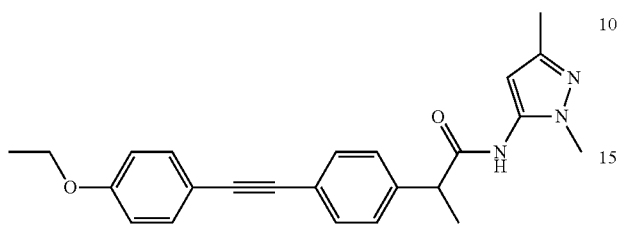

To 30 mg (0.11 mmol) 2-[4-(4-ethoxy-phenylethynyl)-phenyl]-propionic acid in (XI.2) 3 mL THF are added 55 µL (0.32 mmol) DIPEA, followed by 30 mg (0.11 mmol) chloro-N,N,N,N-tetramethylformamidinium hexafluorophosphate. The mixture is stirred at rt for 30 min. After that time, 12 mg (0.11 mmol) 5-amino-1,3-dimethylpyrazole are added and stirring is continued for 12 h. The solvent is removed and the residue is taken up in 1 mL DMF. 50 µL DIPEA are added, followed by 30 mg TBTU (0.11 mmol) and 12 mg (0.11 mmol) 5-amino-1,3-dimethylpyrazole. Stirring is continued for 12 h. The solvent is removed and the residue is purified by RP-HPLC (narrow gradients, water/ACN+0.1% TFA).

$C_{24}H_{25}N_3O_2$ (M=387.49 g/mol)

ESI-MS: 388 $[M+H]^+$ $R_t$ (HPLC): 2.02 min (method N)

The following compounds of general formula (6-1) are prepared analogously to Example 6.1, the educts used being shown in the column headed "E 1" and "E 2":

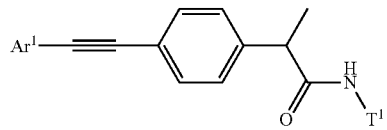

(6-1)

| Ex. | Ar¹ | NT¹T² | E 1 | E 2 | ESI-MS [m/z] | $R_t$ HPLC [min] method |
|---|---|---|---|---|---|---|
| 6.1 | 4-ethoxyphenyl | 1,3-dimethyl-1H-pyrazol-5-yl | XI.2 | 5-amino-1,3-dimethylpyrazole | 388 $[M+H]^+$ | 2.02 (N) |
| 6.2 | 4-ethoxyphenyl | pyrimidin-4-yl | XI.2 | 4-aminopyrimidine | 372 $[M+H]^+$ | 2.01 (N) |
| 6.3 | 4-ethoxyphenyl | 5-methyl-1,3,4-oxadiazol-2-yl | XI.2 | 2-amino-5-methyl-1,3,4-oxadiazole | 376 $[M+H]^+$ | 2.05 (N) |
| 6.4 | 4-ethoxyphenyl | 6-methoxypyridin-2-yl | XI.2 | 2-amino-6-methoxypyridine | 401 $[M+H]^+$ | 2.46 (L) |
| 6.5 | 4-ethoxyphenyl | pyrimidin-5-yl | XI.2 | 5-aminopyrimidine | 372 $[M+H]^+$ | 2.14 (N) |
| 6.6 | 4-ethoxyphenyl | 1H-pyrazol-5-yl | XI.2 | 5-amino-1H-pyrazole | 360 $[M+H]^+$ | 2.29 (N) |
| 6.7 | 4-ethoxyphenyl | oxazol-2-yl | XI.2 | 2-aminooxazole | 361 $[M+H]^+$ | 2.06 (N) |
| 6.8 | 4-ethoxyphenyl | oxetan-3-yl | XI.2 | 3-aminooxetane | 350 $[M+H]^+$ | 2.08 (N) |

-continued (6-1)

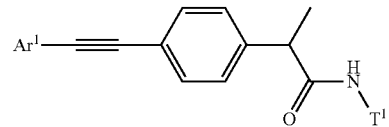

| Ex. | Ar¹ | NT¹T² | E 1 | E 2 | ESI-MS [m/z] | R$_t$ HPLC [min] method |
|---|---|---|---|---|---|---|
| 6.9 | ethoxy-phenyl | 3-tetrahydrofuranyl | XI.2 | 3-amino-tetrahydrofuran | 364 [M + H]⁺ | 2.12 (N) |
| 6.10 | ethoxy-phenyl | 1-methyl-pyrazol-5-yl | XI.2 | 5-amino-1-methyl-pyrazole | 374 [M + H]⁺ | 2.11 (N) |
| 6.11 | ethoxy-phenyl | 1-ethyl-pyrazol-5-yl | XI.2 | 5-amino-1-ethyl-pyrazole | 388 [M + H]⁺ | 2.16 (N) |
| 6.12 | ethoxy-phenyl | pyridazin-4-yl | XI.2 | 4-aminopyridazine | 372 [M + H]⁺ | 1.74 (N) |
| 6.13 | ethoxy-phenyl | pyridin-4-yl | XI.2 | 4-aminopyridine | 371 [M + H]⁺ | 1.68 (N) |
| 6.14 | ethoxy-phenyl | pyridin-3-yl | XI.2 | 3-aminopyridine | 371 [M + H]⁺ | 1.66 (N) |
| 6.15 | ethoxy-phenyl | pyrimidin-2-yl | XI.2 | 2-aminopyrimidine | 372 [M + H]⁺ | 2.02 (N) |
| 6.16 | ethoxy-phenyl | 5-methyl-isoxazol-3-yl | XI.2 | 3-amino-5-methyl-isoxazole | 375 [M + H]⁺ | 2.31 (N) |
| 6.17 | ethoxy-phenyl | tetrahydropyran-4-yl | XI.2 | 4-amino-tetrahydropyran | 378 [M + H]⁺ | 2.16 (N) |
| 6.18 | ethoxy-phenyl | isoxazol-5-ylmethyl | XI.2 | 5-(aminomethyl)isoxazole | 375 [M + H]⁺ | 2.16 (N) |
| 6.19 | ethoxy-phenyl | 1H-1,2,4-triazol-3-ylmethyl | XI.2 | 3-(aminomethyl)-1H-1,2,4-triazole | 375 [M + H]⁺ | 1.78 (N) |

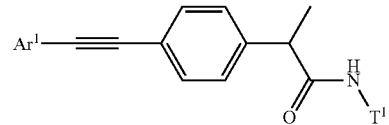

(6-1)

| Ex. | Ar¹ | NT¹T² | E 1 | E 2 | ESI-MS [m/z] | $R_t$ HPLC [min] method |
|---|---|---|---|---|---|---|
| 6.20 | ethoxy-phenyl | pyrazole-NH | XI.2 | H₂N-pyrazole-NH | 360 [M + H]⁺ | 2.28 (N) |
| 6.21 | ethoxy-phenyl | methyl-pyrazole-NH | XI.2 | H₂N-methyl-pyrazole-NH | 374 [M + H]⁺ | 2.47 (N) |
| 6.22 | ethoxy-phenyl | N-methyl-pyrazole-CH₂ | XI.2 | H₂N-CH₂-N-methyl-pyrazole | 388 [M + H]⁺ | 2.06 (N) |
| 6.23 | ethoxy-phenyl | thiadiazole | XI.2 | H₂N-thiadiazole | 378 [M + H]⁺ | 2.18 (N) |
| 6.24 | ethoxy-phenyl | oxazole-CH₂ | XI.2 | H₂N-CH₂-oxazole | 375 [M + H]⁺ | 2.09 (N) |
| 6.25 | ethoxy-phenyl | tetrahydrofuran-CH₂ | XI.2 | H₂N-CH₂-tetrahydrofuran | 378 [M + H]⁺ | 2.13 (N) |
| 6.26 | ethoxy-phenyl | C(CH₃)₂CN | XI.2 | H₂N-C(CH₃)₂CN | 361 [M + H]⁺ | 2.22 (N) |

Example 7

Example 7.1

N-Ethyl-2-[4-(4-isopropyl-phenylethynyl)-phenyl]-propionamide

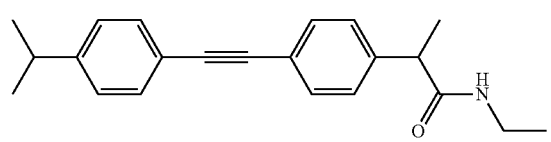 [SMILES: CCNC(=O)C(C)c1ccc(C#Cc2ccc(C(C)C)cc2)cc1]

To 0.025 g (0.10 mmol) 4-iodoisopropylbenzene are added 20 g (0.10 mmol) N-ethyl-2-(4-ethynyl-phenyl)-propionamide (XVII.1) in 1 mL THF, followed by the addition of 0.5 mL 2-butylamine and 0.75 mL water. Subsequently 3 mg (0.05 mmol) bis-(triphenylphosphine)-palladium dichloride are added and the mixture is stirred at 80° C. for 5 h. After that time, the solvent is removed. The residue is taken up in DMF and the desired product was purified using RP-HPLC (water/MeOH+0.1% TFA).

$C_{22}H_{25}NO$ (M=319.45 g/mol)

ESI-MS: 320 [M+H]⁺

$R_t$ (HPLC): 2.35 min (method N)

The following compounds of general formula (7-1) are prepared analogously to Example 7.1, the educts used being shown in the column headed "E 1" and "E 2":

(7-1)
Ar¹—≡—⟨phenyl⟩—X—Y—NT¹T²
| Ex. | Ar¹ | X—Y—NT¹T² | E 1 | E 2 | ESI-MS [m/z] | R_t HPLC [min] method |
|---|---|---|---|---|---|---|
| 7.1 | 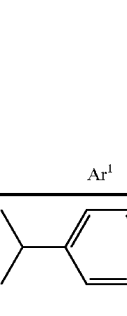 | 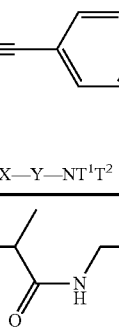 | XVII.1 | 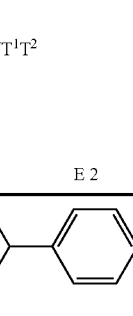 | 320 [M + H]⁺ | 2.35 (N) |
| 7.2 | 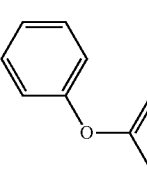 | 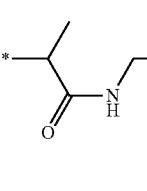 | XVII.1 | 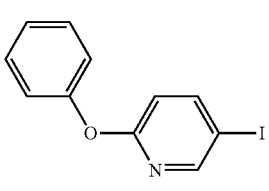 [SMILES: Ic1ccc(Oc2ccccc2)nc1] | 371 [M + H]⁺ | 2.15 (N) |
| 7.3 | 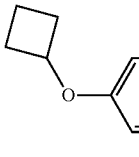 | 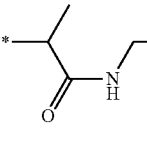 | XVII.1 | I.3 | 348 [M + H]⁺ | 2.34 (N) |
| 7.4 |  | 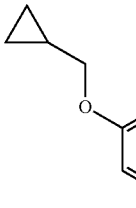 | XVII.1 | 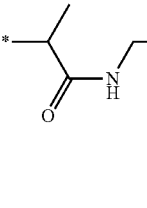 | 348 [M + H]⁺ | 2.22 (N) |
| 7.5 | 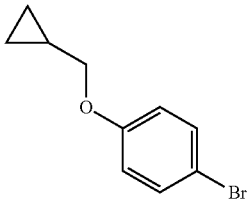 | 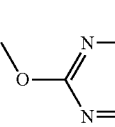 | XVII.1 | 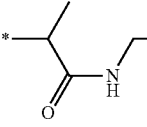 | 340 [M + H]⁺ | 1.82 (N) |
| 7.6 | 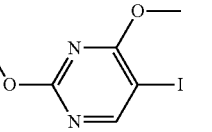 | 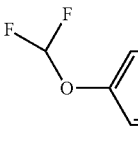 | XVII.1 | 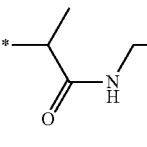 | 344 [M + H]⁺ | 2.07 (N) |
| 7.7 | 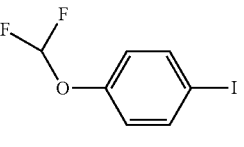 [SMILES: *c1ccc(OC(F)F)cc1] | 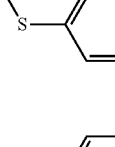 | XVII.1 | 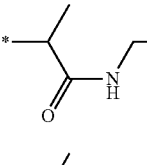 | 324 [M + H]⁺ | 2.20 (N) |
| 7.8 | 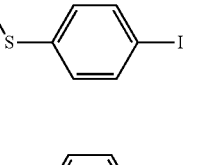 | 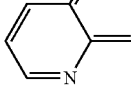 | XVII.1 | 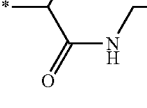 | 329 [M + H]⁺ | 1.34 (N) |
| 7.9 | 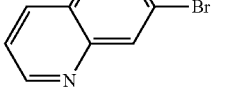 | 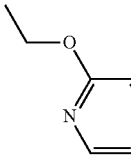 | XVII.1 | II.1 | 323 [M + H]⁺ | 1.94 (N) |

(7-1)

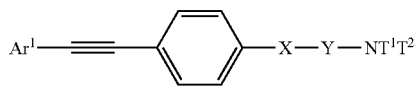

| Ex. | Ar¹ | X—Y—NT¹T² | E 1 | E 2 | ESI-MS [m/z] | R, HPLC [min] method |
|---|---|---|---|---|---|---|
| 7.10 | propyloxy-pyridinyl | *CH(CH₃)C(O)NHEt | XVII.1 | VII.1 | 337 [M + H]⁺ | 2.10 (N) |
| 7.11 | 3-(benzyloxy)phenyl | *CH(CH₃)C(O)NHEt | XVII.1 | 3-(benzyloxy)-iodobenzene | 384 [M + H]⁺ | 2.33 (N) |
| 7.12 | 1-benzyl-pyrazol-4-yl | *CH(CH₃)C(O)NHEt | XVII.1 | 1-benzyl-4-iodo-pyrazole | 358 [M + H]⁺ | 1.94 (N) |
| 7.13 | 6-ethoxy-pyrimidin-4-yl | *CH(CH₃)C(O)NHEt | XVII.1 | II.2 | 324 [M + H]⁺ | 1.85 (N) |
| 7.14 | 5-methoxy-pyridin-3-yl | *CH(CH₃)C(O)NHEt | XVII.1 | 3-iodo-5-methoxypyridine | 309 [M + H]⁺ | 1.45 (N) |
| 7.15 | 4-(2-oxo-piperidin-1-yl)phenyl | *CH(CH₃)C(O)NHEt | XVII.1 | 1-(4-iodophenyl)-piperidin-2-one | 375 [M + H]⁺ | 1.77 (N) |

-continued (7-1)

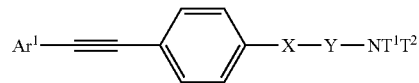

| Ex. | Ar¹ | X—Y—NT¹T² | E 1 | E 2 | ESI-MS [m/z] | $R_t$ HPLC [min] method |
|---|---|---|---|---|---|---|
| 7.16 | 2-pyridylamino-CH₂-(4-iodophenyl) | *-CH(CH₃)-C(O)-NH-Et | XVII.1 | VIII.1 | 384 [M + H]⁺ | 1.36 (N) |
| 7.17 | 4-(tert-butoxy)phenyl | *-CH(CH₃)-C(O)-NH-Et | XVII.1 | 4-(tert-butoxy)-bromobenzene | 350 [M + H]⁺ | 2.28 (N) |
| 7.18 | 1-oxo-indan-6-yl | *-CH(CH₃)-C(O)-NH-Et | XVII.1 | 6-iodo-1-oxo-indane | 332 [M + H]⁺ | 1.91 (N) |
| 7.19 | 1H-benzotriazol-5-yl | *-CH(CH₃)-C(O)-NH-Et | XVII.1 | 5-iodo-1H-benzotriazole | 319 [M + H]⁺ | 1.61 (N) |
| 7.20 | 2,3-dihydrobenzofuran-6-yl | *-CH(CH₃)-C(O)-NH-Et | XVII.1 | 6-iodo-2,3-dihydrobenzofuran | 320 [M + H]⁺ | 2.06 (N) |
| 7.21 | 4-(4-methylimidazol-1-ylmethylcarbonyl)phenyl | *-CH(CH₃)-C(O)-NH-Et | XVII.1 | IX.1 | 400 [M + H]⁺ | 1.34 (N) |
| 7.22 | 4-ethylphenyl | *-CH(CH₃)-C(O)-NH-Et | XVII.1 | 4-ethyl-iodobenzene | 320 [M + H]⁺ | 2.41 (N) |
| 7.23 | 6-ethoxypyridin-3-yl | *-CH(CH₃)-C(O)-NH-Et | XVII.1 | 5-iodo-2-ethoxypyridine | 323 [M + H]⁺ | 2.08 (N) |

-continued (7-1)

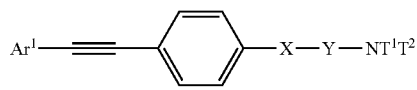

| Ex. | Ar¹ | X—Y—NT¹T² | E 1 | E 2 | ESI-MS [m/z] | R$_t$ HPLC [min] method |
|---|---|---|---|---|---|---|
| 7.24 | isopropoxy-phenyl | *-C(CH₃)HC(O)NHEt | XVII.1 | I.4 | 336 [M + H]⁺ | 2.26 (N) |
| 7.25 | propoxy-phenyl | *-C(CH₃)HC(O)NHEt | XVII.1 | I.5 | 336 [M + H]⁺ | 2.30 (N) |
| 7.26 | acetamidomethyl-phenyl | *-C(CH₃)HC(O)NHEt | XVII.1 | XX.1 | 349 [M + H]⁺ | 1.61 (N) |
| 7.27 | methoxymethyl-phenyl | *-C(CH₃)HC(O)NHEt | XVII.1 | methoxymethyl-bromobenzene | 322 [M + H]⁺ | 2.02 (N) |
| 7.28 | 2-methoxy-pyridin-5-yl | *-C(CH₃)HC(O)NHEt | XVII.1 | 2-methoxy-5-iodopyridine | 309 [M + H]⁺ | 1.96 (N) |
| 7.29 | 2-isopropoxy-pyridin-5-yl | *-C(CH₃)HC(O)NHEt | XVII.1 | 2-isopropoxy-5-iodopyridine | 337 [M + H]⁺ | 2.23 (N) |
| 7.30 | 2-cyclopentyloxy-pyridin-5-yl | *-C(CH₃)HC(O)NHEt | XVII.1 | 2-cyclopentyloxy-pyridin-5-yl | 363 [M + H]⁺ | 2.35 (N) |

-continued

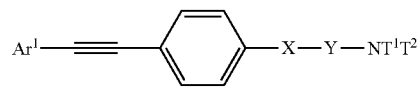
(7-1)

| Ex. | Ar¹ | X—Y—NT¹T² | E 1 | E 2 | ESI-MS [m/z] | $R_t$ HPLC [min] method |
|---|---|---|---|---|---|---|
| 7.31 | (4-benzyloxy-pyrimidin-6-yl) | *-CH(CH₃)-C(O)-NH-Et | XVII.1 | II.3 | 386 [M + H]⁺ | 2.09 (N) |
| 7.32 | (1-phenyl-pyrazol-4-yl) | *-CH(CH₃)-C(O)-NH-Et | XVII.1 | (1-phenyl-4-iodo-pyrazole) | 344 [M + H]⁺ | 2.06 (N) |
| 7.33 | (5-cyclopropyl-pyridin-2-yl) | *-CH(CH₃)-C(O)-NH-Et | XVII.1 | (5-cyclopropyl-2-bromo-pyridine) | 319 [M + H]⁺ | 1.45 (N) |
| 7.34 | (1-isobutyl-2-oxo-pyridin-4-yl) | *-CH(CH₃)-C(O)-NH-Et | XVII.1 | XXII.2 | 351 [M + H]⁺ | 1.78 (N) |
| 7.35 | (1-butyl-2-oxo-pyridin-4-yl) | *-CH(CH₃)-C(O)-NH-Et | XVII.1 | XXII.3 | 351 [M + H]⁺ | 1.81 (N) |
| 7.36 | (6-isopropoxy-pyridazin-3-yl) | *-CH(CH₃)-C(O)-NH-Et | XVII.1 | XXIII.1 | 338 [M + H]⁺ | 1.88 (N) |
| 7.37 | (6-propoxy-pyridazin-3-yl) | *-CH(CH₃)-C(O)-NH-Et | XVII.1 | XXIII.2 | 352 [M + H]⁺ | 2.02 (N) |

-continued (7-1)

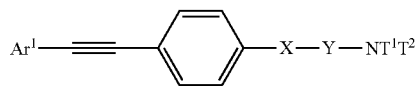

| Ex. | Ar¹ | X—Y—NT¹T² | E 1 | E 2 | ESI-MS [m/z] | $R_t$ HPLC [min] method |
|---|---|---|---|---|---|---|
| 7.38 | pyrimidine-O-pyridine | *propanamide-NHEt | XVII.1 | XXIV.4 | 373 [M + H]⁺ | 1.80 (N) |
| 7.39 | propoxy-cyanophenyl | *propanamide-NHEt | XVII.1 | XXX.1 | 361 [M + H]⁺ | 2.21 (N) |
| 7.40 | propoxy-chlorophenyl | *propanamide-NHEt | XVII.1 | XXV.2 | 370 [M + H]⁺ | 2.41 (N) |
| 7.41 | propoxy-methoxyphenyl | *propanamide-NHEt | XVII.1 | XXVI.1 | 366 [M + H]⁺ | 2.20 (N) |
| 7.42 | propoxy-methylphenyl | *propanamide-NHEt | XVII.1 | XXV.1 | 350 [M + H]⁺ | 2.35 (N) |
| 7.43 | butoxy-pyridine | *propanamide-NHEt | XVII.1 | XXIV.3 | 351 [M + H]⁺ | 2.23 (N) |
| 7.44 | isopropoxy-pyridine | *propanamide-NHEt | XVII.1 | XXXI.1 | 337 [M + H]⁺ | 2.03 (N) |

-continued (7-1)

$$Ar^1-\equiv-\underset{}{\text{C}_6\text{H}_4}-X-Y-NT^1T^2$$

| Ex. | Ar¹ | X—Y—NT¹T² | E 1 | E 2 | ESI-MS [m/z] | $R_t$ HPLC [min] method |
|---|---|---|---|---|---|---|
| 7.45 | 2-phenoxypyridin-4-yl | *-CH(CH₃)-C(O)-NH-CH₂CH₃ | XVII.1 | XXIV.2 | 371 [M + H]⁺ | 2.14 (N) |
| 7.46 | 4-(cyclopentyloxy)phenyl | *-CH(CH₃)-C(O)-NH-CH₂CH₃ | XVII.1 | I.2 | 362 [M + H]⁺ | 2.39 (N) |
| 7.47 | 6-propoxypyridin-3-yl | *-CH(CH₃)-C(O)-NH-CH₂CH₃ | XVII.1 | X.2 | 337 [M + H]⁺ | 2.21 (N) |
| 7.48 | 3,4-dimethoxyphenyl | *-CH(CH₃)-C(O)-NH-CH₂CH₃ | XVII.1 | 3,4-dimethoxy-1-iodobenzene | 338 [M + H]⁺ | 1.93 (N) |
| 7.49 | 4-(cyclopropyloxy)phenyl | *-CH(CH₃)-C(O)-NH-CH₂CH₃ | XVII.1 | 4-(cyclopropyloxy)-1-bromobenzene | 334 [M + H]⁺ | 2.19 (N) |

Examples of Formulations

The following examples of formulations, which may be obtained analogously to methods known in the art, serve to illustrate the present invention more fully without restricting it to the contents of these examples. The term "active substance" denotes one or more compounds according to the invention, including the salts thereof.

Example 1

Tablet containing 50 mg of active substance
Composition:

| | | |
|---|---|---|
| (1) Active substance | 50.0 | mg |
| (2) Lactose | 98.0 | mg |
| (3) Maize starch | 50.0 | mg |
| (4) Polyvinylpyrrolidone | 15.0 | mg |
| (5) Magnesium stearate | 2.0 | mg |
| | 215.0 | mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

Example 2

Tablet containing 350 mg of active substance
Preparation:

| | | |
|---|---|---|
| (1) Active substance | 350.0 | mg |
| (2) Lactose | 136.0 | mg |
| (3) Maize starch | 80.0 | mg |
| (4) Polyvinylpyrrolidone | 30.0 | mg |
| (5) Magnesium stearate | 4.0 | mg |
| | 600.0 | mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

Example 3

Capsules containing 50 mg of active substance
Composition:

| (1) Active substance | 50.0 mg |
|---|---|
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing. This powder mixture is packed into size 3 hard gelatin capsules in a capsule filling machine.

Example 4

Capsules containing 350 mg of active substance
Composition:

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing. This powder mixture is packed into size 0 hard gelatin capsules in a capsule filling machine.

Example 5

Dry ampoule containing 35 mg of active substance per 2 ml
Composition:

| Active substance | 35.0 mg |
|---|---|
| Mannitol | 100.0 mg |
| water for injections | ad 2.0 ml |

Preparation:

The active substance and mannitol are dissolved in water. After packaging, the solution is freeze-dried. To produce the solution ready for use, the product is dissolved in water for injections.

The invention claimed is:
1. A compound of the formula I

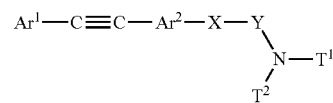

wherein
$Ar^1$ is selected from the group consisting of:

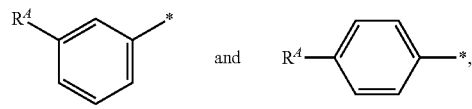

wherein
$R^A$ is selected from the group consisting of F, Cl, Br, I, CN, $NO_2$, $C_{1-6}$-alkyl, $C_{3-10}$-carbocyclyl-, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{1-4}$-alkyl-S—, $C_{3-10}$-carbocyclyl-O—, $C_{3-10}$-carbocyclyl-$C_{1-3}$-alkyl-O—, $C_{1-4}$-alkyl-C(=O)—, $R^{N1}R^{N2}N$—, $R^{N1}R^{N2}N$—$C_{2-3}$-alkyl-O—, $R^{N1}R^{N2}N$—C(=O)—, HO—C(=O)—, $C_{1-4}$-alkyl-O—C(=O)—, heterocyclyl, heterocyclyl-$C_{1-3}$-alkyl, heterocyclyl-O—, heterocyclyl-$C_{1-3}$-alkyl-O—, heterocyclyl-C(=O)—, phenyl, phenyl-O—, phenyl-$C_{1-3}$-alkyl-, phenyl-$C_{1-3}$-alkyl-O—, heteroaryl, heteroaryl-$C_{1-3}$-alkyl, heteroaryl-O— and heteroaryl-$C_{1-3}$-alkyl-O—;
wherein each heterocyclyl is selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroisoindolyl, oxetanyl, tetrahydrofuranyl and tetrahydropyranyl, or from the group consisting of

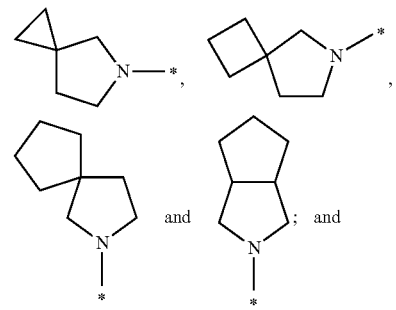

wherein carbocyclyl is selected from $C_{3-6}$-cycloalkyl; and
wherein in each carbocyclyl, pyrrolidinyl and piperidinyl a $CH_2$-group is optionally replaced with —C(=O)— or —C(=$CR^{Alk}_2$)—; and
wherein each heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, indazolyl, benzofuranyl, indolyl and quinolinyl; and
wherein each carbocyclyl or heterocyclyl are optionally substituted with one or more $C_{1-3}$-alkyl, which may be substituted as defined hereinafter; and
wherein each alkyl, carbocyclyl and heterocyclyl are optionally substituted with one or more substituents selected from F; and wherein each alkyl, carbocyclyl and heterocyclyl are optionally substituted with one or two substituents $R^C$; and
wherein each carbocyclyl and heterocyclyl are optionally substituted with phenyl or pyridyl; and
wherein each phenyl and heteroaryl group is optionally substituted with one or more substituents L;
$R^C$ is selected from the group consisting of F, Cl, Br, CN, OH, $C_{1-4}$-alkyl-O—, $C_{3-7}$-cycloalkyl-O—, $C_{3-7}$-cycloalkyl-$C_{1-3}$-alkyl-O—, $H_2N$—, $(C_{1-4}$-alkyl)NH—, $(C_{1-4}$-alkyl$)_2$N—, $C_{1-4}$-alkyl-C(=O)—, $C_{1-4}$-alkyl-S(=O$)_2$—, HO—C(=O)—, $C_{1-4}$-alkyl-O—C(=O)—, $H_2N$—C(=O)—, $(C_{1-4}$-alkyl)HN—C(=O)— and $(C_{1-4}$-alkyl$)_2$N—C(=O)—, wherein each alkyl or cycloalkyl is optionally substituted with one or more substituents selected from F and OH; and
$R^{N1}$ is selected from the group consisting of H, $C_{1-6}$-alkyl, $C_{3-10}$-carbocyclyl, $C_{3-10}$-carbocyclyl-$C_{1-3}$-alkyl, $C_{3-6}$-alkenyl, $C_{3-6}$-alkynyl, heterocyclyl, heterocyclyl-$C_{1-3}$-alkyl, aryl, aryl-$C_{1-3}$-alkyl, heteroaryl and heteroaryl-$C_{1-3}$-alkyl,
  wherein each carbocyclyl and heterocyclyl is optionally substituted with one or more $C_{1-4}$-alkyl, and
  wherein in each carbocyclyl and heterocyclyl a —$CH_2$-group is optionally replaced by —C(=O)—, and
  wherein each alkyl, carbocyclyl and heterocyclyl is optionally substituted with one or more substituents $R^C$, and
  wherein each aryl and heteroaryl group is optionally substituted with one or more substituents L,
$R^{N2}$ is selected from the group consisting of H and $C_{1-6}$-alkyl; and
$R^{Alk}$ is selected from the group consisting of H and $C_{1-6}$-alkyl which may be substituted with one or more F atoms; and
$Ar^2$ is

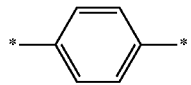 [SMILES: *c1ccc(*)cc1]

optionally substituted with one or more substituents L; and
L is selected from the group consisting of F, Cl, Br, CN, OH, $C_{1-4}$-alkyl-, $C_{1-4}$-alkyl-O—, $C_{1-4}$-alkyl-S—, $C_{1-4}$-alkyl-S(=O$)_2$—, $H_2N$—, $(C_{1-4}$-alkyl$)_2$N— and heterocyclyl, wherein each alkyl is optionally substituted with one or more F-atoms and/or with a substituent selected from OH, $C_{1-3}$-alkyl-O— and CN; and
X is selected from the group consisting of:

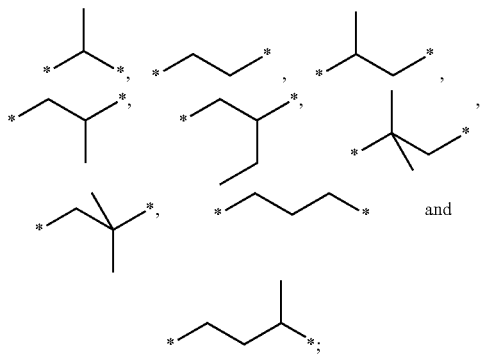

and
Y is —C(=O)—;
$T^1$ is selected from the group consisting of H, $C_{3-7}$-cycloalkyl, $C_{3-7}$-cycloalkyl-$C_{1-3}$-alkyl, phenyl, phenyl-$C_{1-3}$-alkyl, heteroaryl and heteroaryl-$C_{1-3}$-alkyl, wherein each cycloalkyl may be optionally substituted with one or more $C_{1-4}$-alkyl, which may be optionally substituted with one or more substituents $R^C$, and
wherein each alkyl and cycloalkyl may be optionally substituted with one or more substituents $R^C$; and
wherein heteroaryl is selected from the group consisting of pyridyl, pyrimidinyl, pyridazinyl, pyrazinyl, furanyl, thienyl, pyrrolyl, imidazolyl, pyrazolyl, triazolyl, oxazolyl, isoxazolyl, thiazolyl, oxadiazolyl and thiadiazolyl; and
wherein each phenyl and heteroaryl group may be optionally substituted with one or more substituents L; and
$T^2$ is selected from the group consisting of H and $C_{1-6}$-alkyl; or a salt thereof.

2. A compound according to claim 1 wherein
$R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, $(C_{1-3}$-alkyl)NH—, $(C_{1-3}$-alkyl$)_2$N—, HO—C(=O)— and $C_{1-4}$-alkyl-O—C(=O)—;
and
$T^2$ is H or methyl.

3. A compound according to claim 1 wherein $R^A$ is selected from the group consisting of F, Cl, Br, I, CN, $C_{1-5}$-alkyl, $C_{3-6}$-cycloalkyl, $C_{1-5}$-alkyl-O—, $C_{3-6}$-cycloalkyl-O—, $C_{3-6}$-cycloalkyl-$C_{1-3}$-alkyl-O—, $R^{N1}R^{N2}N$—, phenyl, phenyl-O—, heteroaryl and heteroaryl-O—; and
  wherein each cycloalkyl is optionally substituted with one or more $C_{1-3}$-alkyl, which may be substituted as defined hereinafter; and
  wherein each alkyl and cycloalkyl are optionally substituted with one or more substituents selected from F; and
  wherein in each cycloalkyl group a $CH_2$-group is optionally replaced with —O—; and
  wherein each alkyl and cycloalkyl are optionally substituted with one or two substituents $R^C$, wherein $R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, $(C_{1-3}$-alkyl)NH—, $(C_{1-3}$-alkyl$)_2$N—, HO—C(=O)— and $C_{1-3}$-alkyl-O—C(=O)—; and
  wherein each $R^{N1}$ is selected from the group consisting of H, $C_{1-6}$-alkyl, $C_{3-6}$-cycloalkyl, $C_{3-6}$-cycloalkyl-$CH_2$— and phenyl-$CH_2$—, wherein each cycloalkyl is optionally substituted with one or more $C_{1-4}$-alkyl, and wherein each alkyl and cycloalkyl are optionally substituted with one or more substituents selected from F, and wherein each alkyl and cycloalkyl are optionally substituted with a substituent selected from OH, $C_{1-3}$-alkyl-O— and $H_2N$—; and
  wherein heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, benzofuranyl, indolyl and quinolinyl; and
  wherein each phenyl and heteroaryl group is optionally substituted with one or more substituents L.

4. A compound according to claim 1 wherein X is

5. A compound according to claim 1 wherein $R^C$ is selected from the group consisting of F, CN, $C_{1-4}$-alkyl-O—, $C_{1-4}$-alkyl-O—C(=O)—, $H_2N$—C(=O)—, $(C_{1-3}$-alkyl)NH—C(=O)— and $(C_{1-3}$-alkyl$)_2$N—C(=O)—.

6. A compound according to claim 1 wherein $T^1$ is selected from the group consisting of H, $H_3C—$, $H_5C_2—$, $NC—CH_2—$,
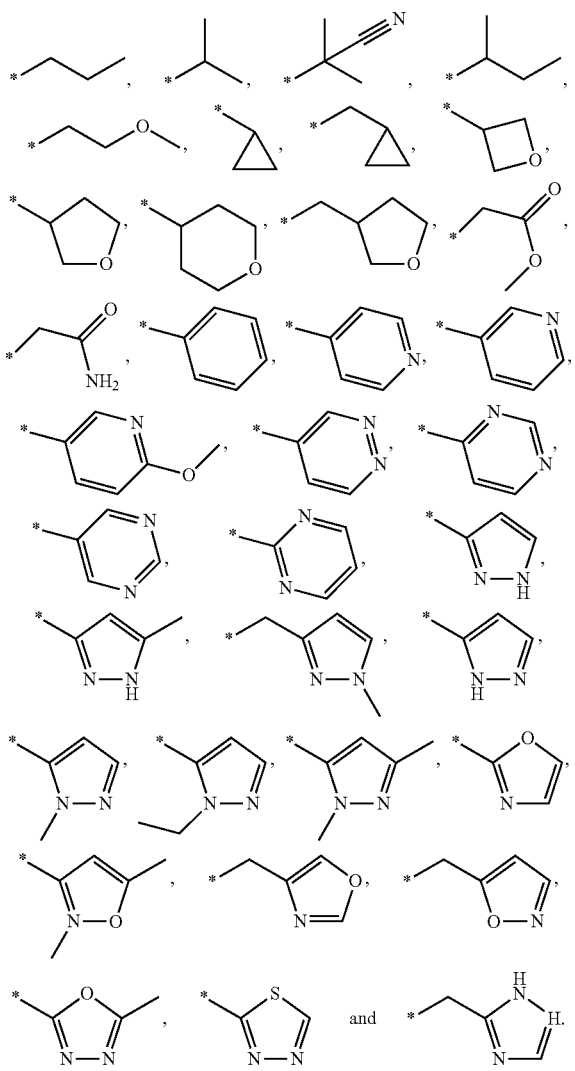
7. A compound according to claim 1 wherein $T^1$ is selected from the group consisting of H, $H_3C—$, $H_5C_2—$,
8. A pharmaceutically acceptable salt of a compound according to claim 1.
9. A compound selected from the group consisting of:
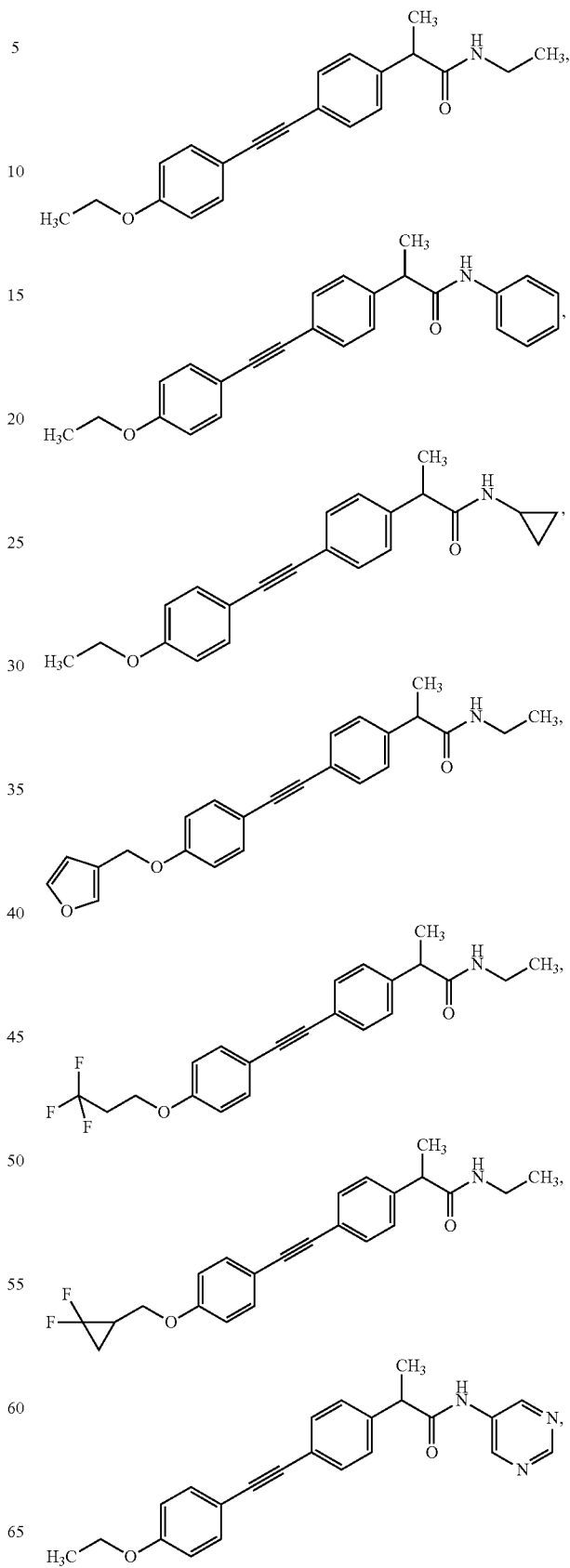

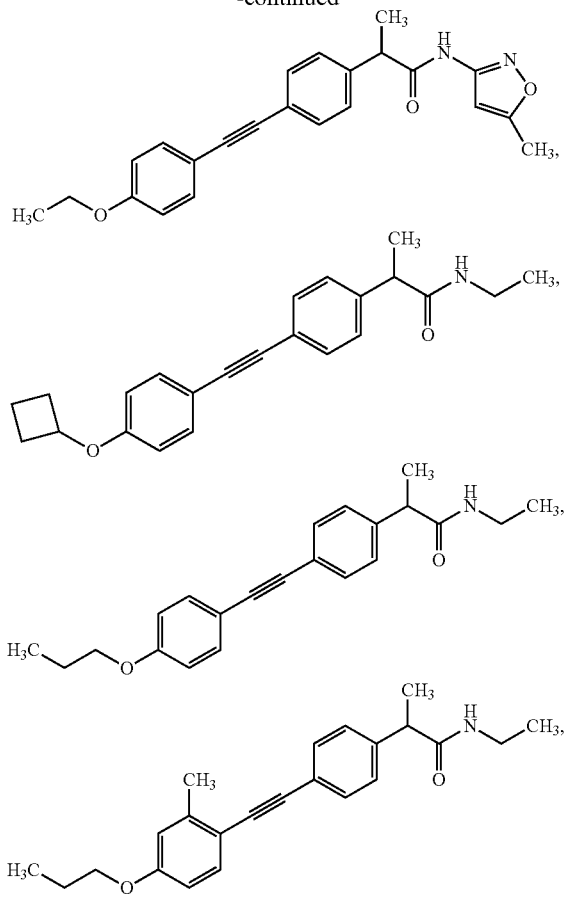
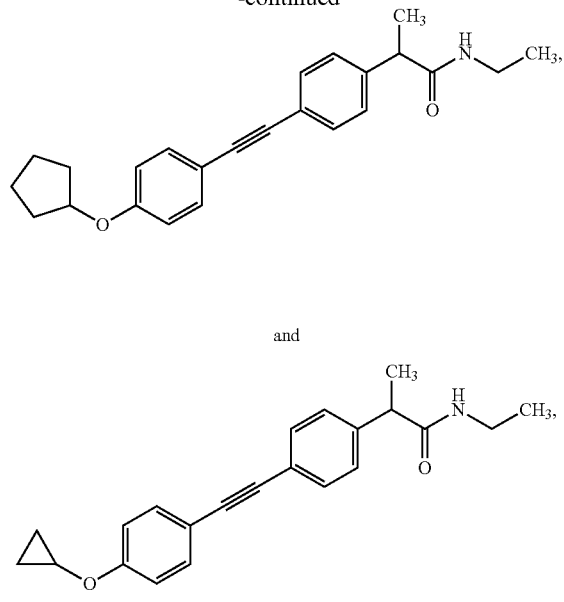
and
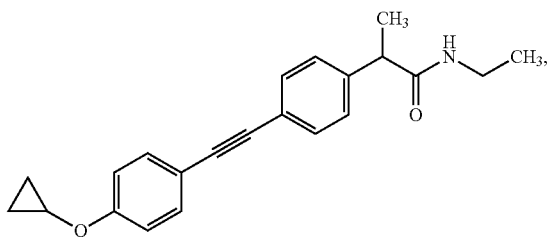
or a pharmaceutically acceptable salt thereof.
10. A pharmaceutical composition comprising a compound according to claim 1 or a pharmaceutically acceptable salt thereof together with one or more inert carriers and/or diluents.
* * * * *